(12) United States Patent
Harlev et al.

(10) Patent No.: US 12,114,921 B2
(45) Date of Patent: *Oct. 15, 2024

(54) THERAPEUTIC CATHETER WITH IMAGING

(71) Applicant: Affera, Inc., Newton, MA (US)

(72) Inventors: Doron Harlev, Brookline, MA (US); Andrew Miles Wallace, Needham, MA (US)

(73) Assignee: AFFERA, INC., Watertown, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/806,931

(22) Filed: Jun. 14, 2022

(65) Prior Publication Data
US 2023/0108429 A1 Apr. 6, 2023

Related U.S. Application Data

(63) Continuation of application No. 17/520,686, filed on Nov. 7, 2021, now abandoned, which is a (Continued)

(51) Int. Cl.
*A61B 18/14* (2006.01)
*A61B 1/00* (2006.01)
(Continued)

(52) U.S. Cl.
CPC ...... *A61B 18/1492* (2013.01); *A61B 1/00087* (2013.01); *A61B 5/6843* (2013.01);
(Continued)

(58) Field of Classification Search
CPC . A61B 18/1206; A61B 18/1233; A61B 18/14; A61B 18/148; A61B 18/1482;
(Continued)

(56) References Cited

U.S. PATENT DOCUMENTS

| 5,281,218 A | 1/1994 | Imran |
| 5,309,910 A | 5/1994 | Edwards et al. |

(Continued)

FOREIGN PATENT DOCUMENTS

| CN | 101856271 A | 10/2010 |
| CN | 104812297 A | 7/2015 |

(Continued)

OTHER PUBLICATIONS

Byun et al., Radiofrequency Ablation of the Gastrointestinal Tract with a Stent-Like Electrode: Experimental Study, Koean J Radiol 4(1), Mar. 2003, pp. 19-26.

(Continued)

*Primary Examiner* — Tigist S Demie
(74) *Attorney, Agent, or Firm* — Tarolli, Sundheim, Covell & Tummino LLP

(57) ABSTRACT

Ablation systems and methods of the present disclosure include a catheter including one or more image sensors. The one or more image sensors can facilitate, for example, positioning an ablation electrode at a treatment site of an anatomic structure and, additionally or alternatively, can facilitate controlling delivery of therapeutic energy to a treatment site of an anatomic structure.

24 Claims, 35 Drawing Sheets

Related U.S. Application Data continuation of application No. 15/584,146, filed on May 2, 2017, now Pat. No. 11,246,656.

(60) Provisional application No. 62/468,873, filed on Mar. 8, 2017, provisional application No. 62/468,339, filed on Mar. 7, 2017, provisional application No. 62/434,073, filed on Dec. 14, 2016, provisional application No. 62/428,406, filed on Nov. 30, 2016, provisional application No. 62/424,736, filed on Nov. 21, 2016, provisional application No. 62/420,610, filed on Nov. 11, 2016, provisional application No. 62/399,632, filed on Sep. 26, 2016, provisional application No. 62/399,625, filed on Sep. 26, 2016, provisional application No. 62/357,704, filed on Jul. 1, 2016, provisional application No. 62/330,395, filed on May 2, 2016.

(51) Int. Cl.
| | |
|---|---|
| *A61B 5/00* | (2006.01) |
| *A61B 18/12* | (2006.01) |
| *A61M 3/02* | (2006.01) |
| *A61M 25/00* | (2006.01) |
| *A61B 17/00* | (2006.01) |
| *A61B 18/00* | (2006.01) |
| *A61B 90/00* | (2016.01) |

(52) U.S. Cl.
CPC ........ *A61B 5/6852* (2013.01); *A61B 18/1206* (2013.01); *A61B 18/1233* (2013.01); *A61B 18/14* (2013.01); *A61B 18/148* (2013.01); *A61B 18/1482* (2013.01); *A61M 3/0295* (2013.01); *A61M 25/001* (2013.01); *A61M 25/007* (2013.01); *A61M 25/0071* (2013.01); *A61M 25/0082* (2013.01); *A61B 2017/00039* (2013.01); *A61B 2017/00053* (2013.01); *A61B 2017/00154* (2013.01); *A61B 2017/00477* (2013.01); *A61B 2017/00526* (2013.01); *A61B 2017/00867* (2013.01); *A61B 2018/00011* (2013.01); *A61B 2018/00029* (2013.01); *A61B 2018/00065* (2013.01); *A61B 2018/00077* (2013.01); *A61B 2018/00083* (2013.01); *A61B 2018/00089* (2013.01); *A61B 2018/00101* (2013.01); *A61B 2018/0016* (2013.01); *A61B 2018/00166* (2013.01); *A61B 2018/00214* (2013.01); *A61B 2018/00238* (2013.01); *A61B 2018/00267* (2013.01); *A61B 2018/00351* (2013.01); *A61B 2018/00357* (2013.01); *A61B 2018/00577* (2013.01); *A61B 2018/00642* (2013.01); *A61B 2018/00714* (2013.01); *A61B 2018/00726* (2013.01); *A61B 2018/00744* (2013.01); *A61B 2018/00767* (2013.01); *A61B 2018/00791* (2013.01); *A61B 2018/00797* (2013.01); *A61B 2018/00815* (2013.01); *A61B 2018/00821* (2013.01); *A61B 2018/00839* (2013.01); *A61B 2018/00875* (2013.01); *A61B 2018/00904* (2013.01); *A61B 2018/0091* (2013.01); *A61B 2018/00982* (2013.01); *A61B 2018/00988* (2013.01); *A61B 2018/1417* (2013.01); *A61B 2018/1465* (2013.01); *A61B 2018/1467* (2013.01); *A61B 2090/061* (2016.02); *A61B 2090/065* (2016.02); *A61B 2090/376* (2016.02); *A61B 2090/3966* (2016.02); *A61B 2217/007* (2013.01); *A61B 2218/002* (2013.01); *A61B 2218/003* (2013.01); *A61M 2205/0266* (2013.01); *A61M 2207/00* (2013.01)

(58) Field of Classification Search
CPC ............ A61B 18/1492; A61B 1/00087; A61B 2017/00039; A61B 2017/00053; A61B 2017/00154; A61B 2017/00477; A61B 2017/00526; A61B 2017/00867; A61B 2018/00011; A61B 2018/00029; A61B 2018/00065; A61B 2018/00077; A61B 2018/00083; A61B 2018/00089; A61B 2018/00101; A61B 2018/0016; A61B 2018/00166; A61B 2018/00214; A61B 2018/00238; A61B 2018/00267; A61B 2018/00351; A61B 2018/00357; A61B 2018/00577; A61B 2018/00642; A61B 2018/00714; A61B 2018/00726; A61B 2018/00744; A61B 2018/00767; A61B 2018/00791; A61B 2018/00797; A61B 2018/00815; A61B 2018/00821; A61B 2018/00839; A61B 2018/00875; A61B 2018/00904; A61B 2018/0091; A61B 2018/00982; A61B 2018/00988; A61B 2018/1417; A61B 2018/1465; A61B 2018/1467; A61B 2090/061; A61B 2090/065; A61B 2090/376; A61B 2090/3966; A61B 2217/007; A61B 2218/002; A61B 2218/003; A61B 5/6843; A61B 5/6852; A61M 2205/0266; A61M 2207/00; A61M 25/001; A61M 25/007; A61M 25/0071; A61M 25/0082; A61M 3/0295

See application file for complete search history.

(56) References Cited

U.S. PATENT DOCUMENTS

| | | |
|---|---|---|
| 5,447,529 A | 9/1995 | Marchlinski et al. |
| 5,542,928 A | 8/1996 | Evans |
| 5,588,432 A | 12/1996 | Crowley |
| 5,722,403 A | 3/1998 | McGee et al. |
| 5,797,903 A | 8/1998 | Swanson et al. |
| 5,891,134 A | 4/1999 | Goble et al. |
| 5,891,136 A | 4/1999 | McGee |
| 5,904,680 A | 5/1999 | Kordis et al. |
| 5,957,961 A | 9/1999 | Maguire et al. |
| 5,968,040 A | 10/1999 | Swanson et al. |
| 6,014,579 A | 1/2000 | Pomeranz |
| 6,036,689 A | 3/2000 | Tu et al. |
| 6,041,260 A | 3/2000 | Stern et al. |
| 6,053,913 A | 4/2000 | Tu et al. |
| 6,071,278 A | 6/2000 | Panescu et al. |
| 6,123,718 A | 9/2000 | Tu et al. |
| 6,142,993 A | 11/2000 | Whayne et al. |
| 6,165,169 A | 12/2000 | Panescu |
| 6,200,314 B1 | 3/2001 | Sherman |
| 6,246,913 B1 | 6/2001 | Sharkey |
| 6,292,695 B1 | 9/2001 | Webster, Jr. et al. |
| 6,315,778 B1 | 11/2001 | Gambale et al. |
| 6,369,465 B1 | 4/2002 | Swanson |
| 6,416,511 B1 | 7/2002 | Lesh et al. |
| 6,421,556 B2 | 7/2002 | Swanson |
| 6,537,248 B2 | 3/2003 | Mulier et al. |
| 6,572,612 B2 | 6/2003 | Stewart et al. |
| 6,632,223 B1 | 10/2003 | Keane |
| 6,658,279 B2 | 12/2003 | Swanson et al. |
| 6,813,520 B2 | 11/2004 | Truckai et al. |
| 6,837,886 B2 | 1/2005 | Collins et al. |
| 6,917,834 B2 | 7/2005 | Koblish et al. |
| 6,923,805 B1 | 8/2005 | LaFontaine et al. |
| 7,519,410 B2 | 4/2009 | Taimisto et al. |
| 7,527,625 B2 | 5/2009 | Knight et al. |
| 7,993,337 B2 | 8/2011 | Lesh |
| 8,221,407 B2 | 7/2012 | Phan et al. |

(56) References Cited

U.S. PATENT DOCUMENTS

| | | |
|---|---|---|
| 8,235,988 B2 | 8/2012 | Davis et al. |
| 8,287,533 B2 | 10/2012 | Henricus et al. |
| 8,295,902 B2 | 10/2012 | Salahieh et al. |
| 8,348,937 B2 | 1/2013 | Wang et al. |
| 8,419,725 B2 | 4/2013 | Haemmerich et al. |
| 8,444,639 B2 | 5/2013 | Arnold et al. |
| 8,449,537 B2 | 5/2013 | Cao et al. |
| 8,449,539 B2 | 5/2013 | Wang et al. |
| 8,460,285 B2 | 6/2013 | Wang et al. |
| 8,500,730 B2 | 8/2013 | Lee et al. |
| 8,500,731 B2 | 8/2013 | Byrd et al. |
| 8,504,132 B2 | 8/2013 | Friedman et al. |
| 8,527,027 B2 | 9/2013 | Falwell et al. |
| 8,538,501 B2 | 9/2013 | Venkatachalam et al. |
| 8,545,408 B2 | 10/2013 | Sliwa et al. |
| 8,603,084 B2 | 12/2013 | Fish et al. |
| 8,636,732 B2 | 1/2014 | Davis et al. |
| 8,668,686 B2 | 3/2014 | Govari et al. |
| 8,702,690 B2 | 4/2014 | Paul et al. |
| 8,740,900 B2 | 6/2014 | Kim et al. |
| 8,764,742 B2 | 7/2014 | Pappone et al. |
| 8,784,413 B2 | 7/2014 | Schwartz |
| 8,790,341 B2 | 7/2014 | Pappone et al. |
| 8,801,707 B2 | 8/2014 | Francischelli et al. |
| 8,858,548 B2 | 10/2014 | Asconeguy |
| 8,882,761 B2 | 11/2014 | Desai |
| 8,900,228 B2 | 12/2014 | Grunewald et al. |
| 8,926,604 B2 | 1/2015 | Govari et al. |
| 8,956,353 B2 | 2/2015 | Govari et al. |
| 8,974,453 B2 | 3/2015 | Wang |
| 8,986,292 B2 | 3/2015 | Sliwa et al. |
| 8,992,519 B2 | 3/2015 | Kim et al. |
| 8,996,091 B2 | 3/2015 | de la Rama et al. |
| 9,011,432 B2 | 4/2015 | Boomsma et al. |
| 9,037,264 B2 | 5/2015 | Just et al. |
| 9,044,233 B2 | 6/2015 | Davis et al. |
| 9,084,611 B2 | 7/2015 | Amirana et al. |
| 9,144,458 B2 | 9/2015 | Takaoka et al. |
| 9,155,587 B2 | 10/2015 | Willis et al. |
| 9,168,093 B2 | 10/2015 | Mihalik et al. |
| 9,173,586 B2 | 11/2015 | Deno et al. |
| 9,226,791 B2 | 1/2016 | McCarthy et al. |
| 9,241,756 B2 | 1/2016 | Berger et al. |
| 9,265,574 B2 | 2/2016 | Bar-tal et al. |
| 9,314,299 B2 | 4/2016 | Fang |
| 9,339,325 B2 | 5/2016 | Miller et al. |
| 9,352,134 B2 | 5/2016 | Levin et al. |
| 9,387,031 B2 | 7/2016 | Stewart et al. |
| 9,445,725 B2 | 9/2016 | Govari et al. |
| 9,474,566 B2 | 10/2016 | Paul et al. |
| 9,492,227 B2 | 11/2016 | Lopes et al. |
| 9,510,892 B2 | 12/2016 | Davis et al. |
| 9,539,056 B2 | 1/2017 | Beeckler et al. |
| 9,545,285 B2 | 1/2017 | Ghaffari et al. |
| 10,105,179 B2 | 10/2018 | Harlev et al. |
| 10,219,860 B2 | 3/2019 | Harlev et al. |
| 10,932,850 B2 | 3/2021 | Harlev et al. |
| 2001/0020126 A1 | 9/2001 | Swanson |
| 2001/0034518 A1 | 10/2001 | Edwards |
| 2002/0026094 A1 | 2/2002 | Roth |
| 2002/0198492 A1 | 12/2002 | Miller et al. |
| 2003/0018362 A1 | 1/2003 | Fellows et al. |
| 2003/0032953 A1 | 2/2003 | VanDusseldorp |
| 2003/0083613 A1 | 5/2003 | Schaer |
| 2003/0093086 A1 | 5/2003 | Briggs |
| 2003/0158477 A1 | 8/2003 | Panescu |
| 2004/0087936 A1 | 5/2004 | Stern et al. |
| 2004/0199156 A1 | 10/2004 | Rioux et al. |
| 2004/0210121 A1 | 10/2004 | Fuimaono et al. |
| 2004/0215296 A1 | 10/2004 | Ganz |
| 2004/0215310 A1 | 10/2004 | Amirana |
| 2004/0254621 A1 | 12/2004 | Jones et al. |
| 2005/0020914 A1 | 1/2005 | Amundson |
| 2005/0096647 A1* | 5/2005 | Steinke ............... A61B 18/1815 606/41 |
| 2005/0171524 A1 | 8/2005 | Stern et al. |
| 2005/0171525 A1 | 8/2005 | Rioux |
| 2005/0222563 A1 | 10/2005 | McDaniel et al. |
| 2005/0245876 A1 | 11/2005 | Khosravi et al. |
| 2006/0100669 A1 | 5/2006 | Fuimaono et al. |
| 2007/0016391 A1 | 1/2007 | Minoguchi |
| 2008/0033421 A1 | 2/2008 | Davis et al. |
| 2008/0009747 A1 | 10/2008 | Saadat et al. |
| 2008/0262489 A1 | 10/2008 | Steinke |
| 2008/0281391 A1* | 11/2008 | MacAdam ......... A61B 18/1492 606/34 |
| 2008/0287942 A1 | 11/2008 | Amundson |
| 2009/0076498 A1 | 3/2009 | Saadat et al. |
| 2009/0093802 A1 | 4/2009 | Kulesa et al. |
| 2009/0171274 A1 | 7/2009 | Harlev et al. |
| 2009/0221965 A1 | 9/2009 | Osypka |
| 2010/0030209 A1 | 2/2010 | Govari et al. |
| 2010/0057072 A1 | 3/2010 | Roman et al. |
| 2010/0057074 A1 | 3/2010 | Roman et al. |
| 2010/0076426 A1 | 3/2010 | de la Rama et al. |
| 2010/0152731 A1 | 4/2010 | de la Rama |
| 2010/0145330 A1 | 6/2010 | Badie |
| 2010/0168647 A1 | 7/2010 | Tegg |
| 2010/0234807 A1 | 9/2010 | Fisher et al. |
| 2010/0240995 A1 | 9/2010 | Nuccitelli et al. |
| 2010/0324540 A1 | 12/2010 | Paulen et al. |
| 2011/0009857 A1 | 1/2011 | Subramaniam et al. |
| 2011/0022041 A1 | 1/2011 | Ingle et al. |
| 2011/0106012 A1 | 5/2011 | Velarde |
| 2011/0118726 A1 | 5/2011 | Rama et al. |
| 2011/0160584 A1 | 6/2011 | Paul et al. |
| 2011/0201973 A1 | 8/2011 | Stephens et al. |
| 2011/0257649 A1 | 10/2011 | Geistert et al. |
| 2011/0270242 A1 | 11/2011 | Marion |
| 2012/0046610 A1 | 2/2012 | Rankin |
| 2012/0101413 A1 | 4/2012 | Beetel |
| 2012/0123400 A1 | 5/2012 | Francischelli et al. |
| 2012/0136350 A1 | 5/2012 | Goshgarian et al. |
| 2012/0157890 A1 | 6/2012 | Govari et al. |
| 2012/0165809 A1 | 6/2012 | Christian et al. |
| 2012/0165812 A1 | 6/2012 | Christian |
| 2012/0172871 A1 | 7/2012 | Hastings et al. |
| 2012/0184863 A1 | 7/2012 | Harlev et al. |
| 2012/0209260 A1 | 8/2012 | Lambert et al. |
| 2012/0265192 A1 | 10/2012 | Sliwa et al. |
| 2012/0302877 A1 | 11/2012 | Harks et al. |
| 2012/0310064 A1 | 12/2012 | McGee |
| 2013/0060245 A1 | 3/2013 | Grunewald et al. |
| 2013/0066315 A1 | 3/2013 | Subramaniam et al. |
| 2013/0085413 A1 | 4/2013 | Tsamir et al. |
| 2013/0096550 A1 | 4/2013 | Hill |
| 2013/0137980 A1 | 5/2013 | Waters et al. |
| 2013/0190754 A1 | 7/2013 | Paul et al. |
| 2013/0253330 A1* | 9/2013 | Demos ................. A61B 18/24 600/473 |
| 2013/0282084 A1 | 10/2013 | Mathur et al. |
| 2013/0286012 A1 | 10/2013 | Medioni et al. |
| 2013/0296852 A1 | 11/2013 | Madjarov et al. |
| 2014/0012160 A1 | 1/2014 | Ghaffari et al. |
| 2014/0017639 A1 | 1/2014 | Zhang et al. |
| 2014/0058197 A1 | 2/2014 | Salahieh et al. |
| 2014/0058208 A1 | 2/2014 | Shafran |
| 2014/0058375 A1 | 2/2014 | Koblish |
| 2014/0107639 A1 | 4/2014 | Zhang et al. |
| 2014/0121657 A1 | 5/2014 | Bar-tal |
| 2014/0142570 A1 | 5/2014 | Bakczewitz |
| 2014/0163360 A1 | 6/2014 | Steven-Wright et al. |
| 2014/0180152 A1* | 6/2014 | Maskara ............ A61B 18/1492 600/509 |
| 2014/0206985 A1 | 7/2014 | Kariv |
| 2014/0228832 A1 | 8/2014 | Chun |
| 2014/0236146 A1 | 8/2014 | McLawhorn |
| 2014/0238175 A1 | 8/2014 | Huszar et al. |
| 2014/0257282 A1 | 9/2014 | Wang et al. |
| 2014/0276078 A1 | 9/2014 | Schweitzer et al. |
| 2014/0276562 A1 | 9/2014 | Govari et al. |
| 2014/0276617 A1 | 9/2014 | Akingba et al. |
| 2014/0316400 A1 | 10/2014 | Blix et al. |
| 2014/0316406 A1 | 10/2014 | Willis et al. |

(56) References Cited

U.S. PATENT DOCUMENTS

| | | |
|---|---|---|
| 2014/0357956 A1 | 12/2014 | Salahieh et al. |
| 2014/0364848 A1 | 12/2014 | Heimbecher et al. |
| 2015/0018818 A1 | 1/2015 | Willard et al. |
| 2015/0105645 A1 | 4/2015 | Subramaniam et al. |
| 2015/0105659 A1 | 4/2015 | Salahieh et al. |
| 2015/0119876 A1 | 4/2015 | Willard |
| 2015/0119883 A1 | 4/2015 | Buysman |
| 2015/0133920 A1 | 5/2015 | Rankin et al. |
| 2015/0141738 A1 | 5/2015 | Toellner |
| 2015/0141982 A1 | 5/2015 | Lee |
| 2015/0182282 A1 | 7/2015 | Zemel et al. |
| 2015/0202408 A1 | 7/2015 | McMurtry et al. |
| 2015/0223757 A1 | 8/2015 | Werneth et al. |
| 2015/0272667 A1 | 10/2015 | Govari et al. |
| 2015/0282859 A1 | 10/2015 | Bencini et al. |
| 2015/0297292 A1 | 10/2015 | Sutermeister |
| 2015/0327921 A1 | 11/2015 | Govari et al. |
| 2015/0327925 A1 | 11/2015 | Christian |
| 2015/0342671 A1 | 12/2015 | Govari et al. |
| 2015/0342672 A1 | 12/2015 | Bencini et al. |
| 2015/0351836 A1 | 12/2015 | Prutchi |
| 2015/0366604 A1 | 12/2015 | Shikhman |
| 2015/0374252 A1 | 12/2015 | de la Rama et al. |
| 2016/0029998 A1* | 2/2016 | Brister ............... A61B 8/0833 600/424 |
| 2016/0051321 A1 | 2/2016 | Salahieh et al. |
| 2016/0058502 A1 | 3/2016 | Clark et al. |
| 2016/0174864 A1 | 6/2016 | Levin et al. |
| 2016/0184008 A1 | 6/2016 | Papaioannou et al. |
| 2016/0228023 A1 | 8/2016 | Govari et al. |
| 2016/0278856 A1 | 9/2016 | Panescu et al. |
| 2016/0287312 A1 | 10/2016 | Tegg et al. |
| 2016/0317212 A1 | 11/2016 | Ge et al. |
| 2016/0324571 A1 | 11/2016 | Beeckler et al. |
| 2016/0331254 A1 | 11/2016 | Tegg et al. |
| 2016/0361115 A1 | 12/2016 | Bencini et al. |
| 2016/0374754 A1 | 12/2016 | Asirvatham et al. |
| 2017/0172442 A1 | 6/2017 | Govari |
| 2017/0312007 A1 | 11/2017 | Harlev et al. |
| 2017/0312008 A1 | 11/2017 | Harlev et al. |
| 2017/0312012 A1 | 11/2017 | Harlev et al. |
| 2017/0312023 A1 | 11/2017 | Harlev et al. |
| 2017/0312025 A1 | 11/2017 | Harlev et al. |
| 2017/0312027 A1 | 11/2017 | Harlev et al. |
| 2017/0312028 A1 | 11/2017 | Harlev et al. |
| 2019/0076190 A1 | 3/2019 | Harlev et al. |

FOREIGN PATENT DOCUMENTS

| | | |
|---|---|---|
| EP | 1256326 A1 | 11/2002 |
| EP | 1498080 B1 | 11/2009 |
| EP | 2201905 A1 | 6/2010 |
| EP | 1554986 B1 | 9/2010 |
| EP | 2382935 A1 | 11/2011 |
| EP | 2913017 A1 | 9/2015 |
| EP | 2470099 B1 | 10/2015 |
| EP | 2229904 B1 | 2/2016 |
| EP | 3141181 A1 | 3/2017 |
| JP | H0838503 A | 2/1996 |
| JP | 4062935 B2 | 3/2008 |
| JP | 2009-532162 A | 9/2009 |
| JP | 2012-520474 A | 9/2012 |
| WO | 2001022897 A1 | 4/2001 |
| WO | 2004110258 A2 | 12/2004 |
| WO | 2010056771 A1 | 5/2010 |
| WO | 2011101778 A1 | 8/2011 |
| WO | 2014132463 A1 | 9/2014 |
| WO | 2014168987 A1 | 10/2014 |
| WO | 2015/200518 A1 | 12/2015 |
| WO | 2017192477 A1 | 11/2017 |
| WO | 2017192480 A2 | 11/2017 |
| WO | 2017192495 A1 | 11/2017 |
| WO | 2017192510 A9 | 11/2017 |
| WO | 2017192542 A2 | 11/2017 |

OTHER PUBLICATIONS

Goldberg, S. N. et al., "Percutaneous Radiofrequency Tissue Ablation: Optimization of Pulsed-Radiofrequency Technique to Increase Coagulation Necrosis", JVIR; vol. 10 No. 7, Jul.-Aug. 1999, pp. 907-916.

International Search Report and Written Opinion dated Nov. 15, 2017; International Application No. PCT/US2017/030575; 15 pages.

International Search Report and Written Opinion mailed Nov. 15, 2017; International Patent Application No. PCT/US2017/030495; 16 pages.

International Search Report and Written Opinion mailed Sep. 7, 2017; International Patent Application No. PCT/US2017/030518; 13 pages.

ISA, "PCT Application No. PCT/US17/30492 International Search Report and Written Opinion mailed Jul. 25, 2017", 16 pages. (14 pgs without cover/end page).

ISA, "PCT Application No. PCT/US17/30495 Invitation to Pay Additional Fees and Partial International Search Report mailed Sep. 8, 2017", 14 pages. (our copy 11 pages).

ISA, "PCT Application No. PCT/US17/30535 International Search Report and Written Opinion mailed Jan. 5, 2018", 15 pages.

ISA, "PCT Application No. PCT/US17/30535 Invitation to Pay Additional Fees and Partial Search Report mailed Sep. 14, 2017", 12 pages.

ISA, "PCT Application No. PCT/US17/30575 Invitation to Pay Additional Fees and Partial Search Report mailed Sep. 20, 2017", 14 pages.

International Search Report and Written Opinion dated Apr. 14, 2021 for International Patent Application No. PCT/US20/65314, 13 pages.

Koruth et al., Bipolar irrigated radiofrequency ablation: A therapeutic option for refractory intramural atrial and ventricular tachycardia circuits, Heart Rhythm, Dec. 2012, vol. 9, Issue 12, pp. 1932-1941.

Kumar, et al., "Better Lesion Creation and Assessment During Catheter Ablation", Journal of Atrial Fibrillation, vol. 8, Issue 3, Oct.-Nov. 2015, 12 Pages.

Mddi, "Machining Materials: A Primer on Photoetching", Medical Service and Diagnostics Industry http://www.mddionline.com/article/machining-materials-primer-photoetching Jan. 1, 2008, 3 Pages.

Sapp et al., Deep Myocardial Ablation Lesions Can Be Created with a Retractable Nedele-Tipped Catheter, Pacing and Clinical Electrophysiology, vol. 27, Issue 5, May 2004, pp. 594-599.

Solazzo, Stephanie A. et al., "High-Power Generator for Radiofrequency Ablation: Larger Electrodes and Pulsing Algorithms in Bovine ex Vivo and Porcine in Vivo Settings", Experimental Studies; Radiology; vol. 242; No. 3, Mar. 2007, pp. 743-750.

1 Applicant: Affera, Inc.; European Application No. 17733196.4; European Office Action dated Jan. 12, 2024; 5 pgs.

* cited by examiner

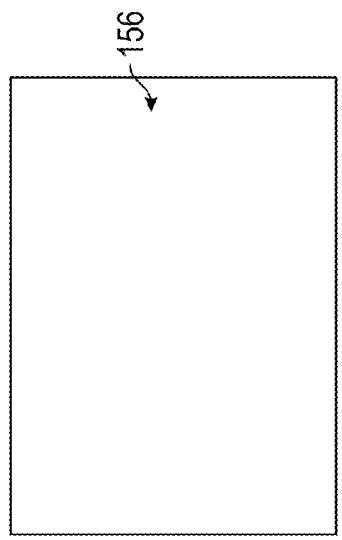

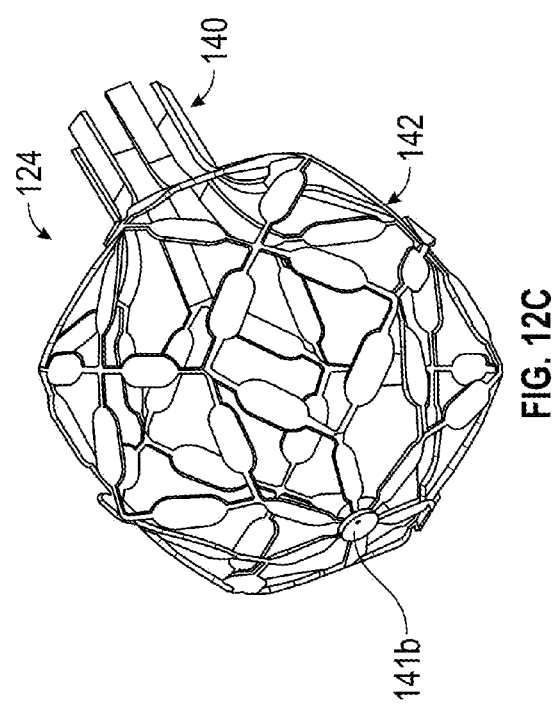

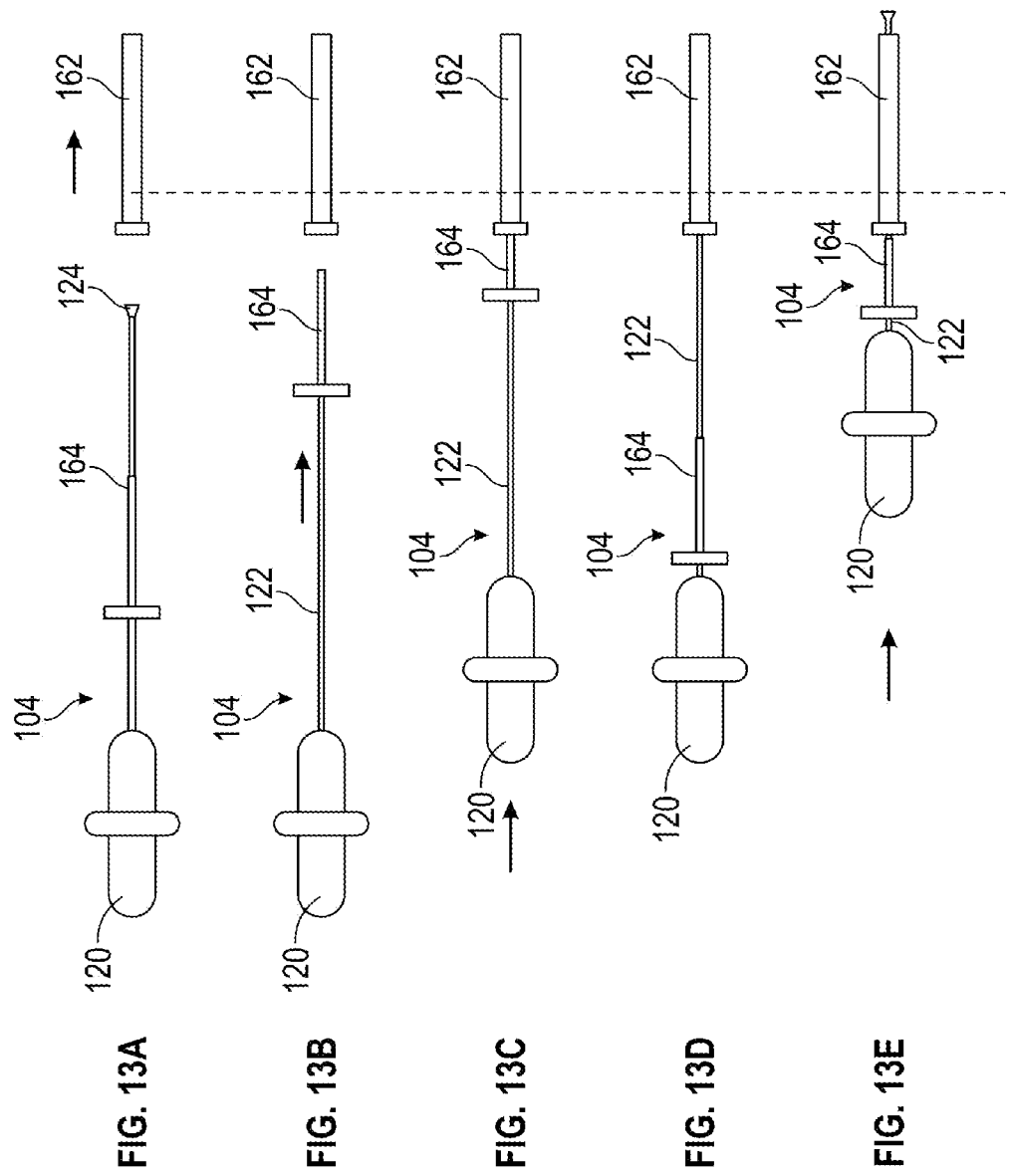

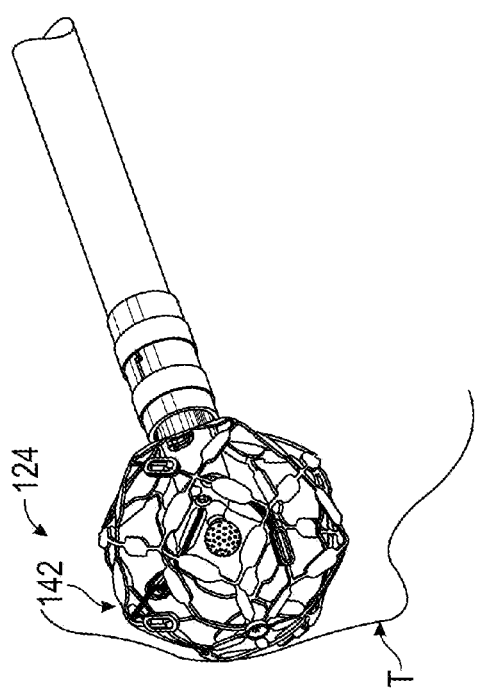

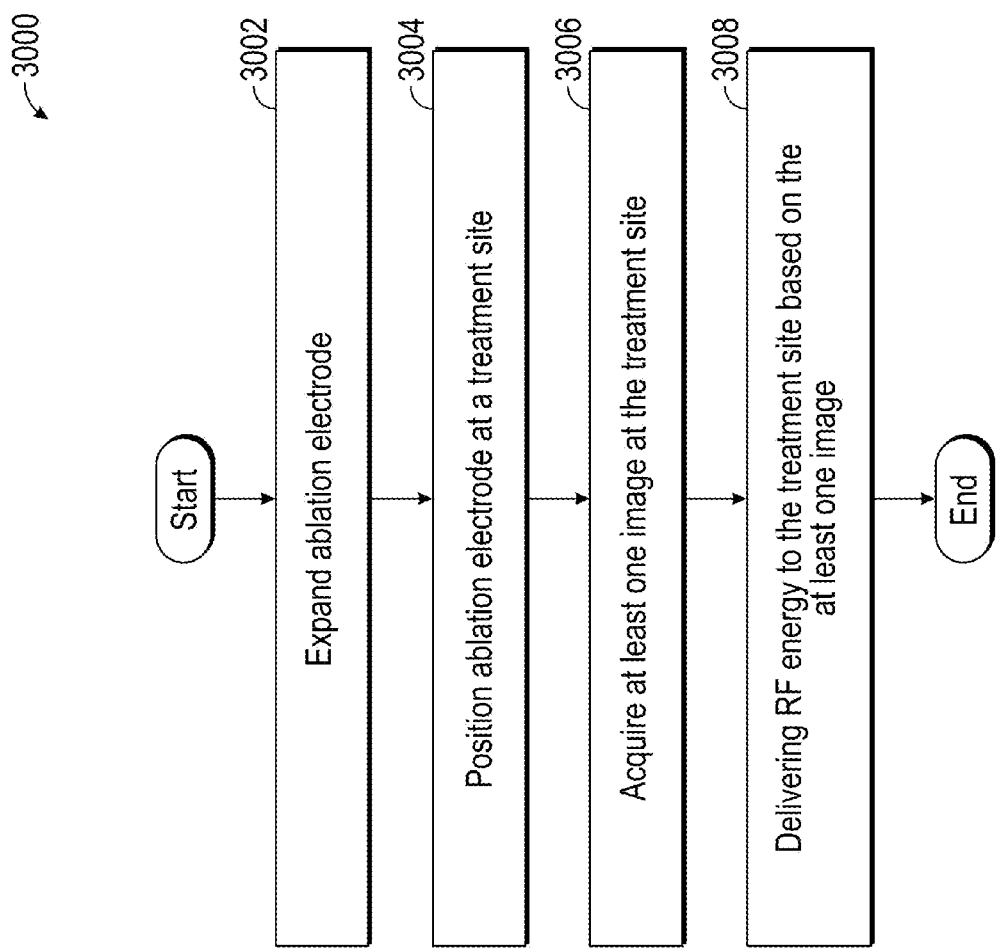

THERAPEUTIC CATHETER WITH IMAGING

CROSS-REFERENCE TO RELATED APPLICATIONS

This application claims the benefit under 35 U.S.C. § 119(e) of U.S. Prov. App. No. 62/330,395, filed May 2, 2016, U.S. Prov. App. No. 62/357,704, filed Jul. 1, 2016, U.S. Prov. App. No. 62/399,632, filed Sep. 26, 2016, U.S. Prov. App. No. 62/399,625, filed Sep. 26, 2016, U.S. Prov. App. No. 62/420,610, filed Nov. 11, 2016, U.S. Prov. App. No. 62/424,736, filed Nov. 21, 2016, U.S. Prov. App. No. 62/428,406, filed Nov. 30, 2016, U.S. Prov. App. No. 62/434,073, filed Dec. 14, 2016, U.S. Prov. App. No. 62/468,339, filed Mar. 7, 2017, and U.S. Prov. App. No. 62/468,873, filed Mar. 8, 2017, with the entire contents of each of these applications hereby incorporated herein by reference.

This application is also related to the following commonly-owned U.S. patent applications filed on even date herewith: entitled "CATHETER SENSING AND IRRIGATING"; entitled "LESION FORMATION"; entitled "PULSED RADIOFREQUENCY ABLATION"; and entitled "CATHETER INSERTION." Each of the foregoing applications is hereby incorporated herein by reference in its entirety.

BACKGROUND

Abnormal rhythms generally referred to as arrhythmia can occur in the heart. Cardiac arrhythmias develop when abnormal conduction in the myocardial tissue modifies the typical heartbeat pattern. Radio frequency ("RF") catheter ablation can be used to form lesions that interrupt the mechanism of abnormal conduction to terminate certain arrhythmias.

SUMMARY

Ablation systems and methods of the present disclosure include a catheter including one or more image sensors. The one or more image sensors can facilitate, for example, positioning an ablation electrode at a treatment site of an anatomic structure and, additionally or alternatively, can facilitate controlling delivery of therapeutic energy to a treatment site of an anatomic structure.

According to one aspect, a catheter includes a catheter shaft having a proximal end portion and a distal end portion, an ablation electrode coupled to the distal end portion of the catheter shaft, and at least one image sensor (e.g., at least three image sensors). The ablation electrode has an inner portion and an outer portion opposite the inner portion. The at least one image sensor is spaced from the inner portion of the ablation electrode and disposed within a volume at least partially defined by the ablation electrode, and the at least one image sensor is directed toward the inner portion of the ablation electrode.

In certain implementations, the ablation electrode can include a deformable portion movable in a direction away from the at least one image sensor as the deformable portion expands from a compressed state to an uncompressed state.

In some implementations, the at least one image sensor can be enveloped by the ablation electrode. For example, the ablation electrode can be at least partially transparent to imaging energy from the at least one image sensor such that the ablation electrode reflects less than half of the imaging energy directed from the at least one image sensor toward the ablation electrode. Additionally, or alternatively, the ablation electrode can define an open area greater than the total surface area of the inner portion of the ablation electrode.

In certain implementations, the catheter can further include an irrigation element coupled to the distal end portion of the catheter shaft. The at least one image sensor can be disposed, for example, along the irrigation element. Further, or instead, the irrigation element can define irrigation holes directed toward a respective field of view of the at least one image sensor. As an example, the irrigation holes defined by the irrigation element can be directed toward the respective field of view of the at least one image sensor between the irrigation element and the inner portion of the ablation electrode.

In some implementations, the at least one image sensor includes a camera. The camera can include, for example, a light source directed toward the inner portion of the ablation electrode. Additionally, or alternatively, the camera can have at least one field of view including a distal half of the ablation electrode. For example, the ablation electrode can include a substantially spherical portion, and the camera can have at least one field of view including an equator of the substantially spherical portion. By way of further or alternative example, the at least one image sensor can be spaced from the inner portion of the ablation electrode by a distance less than a focal length of the at least one image sensor.

In certain implementations, the at least one image sensor includes at least one ultrasound transducer. For example, the ablation electrode can include a plurality of struts, the plurality of struts collectively defining a plurality of open cells. The at least one ultrasound transducer can have a beam width at least twice as wide as a respective transverse dimension of at least some of the struts. The at least one ultrasound transducer can be, for example, radially symmetric. Additionally, or alternatively, the at least one image sensor can include an ultrasound transducer array. Further, or instead, the at least one image sensor can be spaced from the inner portion of the ablation electrode by a distance greater than a focal length of the at least one image sensor.

In some implementations, the at least one image sensor can be directed in a distal direction.

In certain implementations, the catheter can further include a location sensor fixed relative to the distal end portion of the catheter shaft. The location sensor can include, for example, a magnetic sensor.

According to another aspect, a catheter ablation system includes a catheter and a catheter interface unit in electrical communication with the catheter. The catheter includes a catheter shaft having a proximal end portion and a distal end portion, an ablation electrode coupled to the distal end portion of the catheter shaft, the ablation electrode having an inner portion and an outer portion opposite the inner portion, and at least one image sensor spaced from the inner portion of the ablation electrode and disposed within a volume at least partially defined by the ablation electrode, the at least one image sensor directed toward the inner portion of the ablation electrode. The catheter interface unit includes one or more processors and a non-transitory, computer readable storage medium having stored thereon computer executable instructions for causing the one or more processors to receive at least one image from the at least one image sensor, based at least in part on the at least one image, generate a graphical representation of an anatomic structure, and send the graphical representation of the anatomic structure to a graphical user interface.

In certain implementations, the computer executable instructions for causing the one or more processors to generate the graphical representation of the anatomic structure can further include slicing the graphical representation of the anatomic structure along a plane extending through the graphical representation of the anatomic structure.

In some implementations, the graphical representation of the anatomic structure can be based at least in part on a plurality of images, at least some of the images in the plurality of images corresponding to different locations of the ablation electrode in the anatomic structure.

In certain implementations, the computer executable instructions for causing the one or more processors to generate the graphical representation of the anatomic structure can be further based at least in part on location of the ablation electrode in the anatomic structure. For example, the location of the ablation electrode in the anatomic structure can be based at least in part on an electric field present in at least a portion of the anatomic structure.

In some implementations, the location of the ablation electrode in the anatomic structure can be based at least in part on a signal from a magnetic sensor fixed relative to the distal end portion of the catheter shaft.

In certain implementations, the computer executable instructions for causing the one or more processors to generate the graphical representation of the anatomic structure can include computer executable instructions for causing the one or more processors to detect a shape of the anatomic structure, a shape the ablation electrode, or a combination thereof.

In some implementations, the computer executable instructions for causing the one or more processors to generate the graphical representation of the anatomic structure can include computer executable instructions for causing the one or more processors to detect an anatomical boundary (e.g., a blood-tissue boundary) based at least in part on the at least one image.

In certain implementations, the computer executable instructions of causing the one or more processor to generate the graphical representation of the anatomic structure can include computer executable instructions for causing the one or more processors to determine thickness of the anatomic structure based at least in part on the at least one image and to display visual indicia of the thickness on the graphical user interface. For example, the anatomic structure can be a cavity of a heart, and the thickness can be the distance between endocardial tissue and epicardial tissue.

In some implementations, the computer executable instructions of causing the one or more processor to generate the graphical representation of the anatomic structure can include computer executable instructions for causing the one or more processors to detect a change in color of tissue in the anatomic structure based at least in part on the at least one image and to send to the graphical user interface an indication of the change in color of tissue in the anatomic structure. For example, the change in color of tissue in the anatomic structure can be indicative of lesion progress.

According to another aspect, a catheter ablation system can include a catheter and a catheter interface unit in electrical communication with the catheter. The catheter can include a catheter shaft having a proximal end portion and a distal end portion, an ablation electrode coupled to the distal end portion of the catheter shaft, the ablation electrode having an inner portion and an outer portion opposite the inner portion, and at least one image sensor spaced from the inner portion of the ablation electrode and disposed within a volume at least partially defined by the ablation electrode, the at least one image sensor directed toward the inner portion of the ablation electrode. The catheter interface unit can include one or more processors and a non-transitory, computer readable storage medium having stored thereon computer executable instructions for causing the one or more processors to receive at least one image from the at least one image sensor, and, based at least in part on the at least one image, determine thickness of tissue of an anatomic structure.

In certain implementations, the computer executable instructions for causing the one or more processors to determine thickness of tissue of the anatomic structure can be further based on a three-dimensional localization of the image sensor. For example, the computer executable instructions for causing the one or more processors to determine thickness of tissue of the anatomic structure can be further based on information from one or more previous positions of the image sensor. Additionally, or alternatively, the information from one or more previous positions of the image sensor can include one or more images associated with the respective one or more previous positions of the image sensor. Further or instead, the information from one or more previous positions of the image sensor can include one or more three-dimensional locations associated with the respective one or more previous positions of the image sensor.

According to another aspect, a method includes expanding an ablation electrode from a compressed state to an uncompressed state, an inner portion of the ablation electrode in the uncompressed state enveloping at least one image sensor, positioning an outer portion of the ablation electrode at a treatment site in an anatomic structure, the outer portion of the ablation electrode opposite the inner portion of the ablation electrode, acquiring at least one image of the treatment site from the at least one image sensor, and delivering RF energy to the ablation electrode at the treatment site based at least in part on the at least one image of the treatment site.

In certain implementations, expanding the ablation electrode from the compressed state to the uncompressed state can include moving the ablation electrode in a direction away from the at least one image sensor.

In some implementations, blood can be movable between the at least one image sensor and the inner portion of the ablation electrode with the ablation electrode in the uncompressed state.

In certain implementations, the method can further include determining tissue thickness at the treatment site based at least in part on the at least one image. For example, delivering RF energy to the ablation electrode can be based on the tissue thickness at the treatment site.

In some implementations, the method can further include detecting an anatomic boundary based on the at least one image of the treatment site. For example, positioning the outer portion of the ablation electrode at the treatment site can be based at least in part on the detected anatomic boundary.

In some implementations, acquiring the at least one image of the treatment site can include acquiring a plurality of images of the treatment site from respective different locations of the ablation electrode within the anatomic structure. For example, the method can further include determining a location associated with each respective image and forming a graphical representation of an anatomic boundary (e.g., a representation of endocardial tissue of a heart) based on the plurality of images of the treatment site and the location associated with each respective image. The graphical representation of the anatomic boundary can include, for example, a representation of tissue thickness. Additionally, or alternatively, determining the location associated with each respective image can be based on an electric field present in at least a portion of the anatomic structure. The electric field can be, in some instances, at least partially generated by one or more electrodes external to the anatomic structure. Additionally, or alternatively, the electric field can be at least partially generated by one or more electrodes carried by the ablation electrode within the anatomic structure.

In certain implementations, determining the location associated with each respective image can include receiving a signal from a location sensor (e.g., a magnetic sensor) associated with the ablation electrode. For example, the location sensor can be fixed relative to a distal end portion of a catheter shaft coupled to the ablation electrode.

In some implementations, the at least one image sensor can include at least one camera and acquiring the image of the treatment site from the at least one image sensor can include delivering irrigation fluid to a respective field of view of the least one camera. For example, the at least one image sensor can be spaced from the inner portion of the ablation electrode by a distance less than a focal length of the at least one image sensor. Additionally, or alternatively, the irrigation fluid can be delivered between the at least one camera and the inner portion of the ablation electrode.

In certain implementations, the at least one image sensor can include at least one ultrasound transducer. For example, the at least one image sensor can be spaced from the inner portion of the ablation electrode by a distance greater than a focal length of the at least one image sensor.

In some implementations, delivering RF energy to the ablation electrode can be based on detection of microbubbles detected by the at least one image sensor.

Other aspects, features, and advantages will be apparent from the description and drawings, and from the claims.

BRIEF DESCRIPTION OF THE DRAWINGS

FIGS. 12A-12C are schematic representations of a method of forming the ablation electrode of the ablation system of FIG. 1.

FIGS. 13A-13E are schematic representations of a method of inserting the catheter of FIG. 2 into a patient.

FIGS. 14A-C are schematic representations of a method of positioning the ablation electrode of the ablation system of FIG. 1 at a treatment site of a patient.

FIG. 30 is a flowchart of an exemplary method of delivering therapy to a treatment site.

Like reference symbols in the various drawings indicate like elements.

DETAILED DESCRIPTION

The present disclosure is generally directed to systems and methods of ablating tissue of a patient during a medical procedure being performed on an anatomic structure of the patient. By way of non-limiting example and for the sake of clarity of explanation, the systems and methods of the present disclosure are described with respect to ablation of tissue in a heart cavity of the patient as part of an ablation treatment associated with the treatment of cardiac arrhythmia. However, it should be appreciated that, unless otherwise specified, the systems and methods of the present disclosure can be used for any of various different medical procedures, such as procedures performed on a hollow anatomic structure of a patient, in which ablation of tissue is part of a medical treatment.

As used herein, the term "physician" should be considered to include any type of medical personnel who may be performing or assisting a medical procedure.

As used herein, the term "patient" should be considered to include any mammal, including a human, upon which a medical procedure is being performed.

Figure 1:
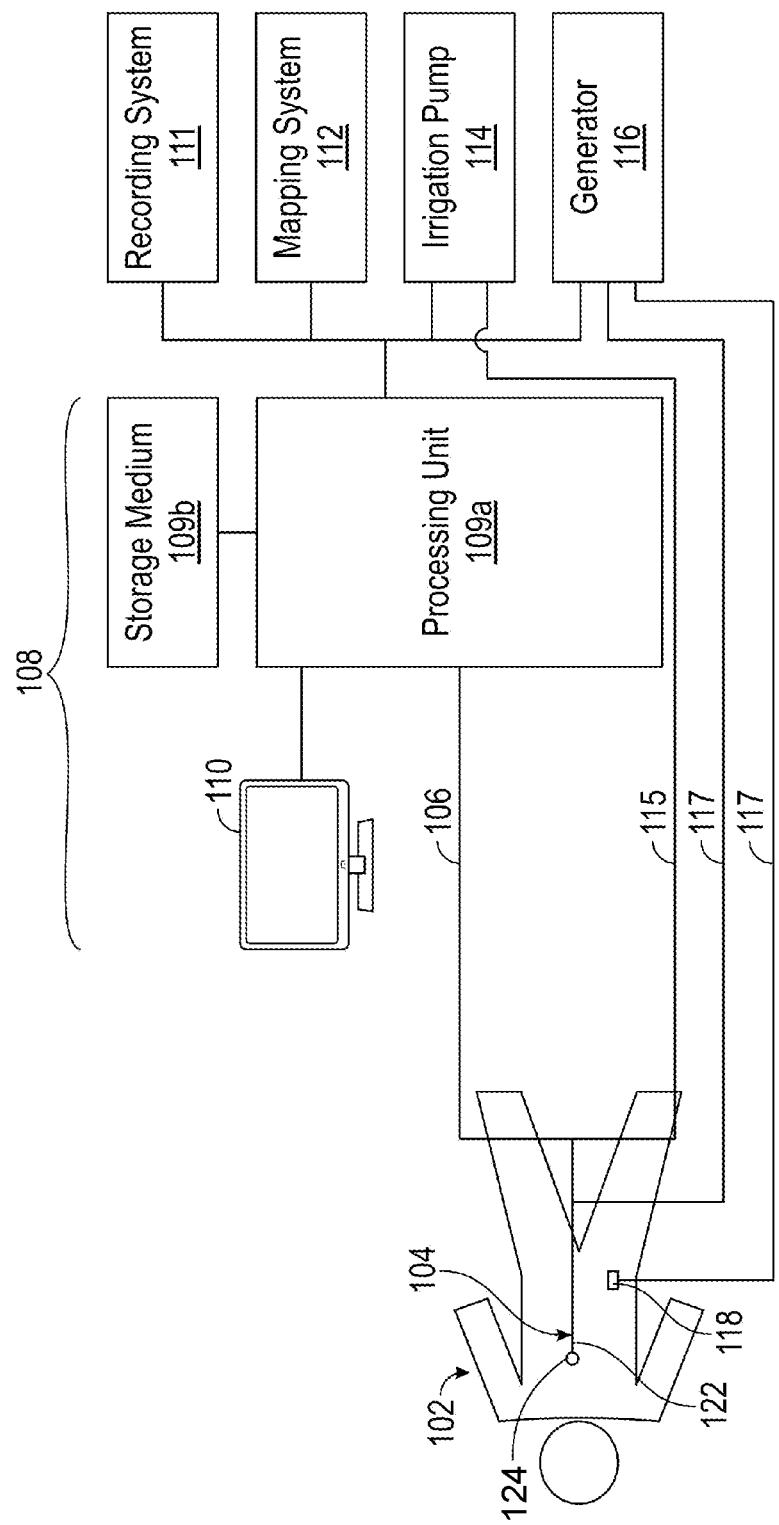
FIG. 1 is a schematic representation of an ablation system during an ablation treatment.

FIG. 1 is a schematic representation of an ablation system 100 during a cardiac ablation treatment being performed on a patient 102. The ablation system 100 includes a catheter 104 connected, via an extension cable 106, to a catheter interface unit 108. The catheter interface unit 108 can be a computing device that includes a processing unit 109a, a non-transitory, computer readable storage medium 109b, and a graphical user interface 110. The processing unit 109a can be a controller including one or more processors, and the storage medium 109b can have stored thereon computer executable instructions for causing the one or more processors of the processing unit 109a to carry out one or more portions of the various methods described herein, unless otherwise indicated or made clear from the context.

A mapping system 112, a recording system 111, an irrigation pump 114, and a generator 116 can be connected to the catheter interface unit 108. The irrigation pump 114 can be removably and fluidly connected to the ablation catheter 104 via fluid line 115. The generator 116 can also, or instead, be connected, via one or more of wires 117, to one or more return electrodes 118 attached to the skin of the patient 102. The recording system 111 can be used throughout the ablation treatment, as well as before or after the treatment. The mapping system 112 can be used prior to and/or during an ablation treatment to map the cardiac tissue of the patient 102 and determine which region or regions of the cardiac tissue require ablation.

Figure 2:
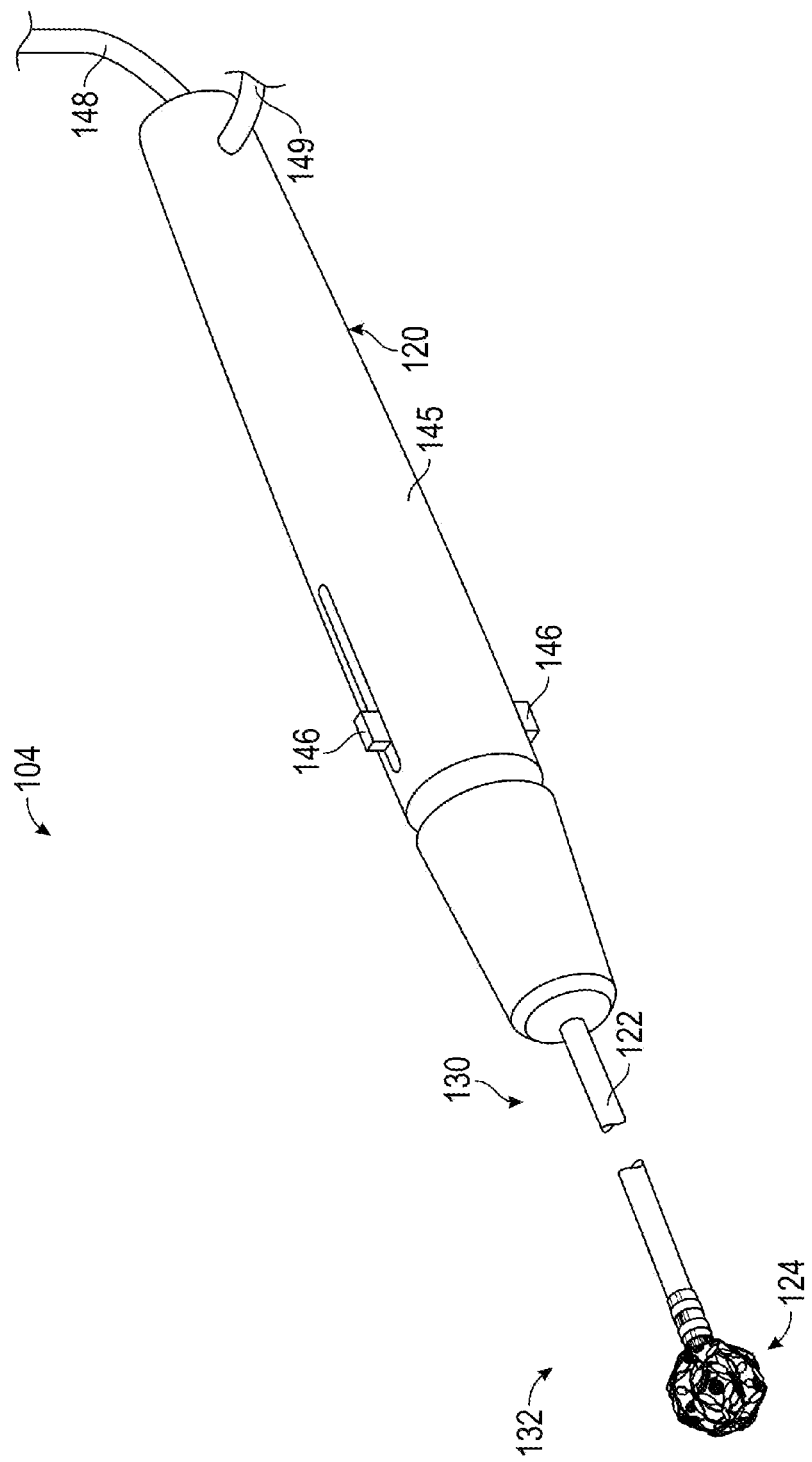
FIG. 2 is a perspective view of a catheter of the ablation system of FIG. 1.
Figure 3:
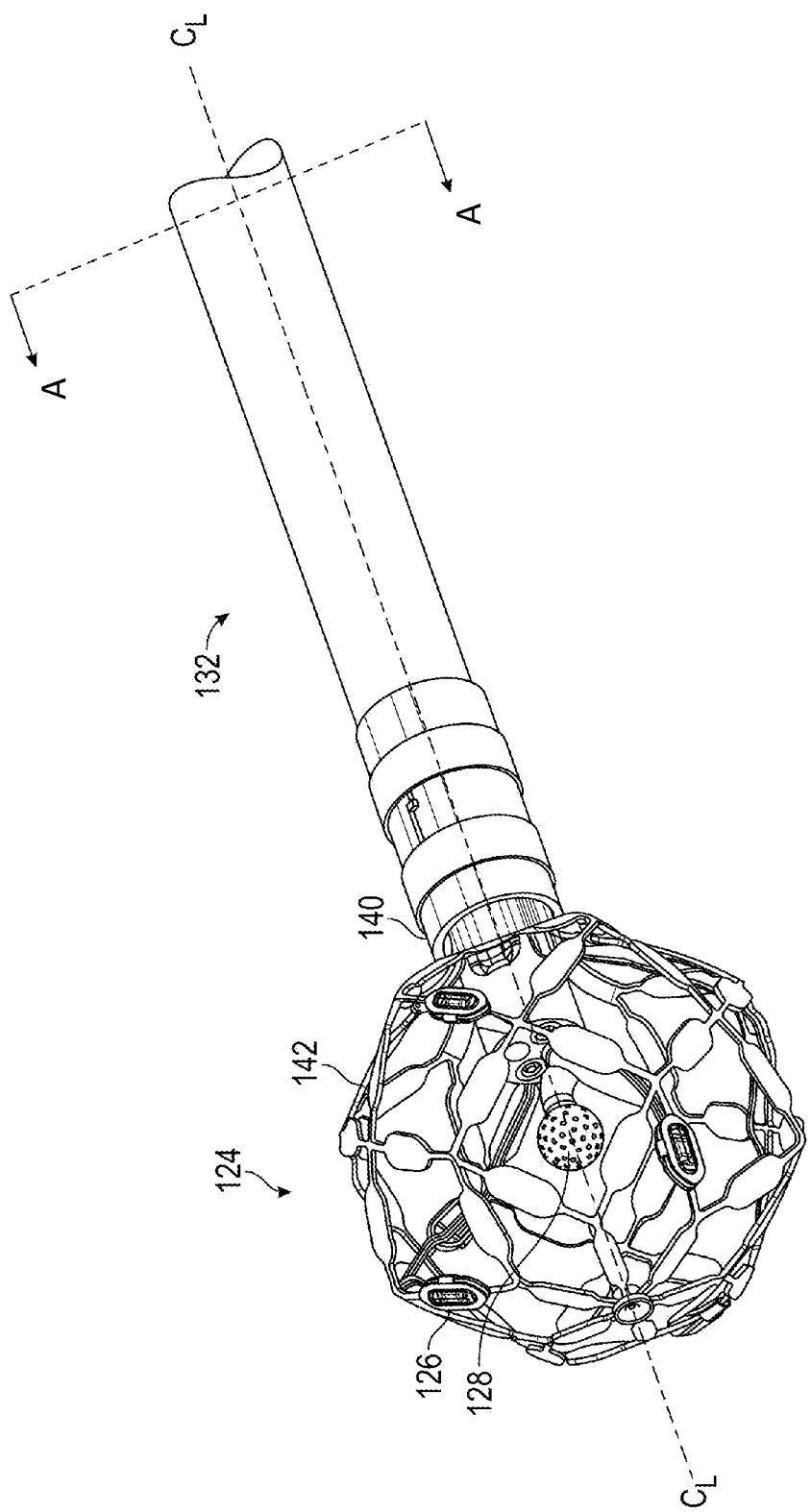
FIG. 3 is a perspective view of a distal end portion of the catheter of the ablation system of FIG. 1.
Figure 4:
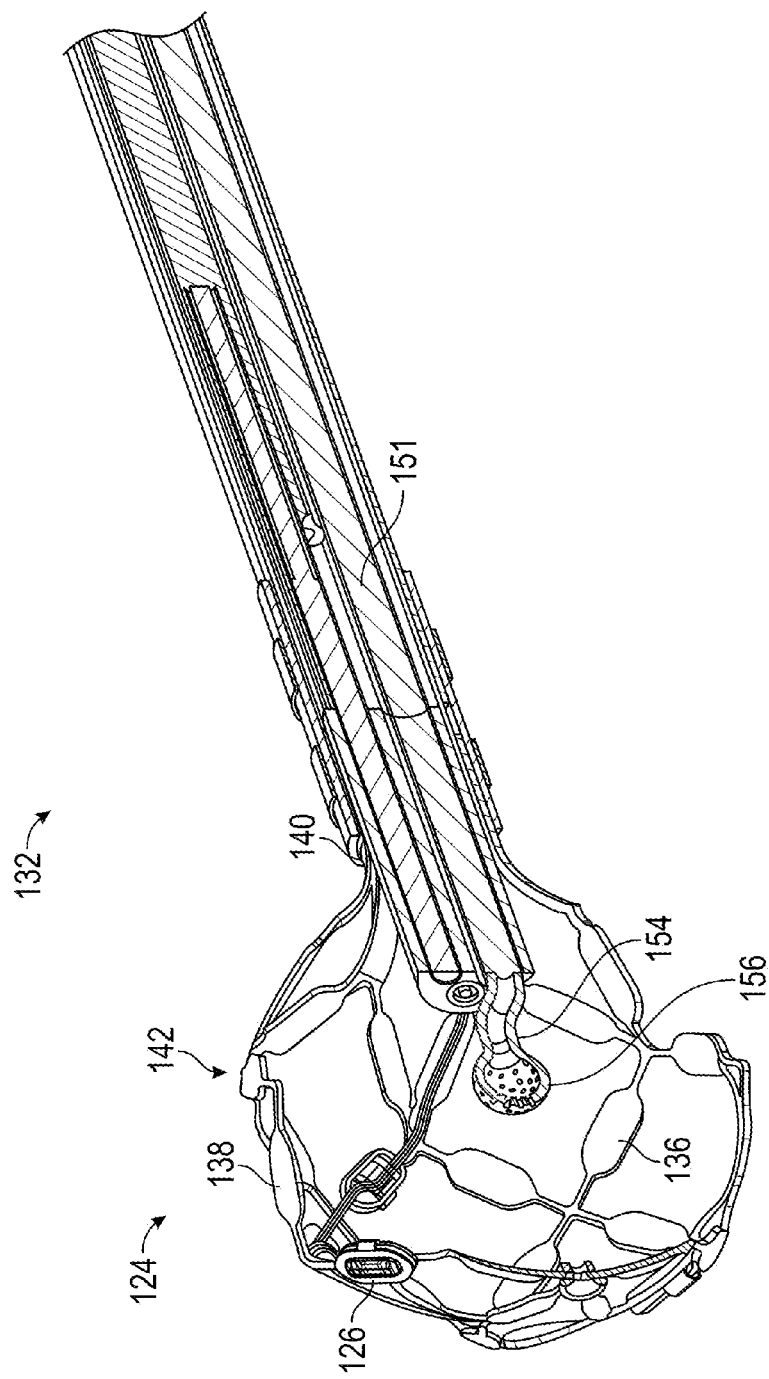
FIG. 4 is a cross-sectional perspective view along cross-section A-A of FIG. 3.

Referring now to FIGS. 2-4, the catheter 104 can include a handle 120, a catheter shaft 122, an ablation electrode 124, sensors 126, and an irrigation element 128. The handle 120 is coupled to a proximal end portion 130 of the catheter shaft 122, and a distal end portion 132 of the catheter shaft 122 can be coupled to the irrigation element 128 and to the ablation electrode 124, which supports the sensors 126 in some implementations. The handle 120 can, further or instead, be coupled to the fluid line 115 and to one or more of the wires 117 for delivery of irrigation fluid and electrical energy, respectively, along the catheter shaft 122, to the ablation electrode 124.

As described in further detail below, in a deployed state of the ablation electrode 124, irrigation fluid exits irrigation holes 134 defined by the irrigation element 128 and is directed toward an inner portion 136 of the ablation electrode 124 while an outer portion 138 (opposite the inner portion 136) of the ablation electrode 124 is in contact with tissue as part of an ablation treatment. Spacing between the irrigation holes 134 and the inner portion 136 of the ablation electrode 124 can facilitate heat transfer between the irrigation fluid and the ablation electrode 124. For example, in the spacing between the irrigation holes 134 and the inner portion 136 of the ablation electrode 124, the respective jets of irrigation fluid can develop turbulent characteristics. Without wishing to be bound by theory, it is believed that, as compared to non-turbulent or less turbulent flow of irrigation fluid, increased turbulence can improve local heat transfer from the ablation electrode 124 (e.g., from the inner portion 136 of the ablation electrode 124 to the irrigation fluid). Additionally, or alternatively, blood can flow through the spacing between the irrigation holes 134 and the inner portion 136 of the ablation electrode 124. As compared to configurations in which the flow of blood away from the treatment site is impeded, the flow of blood through the spacing between the irrigation holes 134 and the inner portion 136 of the ablation electrode 124 can, additionally or alternatively, improve further the local heat transfer from the outer portion 138 of the ablation electrode 124. In general, it should be appreciated that such improved local heat transfer can reduce the likelihood of blood clot or charring. As used herein, the term "holes" should be understood to include any size and shape of discrete orifice having a maximum dimension and through which fluid can flow and, thus, should be understood to include any manner and form of substantially geometric shapes (e.g., substantially circular shapes) and, also or instead, substantially irregular shapes, unless otherwise specified or made clear from the context.

As also described in further detail below, the ablation electrode 124 can include a coupling portion 140 and a deformable portion 142. As used herein, the terms "expandable" and "deformable" are used interchangeably, unless otherwise specified or made clear from the context. Thus, for example, it should be understood that the deformable portion 142 is expandable unless otherwise specified.

The coupling portion 140 is secured to the distal end portion 132 of the catheter shaft 122, and the deformable portion 142 can extend distally from the coupling portion 140. The deformable portion 142 of the ablation electrode 142 can be deformed for delivery (e.g., through an introducer sheath, such as an 8F introducer sheath) and expanded at a treatment site to have a cross-sectional dimension larger than a cross-sectional dimension of the catheter shaft 122. As compared to smaller ablation electrodes, the ablation electrode 124 can provide wider lesions within a shorter period of time, facilitating the creation of a pattern of overlapping lesions (e.g., reducing the likelihood of arrythmogenic gaps, and reducing the time and number of lesions required for an overlapping pattern, or both). Additionally, or alternatively, a larger tip can facilitate the delivery of more power for providing wider and deeper lesions.

Further, in an expanded state, the deformable portion 142 of the ablation electrode 124 is deformable upon sufficient contact force with tissue, and the shape and extent of the deformation can be detected based, at least in part, upon signals received from the sensors 126 on the deformable portion 142 of the ablation electrode 124. As described in greater detail below, the sensors 126 can be used in one or more modes of parameter measurement and, for example, can include one or more of an electrode, a thermistor, an ultrasound transducer, and an optical fiber. Additionally, or alternatively, the deformable portion 142 can be radiopaque such that deformation of the deformable portion 142 as a result of contact with tissue is observable, for example, through X-ray or similar visualization techniques. The detection and/or observation of the deformation of the deformable portion 142 of the ablation electrode 124 can, for example, provide improved certainty that an intended treatment is, in fact, being provided to tissue. It should be appreciated that improved certainty of positioning of an ablation electrode with respect to tissue can reduce the likelihood of gaps in a lesion pattern and, also or instead, can reduce the time and number of ablations otherwise required to avoid gaps in a lesion pattern.

The handle 120 can include a housing 145 and an actuation portion 146. In use, the actuation portion 146 can be operated to deflect the distal end portion 132 of the catheter shaft 122 to facilitate positioning the ablation electrode 124 into contact with tissue at a treatment site. The handle 120 can include a fluid line connector 148 (e.g., a luer connector) and an electrical connector 149. The fluid line 115 can be connectable to the fluid line connector 148 and, in use, irrigation fluid (e.g., saline) can be delivered from the irrigation pump 114 to the catheter 104 where, as described in further detail below, the irrigation fluid is ultimately deliverable through the irrigation holes 134 of the irrigation element 128 to the inner portion 136 of the ablation electrode 124. The extension cable 106 is connectable to the electrical connector 149. In use, electrical energy can be delivered from the generator 116 to the catheter 104 where, as described in further detail below, the electrical energy is ultimately deliverable to the ablation electrode 124 to ablate tissue in contact with the outer portion 138 of the ablation electrode 124.

The handle 120 can be attached to the proximal end portion 130 of the catheter shaft 122 through any of various techniques, including one or more of adhesive bonds, thermal bonds, and mechanical connections.

The catheter shaft 122 defines a lumen 151 extending from the proximal end portion 130 of the catheter shaft 122 to the distal end portion 132 of the catheter shaft 122. The lumen 151 can be in fluid communication with the irrigation pump 114, via the fluid line 115 and the fluid line connector 148 of the handle 120, such that irrigation fluid can be pumped from the irrigation pump 114 to the irrigation holes 134 defined by the irrigation element 128. The catheter shaft 122 can also, or instead, include electrical wires (such as any one or more of the wires 117 shown in FIG. 1) extending along the catheter shaft 122 to carry signals between the sensors 126 and the catheter interface unit 108 and to carry electrical power from the generator 116 to the ablation electrode 124.

The catheter shaft 122 can be formed of any of various different biocompatible materials that provide the catheter shaft 122 with sufficient sturdiness and flexibility to allow the catheter shaft 122 to be navigated through blood vessels of a patient. Examples of suitable materials from which the catheter shaft 122 can be formed include polyether block amides (e.g., Pebax®, available from Arkema of Colombes, France), nylon, polyurethane, Pellethane® (available from The Lubrizol Corporation of Wickliffe, Ohio), and silicone. In certain implementations, the catheter shaft 122 includes multiple different materials along its length. The materials can, for example, be selected to provide the catheter shaft 122 with increased flexibility at the distal end, when compared to the proximal. The catheter shaft 122 can also, or instead, include a tubular braided element that provides torsional stiffness while maintaining bending flexibility to one or more regions of the catheter shaft 122. Further, or in the alternative, the shaft material can include radiopaque agents such as barium sulfate or bismuth, to facilitate fluoroscopic visualization.

The catheter shaft 122 can further include pull wires (not shown) mechanically coupled (e.g., via a ring secured to the catheter shaft 122) to the distal end portion 132 of the catheter shaft 122 and mechanically coupled to the actuation portion 146 of the handle 120, as is well known in the art. During use, tension may be applied to the wires to deflect the distal end portion 132 of the catheter shaft 122 to steer the catheter shaft 122 toward a treatment site.

The irrigation element 128 can include a stem 154 and a bulb 156. The stem 154 can be coupled to the distal end portion 132 of the catheter shaft 122 in fluid communication with the lumen 151 of the catheter shaft 122 and, ultimately, with the irrigation pump 114. The bulb 156 defines the irrigation holes 134 and is in fluid communication with the stem 154. Accordingly, irrigation fluid can pass through the lumen 151, through the stem 154, and can exit the irrigation element 128 through the irrigation holes 134 defined by the bulb 156.

The stem 154 can be substantially rigid and extend from the distal end portion 132 of the catheter shaft 122 in a direction having a distal component and/or a radial component. For example, a radial extent of the stem 154 can direct irrigation fluid from an off-center position of the lumen 151 to a position along a center axis defined by the catheter shaft 122. Additionally, or alternatively, a distal extent of the stem 154 can facilitate clearance of the catheter shaft 122 such that a portion of the irrigation holes 134 directed in the proximal direction have a substantially unobstructed path to a portion of the inner portion 136 of the ablation electrode 124 that is proximal to the irrigation element 128. Thus, more generally, it should be understood that the size and shape of one or more of the stem 154, the bulb 156, and the irrigation holes 134 can be varied to achieve desired directionality of the irrigation fluid toward the inner portion 136 of the ablation electrode 124.

The bulb 156 can be substantially rigid and, in certain implementations, formed of the same material as the stem 154. Additionally, or alternatively, the bulb 156 can be substantially spherical to facilitate directing irrigation fluid toward substantially the entire inner portion 136 of the ablation electrode 124. It should be appreciated, however, that the bulb 156 can be any of various different shapes that facilitate multi-directional dispersion of irrigation fluid toward the inner portion 136 of the ablation electrode 124.

In certain implementations, the irrigation holes 134 can be spaced circumferentially and axially along the irrigation element. For example, the irrigation holes 134 can be spatially distributed along the bulb 156 with at least a portion of the irrigation holes 134 arranged to direct irrigation fluid in a distal direction with respect to the ablation electrode 124 and at least a portion of the irrigation holes 134 arranged to direct irrigation fluid in a proximal direction with respect to the ablation electrode 124. More generally, the irrigation holes 134 can be distributed to produce a relatively uniform dispersion of irrigation fluid along the inner portion 136 of the ablation electrode 124 enveloping the irrigation element 128.

The overall radial extent of the irrigation element 128 can be less than the outer diameter of the catheter shaft 122. For example, the irrigation element 128 can remain in the same orientation in a delivery configuration of the catheter 104 to the treatment and during treatment at the treatment site while, as described in further detail below, the ablation electrode 124 expands from a compressed state during delivery to an expanded state during treatment at the treatment site. As also described in further detail below, the fixed orientation of the irrigation element 128 can facilitate using the irrigation element 128 to act as a sensor or to carry a sensor. For example, a sensor can be added to the irrigation element 128 to act as a sensor, in cooperation with the sensors 126 such that the sensor on the irrigation element 128 can act as a center electrode and the sensors 126 can act as surface electrodes, as described in greater detail below.

While the irrigation element 128 can extend distal to the catheter shaft 122, distal extent of the irrigation element 128 can be limited by the inner portion 136 of the ablation electrode 124. For example, the irrigation element 128 can be spaced relative to the inner portion 136 of the ablation electrode 124 such that the irrigation holes 134 direct irrigation fluid toward the inner portion 136 of the ablation electrode 124 in an expanded state. In particular, given that the deformable portion 142 of the ablation electrode 124 is intended to contact tissue during ablation, the irrigation holes 134 can be oriented toward the deformable portion 142 of the ablation electrode 124 to direct fluid toward the inner portion 136 of the ablation electrode 124 along the deformable portion 142 in contact with the tissue. Directing the irrigation fluid toward the deformable portion 142 of the ablation electrode 124 in this way can, for example, reduce the likelihood of unintended tissue damage resulting from the ablation treatment.

Figure 5:
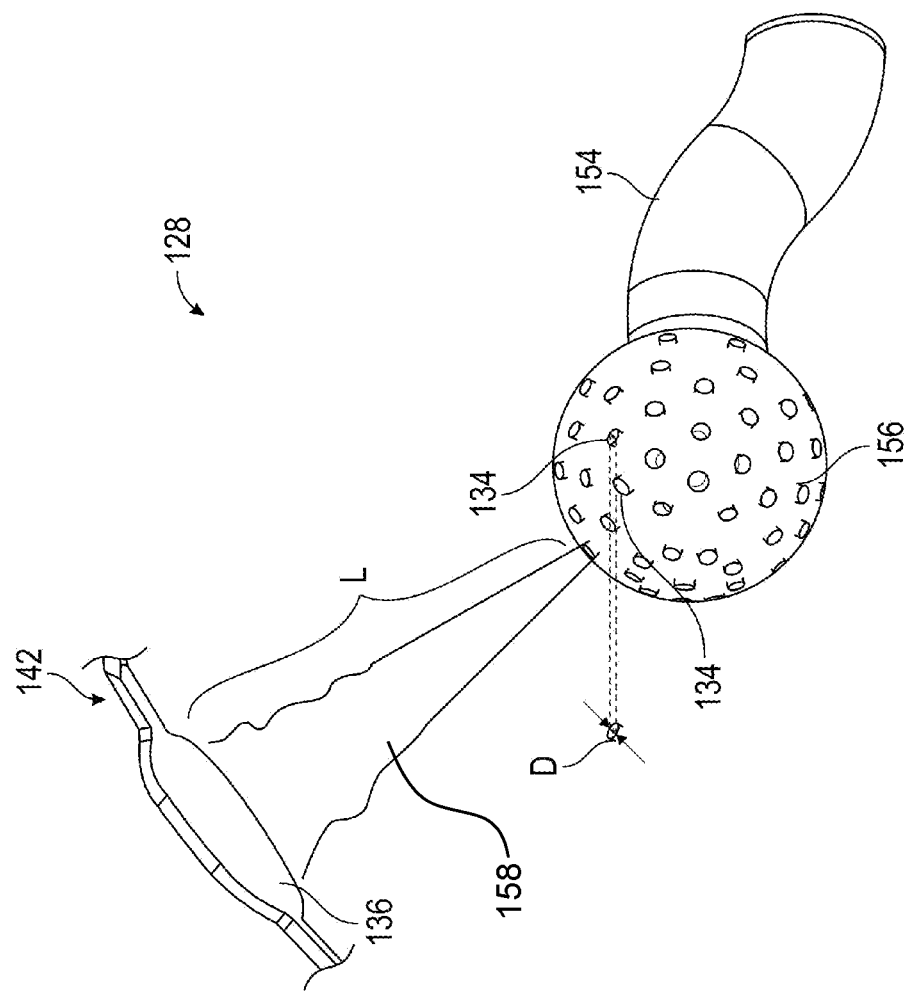
FIG. 5 is a schematic representation of a jet of irrigation fluid moving from an irrigation element to an inner portion of an ablation electrode of the catheter of FIG. 2.
Figure 6:
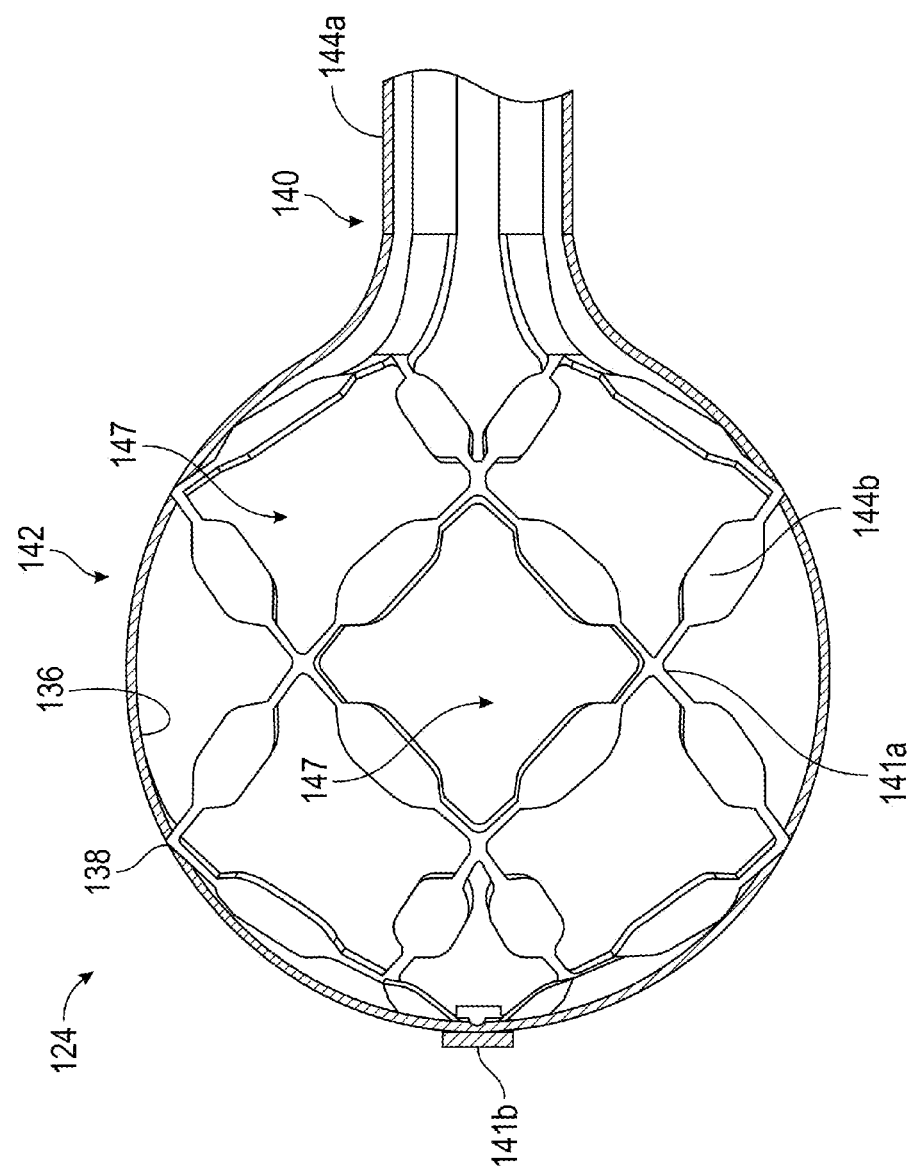
FIG. 6 is a side view of an ablation electrode of the ablation system of FIG. 1.
Figure 7:
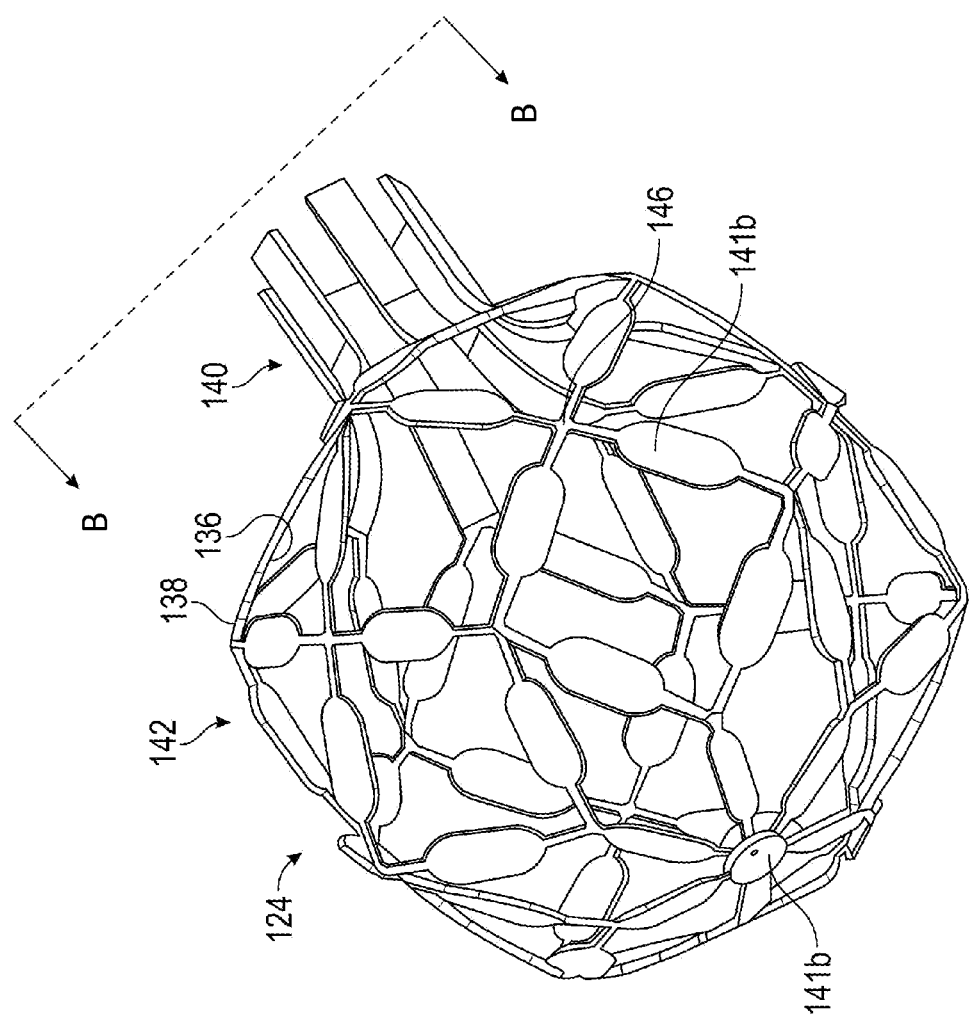
FIG. 7 is a perspective view of the ablation electrode of the ablation system of FIG. 1.
Figure 8:
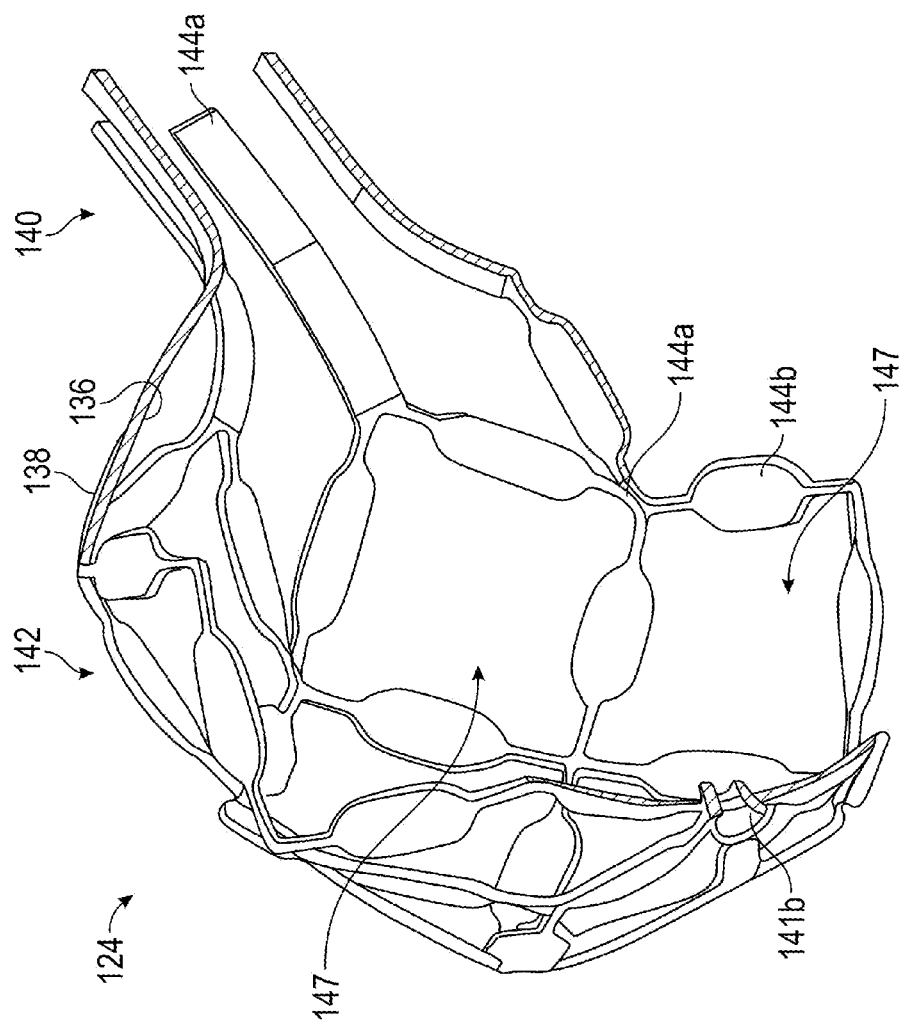
FIG. 8 is a cross-sectional view, taken along line B-B in FIG. 7, of the ablation electrode of the ablation system of FIG. 1.

Referring now to FIG. 5, a schematic representation of a jet 158 of irrigation fluid exiting one of the irrigation holes 134 and moving toward the inner portion 136 of the ablation electrode 124 is shown just prior to impact between the jet 158 and the inner portion 136. A distance "L" is a perpendicular distance between the irrigation hole 134 and the inner portion 136 of the ablation electrode 124 when the ablation electrode 124 is in an undeformed state (e.g., in the absence of an external force applied to the ablation electrode 124). For the sake of clarity, a two-dimensional cross-section of a single jet is shown. However, it should be understood that, in use, a respective three-dimensional jet issues from each of the irrigation holes 134 and the plurality of jets may interact with one another and/or with the patient's blood, along the distance "L," to create additional turbulence at the inner portion 136 of the ablation electrode 124.

In implementations in which the irrigation holes 134 have a circular cross-section, the ratio of a maximum dimension "D" of each of the irrigation holes 134 to the respective distance "L" between the respective irrigation hole 134 and the inner portion 136 of the ablation electrode 124 can be greater than about 0.02 and less than about 0.2 (e.g., greater than about 0.03 and less than about 0.06). Given other design considerations (e.g., manufacturability of hole sizes of the irrigation holes 134, acceptable pressure drop in the system, the influence of blood flow between the irrigation element 128 and the ablation electrode 124, or a combination thereof), this range of ratios will result in turbulent flow of irrigation fluid at the inner portion 136 of the ablation electrode 124. Without wishing to be bound by theory, it is believed that, as compared to configurations with laminar flow and/or less turbulent flow of irrigation fluid past the inner portion 136 of the ablation electrode 124, the turbulent flow of irrigation fluid moving from the irrigation holes 134 to the inner portion 136 of the ablation electrode 124 results in increased heat transfer, which can reduce unintended tissue damage during ablation.

The size and number of the irrigation holes 134 defined by the irrigation element 128 are selected such that the pressure of irrigation fluid in the irrigation element 128 is sufficient to prevent blood from entering the irrigation holes 134. For example, providing for some margin of variation in pressure of the irrigation fluid, the size and number of the irrigation holes 134 defined by the irrigation element 128 can be selected such that the pressure of the irrigation fluid in the irrigation element 128 is at least about 0.5 psi greater than the pressure of the blood of the patient 102. Further, in implementations in which the irrigation element 128 is expandable (e.g., a balloon), the positive pressure difference between the irrigation fluid within the irrigation element 128 and the blood of the patient 102 can allow the irrigation element 128 to maintain an expanded shape. The size and number of the irrigation holes 134 can be, additionally or alternatively, selected to provide substantially uniform coverage of the irrigation fluid on the deformable portion 142 of the ablation electrode 124.

In certain implementations, the irrigation holes 134 defined by the irrigation element 128 have a total open area of greater than about 0.05 mm$^2$ and less than about 0.5 mm$^2$. In some implementations, the total number of irrigation holes 134 can be greater than about 50 and less than about 250 (e.g., about 200). In implementations in which the irrigation element 128 is substantially rigid (e.g., formed of stainless steel and/or platinum iridium), the irrigation holes 134 can be formed into the irrigation element 128 using any one or more material removal techniques known in the art, examples of which include drilling and the use of a laser. In implementations in which the irrigation element 127 is formed of an elastomer, the irrigation holes 134 can be formed through the use of a laser.

Referring now to FIGS. 1-11, the ablation electrode 124 is a continuous structure that acts as one electrode in the monopolar electrode configuration of the ablation system 100, shown in FIG. 1. It should be appreciated, however, that the ablation electrode 124 can include electrically isolated portions such that the ablation electrode 124 includes two electrodes of a bipolar electrode configuration.

The ablation electrode 124 can have an outer diameter of greater than about 4 mm and less than about 16 mm (e.g., about 8 mm) and, additionally or alternatively, a thickness of greater than about 0.07 mm and less than about 0.25 mm (e.g., about 0.17 mm). In certain implementations, the ablation electrode 124 can have greater than about 50 percent open area and less than about 95 percent open area (e.g., about 80 percent open area). As used herein, the percentage of open area of the ablation electrode 124 should be understood to be the ratio of the area through which fluid can flow from the outer portion 138 of the ablation electrode 124 to the surface area of a convex hull that includes the outer portion 138 of the ablation electrode 124 and the structural elements defining the outer portion 138 of the ablation electrode, with the ratio expressed as a percentage. It should be appreciated that the open area of the ablation electrode 124 can facilitate the flow of irrigation fluid and blood through ablation electrode 124 during treatment. As compared to ablation electrodes that impede the flow of blood, the open area of the ablation electrode 124 can reduce the likelihood of local heating of blood at the treatment site as ablation energy is delivered to the tissue. It should be appreciated that the delivery of irrigation fluid to the inner portion 136 of the ablation electrode 124 can augment the cooling that occurs through the flow of only blood through the open area.

In general, it should be appreciated that the dimensions of the ablation electrode 124, including the dimensions related to the diameter, thickness, and/or open area, can facilitate retraction of the ablation electrode 124. That is, the force required to retract the ablation electrode 124 into a sheath (e.g., at the end of a procedure) are such that the ablation electrode 124 can be retracted by a physician without requiring assistance of a separate mechanism to provide a mechanical advantage. Further, or instead, the dimensions of the ablation electrode 124 can facilitate adequate expansion of the electrode 124. For example, in instances in which the electrode 124 is formed of nitinol, the ablation electrode 124 can be dimensioned such that, in the compressed state (e.g., for delivery), strain in the ablation electrode 124 is less than about ten percent. As a more general example, the ablation electrode 124 can be dimensioned such that the ablation electrode 124 is compressible to a size suitable for delivery (e.g., through an 8 French sheath) using a force that avoids, or at least limits, plastic deformation of the material of the ablation electrode 124. It should be appreciated that avoiding, or at least limiting, plastic deformation in this way can facilitate expansion of the ablation electrode 124 in a predictable manner (e.g., to a full extent) in the absence of an applied force.

The coupling portion 140 of the ablation electrode 124 can be directly or indirectly mechanically coupled to the catheter shaft 122. For example, the coupling portion 140 can include struts 144a directly coupled to the catheter shaft 122 or coupled to a transition part coupled to the catheter shaft 122. Each strut 144a can include a portion extending parallel to the catheter shaft 122 with the coupling portion 140 coupled to the catheter shaft 122 along the portion of the strut 144a extending parallel to the catheter shaft 122. Alternatively, or in addition, the coupling portion 140 can include a complete ring directly or indirectly mechanically coupled to the catheter shaft 122.

The coupling portion 140 can be electrically coupled to the generator 116 via one or more of the wires 117 (shown in FIG. 1) and/or other conductive paths extending from the generator 116, along the length of the catheter shaft 122, and to the coupling portion 140. For example, the coupling portion 140 can be fitted into the distal end portion 132 of the catheter shaft 122, connected to wires extending to the generator 116, and potted within an adhesive in the distal end portion 132 of the catheter shaft 122. In use, electrical energy provided at the generator 116 can be delivered to the coupling portion 140 and, thus, to the deformable portion 142 of the ablation electrode 124, where the electrical energy can be delivered to tissue of the patient 102.

The deformable portion 142 of the ablation electrode 124 can include struts 144b mechanically coupled to one another at joints 141a to define collectively a plurality of cells 147 of the ablation electrode 124. Additionally, or alternatively, the struts 144b can be mechanically coupled to one another by a fastener 141b. Accordingly, each end of the struts 144b can be coupled to an end of another strut 144b, to the fastener 141b, or a combination thereof to define the deformable portion 142 of the ablation electrode 124. For example, the struts 144b along the deformable portion 142 of the ablation electrode can be coupled to one another, to the fastener 141b, or to a combination thereof to define a closed shape along the deformable portion 142. Also, or instead, at least some of the struts 144b can be coupled to the struts 144a to transition between the deformable portion 142 and the coupling portion 140 of the ablation electrode 124. In certain implementations, the struts 144b can be coupled to the struts 144a such that the coupling portion 140 defines an open shape along the coupling portion 140 to facilitate, for example, securing the struts 144a to the distal end portion 132 of the catheter shaft 122.

The catheter shaft 122 defines a center axis CL-CL extending from the proximal end portion 130 to the distal end portion 132 of the catheter shaft 122. The cells 147 can have a generally axial orientation relative to the center axis CL-CL. For example, each of the cells 147 can have a respective symmetry plane passing through a distal end of the cell 147, a proximal end of the cell 147, and the center axis CL-CL. Such an orientation can advantageously preferentially expand and contract the cells 147 relative to the center axis CL-CL, which can facilitate compressing the deformable portion 142 of the ablation electrode 124 to a size suitable for delivery to a treatment site.

The center axis CL-CL can, for example, extend through the fastener 141b in the absence of an external force applied to the ablation electrode. Such alignment of the fastener 141b can facilitate, in certain instances, location of the distal end portion 142 of the ablation electrode 124 (e.g., by locating the fastener 141b at a treatment site).

The fastener 141b can be formed of a first material (e.g., a polymer) and the struts 144b can be formed of a second material (e.g., a nitinol) different from the first material. It should be appreciated that the material of the fastener 141b can be selected for a combination of strength and electrical properties suitable for maintaining the struts 144b coupled to one another while achieving a current density distribution suitable for a particular application. The closed shape of the deformable portion 142 can, for example, facilitate the delivery of substantially uniform current density through the ablation electrode 124 in a manner that, as compared to an electrode with an open shape, is less dependent on the orientation of the ablation electrode 124 relative to tissue, as described in greater detail below.

In general, each cell 147 can be defined by at least three struts 144b. Also, or instead, each strut 144b can define a portion of at least two of the cells 147. The inner portion 136 of the ablation electrode 124 can be in fluid communication with the outer portion 138 of the ablation electrode 124 through the plurality of cells 147 such that, in use, irrigation fluid, blood, or a combination thereof can move through the plurality of cells 147 to cool the ablation electrode 124 and tissue in the vicinity of the ablation electrode 124.

At least some of the plurality of cells 147 can be flexible in the axial and lateral directions such that the open framework formed by the plurality of cells 147 along the deformable portion 142 of the ablation electrode 124 is similarly flexible. For example, at least some of the plurality of cells can be substantially diamond-shaped in the uncompressed state of the deformable portion 142 of the ablation electrode 124. As used herein, substantially diamond-shaped includes shapes including a first pair of joints substantially aligned along a first axis and a second pair of joints substantially aligned along a second axis, different from the first axis (e.g., perpendicular to the first axis).

The flexibility of the open framework formed by the plurality of cells 147 along the deformable portion 142 of the ablation electrode 124 can, for example, advantageously resist movement of the deformable portion 142 in contact with tissue during a medical procedure. That is, the deformable portion 142 can deform upon contact with tissue and the deformable portion 142 can engage the tissue through one or more of the cells 147 to resist lateral movement of the deformable portion 142 relative to the tissue. That is, as compared to a closed surface in contact with tissue, the deformable portion 142 will resist unintended movement (e.g., sliding with respect to the tissue) with which it is in contact. It should be appreciated that such resistance to movement can facilitate, for example, more accurate placement of lesions.

The struts 144a, 144b can have dimensions that differ from corresponding dimensions of other ones of the struts 144a, 144b. For example, the struts 144b can have a dimension (e.g., width) that differs from a corresponding dimension of another one of the struts 144b. Varying dimensions of the struts 144a, 144b, for example, can facilitate delivery of substantially uniform current density through the deformable portion 142 of the ablation electrode 124, as described in greater detail below. Additionally, or alternatively, the struts 144a can be wider than the struts 144b to facilitate fixing the struts 144a directly or indirectly to the distal end portion 132 of the catheter shaft 122.

In general, the struts 144b can be dimensioned and arranged relative to one another for delivery of substantially uniform current density through the deformable portion 142 of the ablation electrode 124, as described in greater detail below. By way of non-limiting example, a first set of the struts 144*b* can have a first width, and a second set of the struts 144*b* can have a second width, different from the first width. Continuing with this example, the first set of the struts 144*b* can be axially spaced relative to the second set of the struts 144*b*. Such axial distribution of the material of the struts can be useful, for example, for achieving a desired current density profile (e.g., a substantially uniform current density profile). As another non-limiting example, at least some of the struts 144*b* can have a non-uniform width along a length of the respective strut 144*b* such that the amount of material along a given strut is varied, resulting in an associated distribution in current density. For example, at least some of the struts 144*b* can include a width increasing along the length of the respective strut 144*b* in a direction from a proximal region to a distal region of the ablation electrode 124.

In general, the plurality of cells 147 can be disposed circumferentially and axially about the ablation electrode 124. More specifically, as described in greater detail below, the plurality of cells 147 can be arranged about the ablation electrode 124 (e.g., along the deformable portion 142 of the ablation electrode 124) to facilitate contraction and expansion of the deformable portion 142 and/or to facilitate substantially uniform distribution of current density along the deformable portion 142.

Each cell 147 can be bounded. In particular, as used herein, a bounded cell 147 includes a cell entirely defined by the struts 144*b*, the joints 141*a*, sensors 126 disposed along the struts 144*b* or the joints 141*a*, or a combination thereof. As described in further detail below, the struts 144*b* can be connected to one another at the joints 141*a* as part of a unitary or substantially unitary structure. Additionally, or alternatively, as also described in greater detail below, the struts 144*b* can be connected to one another through welds, fasteners, or other mechanical connections at one or more of the joints 141*a*.

The struts 144*b* can be movable relative to one another through flexing at the joints 141*a*. More specifically, the struts 144*b* can be flexible relative to one another to move the deformable portion 142 between a compressed state, in the presence of an external force, and an uncompressed state, in the absence of the external force. For example, a maximum radial dimension (alternatively referred to herein as a lateral dimension) of the ablation electrode can increase by at least a factor of 2 as the coupled struts 144*b* move relative to one another to transition the ablation electrode 124 from a compressed state, in the presence of external force, to an uncompressed state, in the absence of external force. This ratio of increase in size is achieved through the use of the open framework of cells 147 formed by the struts 144*b*, which makes use of less material than would otherwise be required for a solid shape of the same size. Further, or instead, it should be appreciated that the ratio of the increase in size achieved through the use of the open framework of cells 147 is useful for delivery to a treatment site through an 8 French sheath while also facilitating the formation of large lesions at the treatment site.

Through flexing at the joints 141*a* and associated movement of the struts 144*b*, the deformable portion 142 can be resiliently flexible in an axial direction relative to the catheter shaft 122 and/or in a radial direction relative to the catheter shaft 122. Additionally, or alternatively, the deformable portion 142 can be expandable (e.g., self-expandable) from the compressed state to the uncompressed state. For example, the struts 144*b* can be biased to move in one or more directions away from one another to self-expand the deformable portion 142 from the compressed state to the uncompressed state. In certain instances, the inner portion 136 of the ablation electrode 124 along the deformable portion 142 can be closer in the compressed state than in the uncompressed state to at least a portion of a surface of the irrigation element 128 and, thus, the inner portion 136 of the ablation electrode 124 can move away from at least a portion of the surface of the irrigation element 128 as the deformable portion 142 is expanded from the compressed state to the uncompressed state.

In the uncompressed state, the struts 144*b*, the joints 141*a*, and the cells 147 together can form an open framework having a conductive surface along the deformable portion 142 of the ablation electrode 124. For example, the open framework formed by the struts 144*b*, the joints 141*a*, and the cells 147 can have greater than about 50 percent open area along the outer portion 138 of the ablation electrode 124 when the deformable portion 142 of the ablation electrode 124 is in the uncompressed state. Continuing with this example, in the uncompressed state, the combined open area of the cells 147 can be greater than the combined area of the struts 144*b* and the joints 141*a* along the outer portion 138 of the ablation electrode 124. Further, or instead, at least some of the cells 147 can have a larger area in the uncompressed state of the deformable portion 142 than in the compressed state of the deformable portion 142.

More generally, the open area defined by the cells 147 can have a magnitude and spatial distribution sufficient to receive the struts 144*b* and, optionally the sensors 126, as the deformable portion 142 collapses from the uncompressed state to the compressed state. Accordingly, it should be appreciated that the magnitude of the ratio of the combined open area of the cells 147 to the combined area of the struts 144*b* and the joints 141*a* can, among other things, be useful for varying the degree of expansion of a deformable portion 142 of the ablation electrode 124 relative to a delivery state in which the deformable portion 142 is in a compressed state. That is, the ratio of the combined open area of the cells 147 to the combined area of the struts 144*b* and the joints 141*a* can facilitate minimally invasive delivery (e.g., delivery through an 8 fr sheath) of the ablation electrode 124.

By way of example, a maximum radial dimension of the ablation electrode 124 can increase by at least a factor of 2 as the struts 144*b* move relative to one another to transition the ablation electrode 124 (e.g., the deformable portion 142 of the ablation electrode 124) from a compressed state, in the presence of an external force (e.g., a radial force), to an uncompressed state, in the absence of an external force. Additionally, or alternatively, the struts 144*b* can be movable relative to one another such that a maximum radial dimension of the deformable portion 142, in the uncompressed state, is at least about 20 percent greater than a maximum radial dimension of the catheter shaft 122 (e.g., greater than a maximum radial dimension of the distal end portion 132 of the catheter shaft 122). It should be appreciated that the extension of the deformable portion 142 beyond the maximum radial dimension of the catheter shaft 122 can facilitate creation of a lesion having a large width, as compared to an ablation electrode constrained by a radial dimension of a catheter shaft.

In certain implementations, the ablation electrode 124 has a maximum axial dimension that changes by less than about 33 percent (e.g., about 20 percent) as the struts 144*b* expand (e.g., self-expand) from the uncompressed state to the compressed state upon removal of an external radial force applied to the ablation electrode 124.

At least some of the struts 144b extend in a direction having a circumferential dimensional component with respect to an axis defined by the catheter shaft 122 (e.g., an axis defined by the proximal end portion 130 and the distal end portion 132 of the catheter shaft 122). That is, the struts 144b extending in a direction having a circumferential dimensional component with respect to an axis defined by the catheter shaft 122 are nonparallel to the axis defined by the catheter shaft 122. In some implementations, at least some of the struts 144b include a non-uniform width along a length of the respective strut 144b. Because current density at a given point along the ablation electrode 124 is a function of the amount of surface area at the given point along the ablation electrode 124, the non-uniform width of a given one of the struts 144b can facilitate balancing current density to achieve a target current density profile along the deformable portion 142 of the ablation electrode 124. As described in greater detail below, the circumferential extension and/or the non-uniform width along the length of at least some of the struts 144b can facilitate substantially uniform distribution of current density along the deformable portion 142 during a medical procedure.

While a large surface area of the struts 144b can be advantageous for the delivery of energy to tissue, an upper boundary of the area of the struts 144b can be the geometric configuration that will allow the struts 144b to collapse into the compressed state (e.g., during delivery to the treatment site and/or during contact with tissue at the treatment site) without interfering with one another. Additionally, or alternatively, the struts 144b can be twisted towards the inner portion 136 of the ablation electrode 124. It should be appreciated that, as compared to struts that are not twisted, the twisted struts 144b can be wider while still being collapsible into the compressed state without interfering with one another. Further in addition or further in the alternative, an upper boundary of the area of the struts 144b can be the amount of open area of the deformable portion 142 that will facilitate appropriate heat transfer (e.g., during ablation) at the ablation electrode 124 through the movement of irrigation fluid and/or blood through the deformable portion 142.

As used herein, the uncompressed state of the deformable portion 142 refers to the state of the deformable portion 142 in the absence of a substantial applied force (e.g., an applied force less than about 5 grams). Thus, the uncompressed state of the deformable portion 142 includes a state of the ablation electrode 124 in the absence of external forces. Additionally, the uncompressed state of the deformable portion 142 includes a state of the ablation electrode 124 in which a small applied force (e.g., less an about 5 grams) is present, but is insufficient to create a significant deformation in the deformable portion 142.

In the uncompressed state of the deformable portion 142, the ablation electrode 124 can be bulbous. For example, in the uncompressed state, the deformable portion 142 can be a shape having symmetry in a radial direction and/or an axial direction relative to the catheter shaft 122. For example, in the uncompressed state the deformable portion 142 can be an ellipsoidal shape such as, for example, a substantially spherical shape (e.g., an arrangement of the struts 144b, each strut 144b having a planar shape, relative to one another to approximate a spherical shape). Additionally, or alternatively, in the uncompressed state, the deformable portion 142 can be a symmetric shape (e.g., a substantially ellipsoidal shape or another similar shape contained between a first radius and a perpendicular second radius, the first radius and the second radius within 30 percent of one another in magnitude). Symmetry of the deformable portion 142 can, for example, facilitate symmetric delivery of ablation energy to the tissue in a number of orientations of the deformable portion 142 relative to the tissue being ablated.

At least when the deformable portion 142 is in the uncompressed state, the deformable portion 142 can envelop the irrigation element 128 such that the irrigation element 128 directs irrigation fluid toward the inner portion 136 of the ablation electrode 124. Accordingly, in implementations in which the deformable portion 142 is symmetric, the irrigation element 128 can provide a substantially uniform distribution of irrigation fluid along the inner portion 136 of the ablation electrode 124, as the deformable portion 142 in the uncompressed state envelops the irrigation element 128.

In certain implementations, the largest cross-sectional dimension of the deformable portion 142 in the uncompressed state is larger than the largest cross-sectional dimension of the catheter shaft 122. Thus, because the deformable portion 142 is expandable to extend beyond the catheter shaft 122, the deformable portion 142 can create a lesion that is larger than the largest dimension of the catheter shaft 122 such that the resulting lesions are wider and deeper than lesions created by ablation electrodes that do not expand. For example, in the uncompressed state, the deformable portion 142 can be substantially circular at the largest cross-sectional dimension of the deformable portion, and the catheter shaft 122 can be substantially circular at the largest cross-sectional dimension of the catheter shaft 122. Thus, continuing with this example, the outer diameter of the deformable portion 142 is larger than the outer diameter of the catheter shaft 122.

The compressed state of the ablation electrode 124, as used herein, refers to the state of the ablation electrode in the presence of a force (e.g., a force of about 5 grams or greater) sufficient to cause the deformable portion 142 to flex (e.g., through flexing of one or more of the joints 141a) to a significant extent. Thus, for example, the compressed state of the ablation electrode 124 includes the reduced size profile of the ablation electrode 124 during introduction of the catheter 104 to the treatment site, as described in further detail below. The compressed state of the ablation electrode 124 also includes one or more states of deformation and/or partial deformation resulting from an external force exerted along one or more portions of the deformable portion 142 of the ablation electrode 124 as a result of contact between the deformable portion 142 and tissue at the treatment site.

The compressed state of the ablation electrode 124 can have a predetermined relationship with respect to an applied force. For example, the compressed state of the ablation electrode 124 can have a substantially linear (e.g., within ±10 percent) relationship with applied forces in the range of forces typically applied during an ablation procedure (e.g., about 1 mm deformation in response to 60 grams of force). It should be appreciated that such a predetermined relationship can be useful, for example, for determining the amount of applied force on the ablation electrode 124 based on a measured amount of deformation of the ablation electrode 124. That is, given the predetermined relationship between deformation of the ablation electrode 124 and an amount of an applied force, determining the amount of deformation of the ablation electrode 124 can provide an indication of the amount of force being applied by the ablation electrode 124 on tissue at the treatment site. As such, the determined amount of deformation of the ablation electrode 124 can be used, for example, as feedback to control the amount of force applied to tissue at the treatment site. Methods of determining the amount of deformation of the ablation electrode 124 are described in greater detail below.

Figure 9:
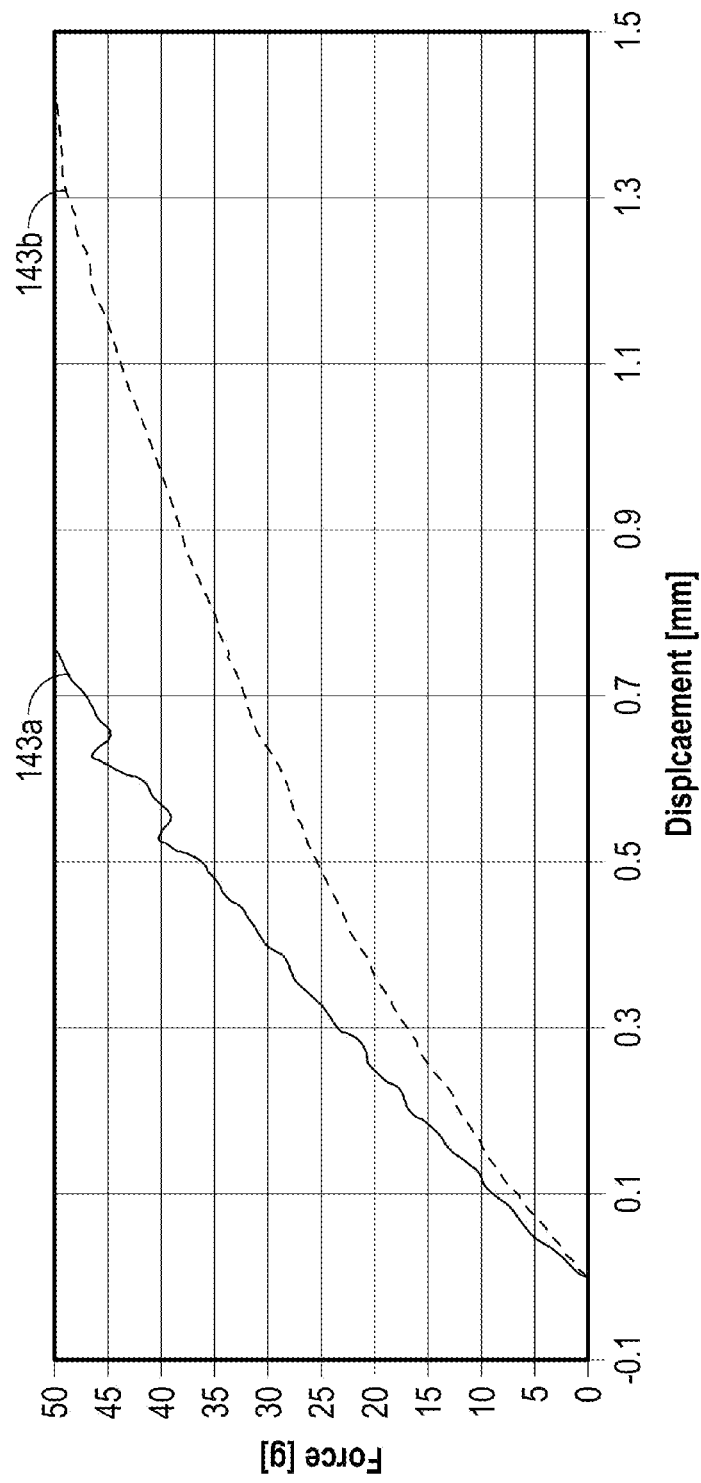
FIG. 9 is an exemplary graph of force as a function of displacement of a deformable portion of the ablation electrode of the ablation system of FIG. 1.

FIG. 9 is a graph of an exemplary relationship between force and displacement for different amounts of force applied to the deformable portion 142 of the ablation electrode 124. The deformable portion 142 of the ablation electrode 124 can have different force-displacement responses, depending on the direction of the force applied to the deformable portion 142 of the ablation electrode 124. For example, as shown in the exemplary relationship in FIG. 9, the deformable portion 142 of the ablation electrode 124 can have an axial force-displacement response 143*a* and a lateral force-displacement response 143*b*. That is, the response of the deformable portion 142 to the application of force can depend on the direction of the applied force. In the specific example of FIG. 9, the deformable portion 142 can be stiffer in the axial direction than in the lateral direction.

In general, the axial force-displacement 143*a* and the lateral force-displacement response 143*b* can be reproducible and, thus, the amount of force applied to the deformable portion 142 of the ablation electrode 124 in the axial and/or lateral direction can be reliably determined based on respective displacement of the deformable portion 142. Accordingly, as described in greater detail below, the determined displacement of the deformable portion 142 can be used to determine the amount and direction of force applied to the deformable portion 142. More generally, because the deformable portion 142 is movable between a compressed state and an uncompressed state in a reproducible manner in response to applied force, the deformable portion 142 of the ablation electrode can be useful as a contact force sensor and, thus, can facilitate application of appropriate force during ablation treatment.

In certain implementations, at least a portion of the ablation electrode 124 is radiopaque, with the deformable portion 142 observable through the use of fluoroscopy or other similar visualization techniques. For example, the deformable portion 142 of the ablation electrode 124 can be radiopaque such that fluoroscopy can provide an indication of the deformation and/or partial deformation of the deformable portion 142 and, therefore, provide an indication of whether the deformable portion 142 is in contact with tissue.

A material for forming the ablation electrode 124 can include nitinol, which is weakly radiopaque and is repeatably and reliably flexible between a compressed state and an uncompressed state. Additionally, or alternatively, the material for forming the ablation electrode 124 can be coated with one or more of gold or tantalum. Thus, continuing with this example, the deformable portion 142 of the ablation electrode 124 (e.g., the struts 144*b*) can be formed of nitinol, either alone or coated, such that ablation energy is delivered through the nitinol forming the deformable portion 142 for delivery to tissue to create lesions.

As described in further detail below, the deformation and/or partial deformation of the deformable portion 142 in the compressed state can be additionally, or alternatively, detected by the sensors 126 to provide feedback regarding the extent and direction of contact between the deformable portion 142 of the ablation electrode 124 and the tissue at the treatment site.

Figure 10:
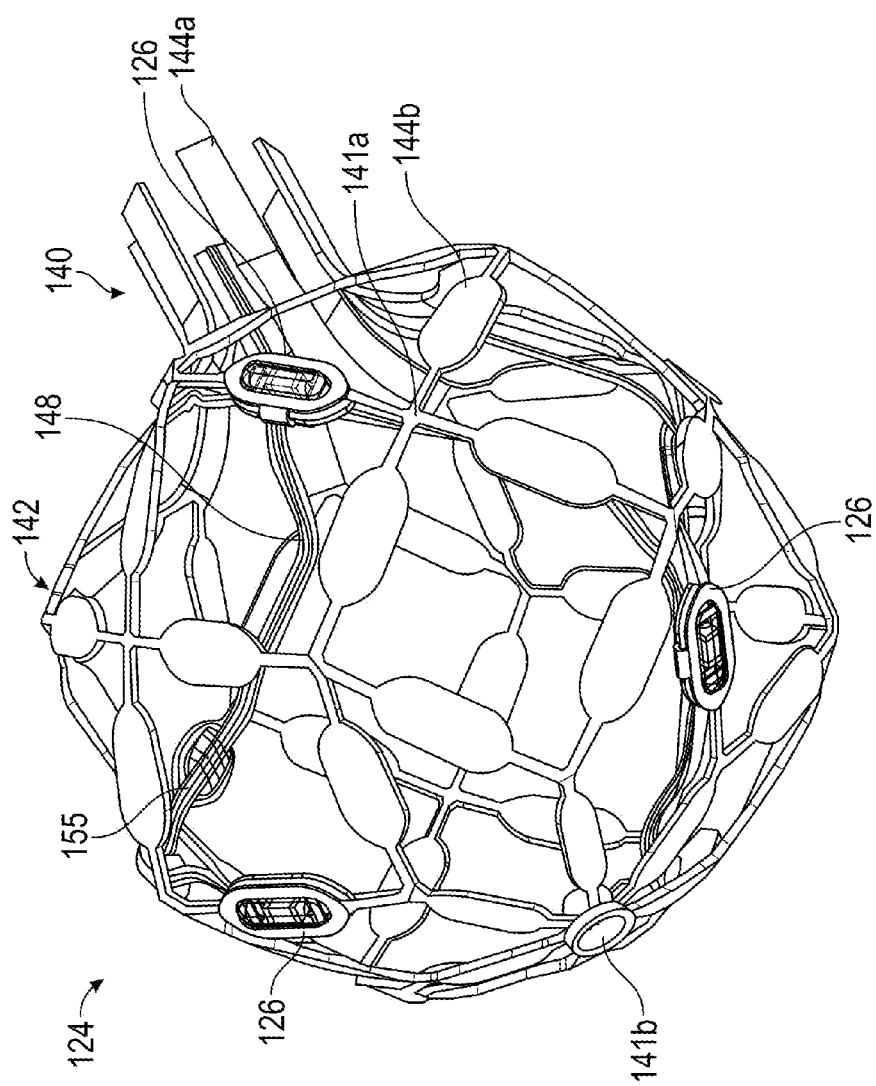
FIG. 10 is a perspective view of sensors and the ablation electrode of the ablation system of FIG. 1, with the sensors shown mounted to the ablation electrode.
Figure 11:
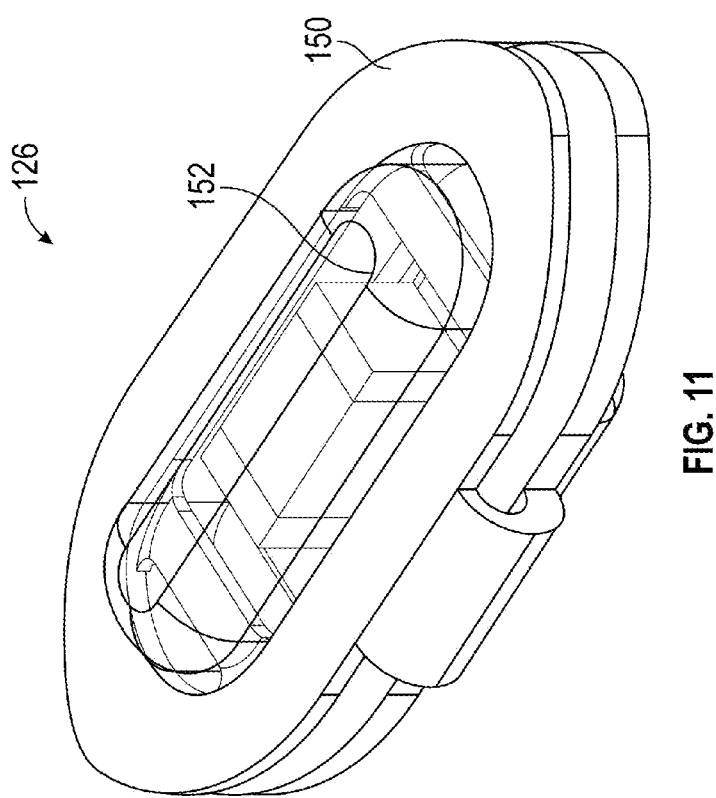
FIG. 11 is a perspective view of a sensor of the ablation system of FIG. 1.

Referring now to FIGS. 10 and 11, the sensors 126 can be mounted along the deformable portion 142 of the ablation electrode 124. Each sensor 126 can be electrically insulated from the ablation electrode 124 and mounted on one of the struts 144*b* of the deformable portion 142. For example, each sensor 126 can be mounted to the deformable portion 142 using a compliant adhesive (e.g., a room temperature vulcanized (RTV) silicone), any of various different mechanical retaining features (e.g., tabs) between the sensor 126 and the ablation electrode 124, and/or molding or overmolding of the sensor 126 to the ablation electrode 124. Because the struts 144*b* do not undergo significant flexing as the deformable portion 142 moves between the compressed state and the uncompressed state, mounting the sensors 126 on the struts 144*b* can reduce physical strain on the sensors 126, as compared to mounting the sensors 126 on sections of the deformable portion 142 that experience larger amounts of flexing as the deformable portion 142 moves between the compressed state and the uncompressed state.

Wires 148 extend from each sensor 126, along the inner portion 136 of the ablation electrode 124, and into the catheter shaft 122 (FIG. 2). The wires 148 are in electrical communication with the catheter interface unit 108 (FIG. 1) such that, as described in further detail below, each sensor 126 can send electrical signals to and receive electrical signals from the catheter interface unit 108 during use.

In general, the sensors 126 can be positioned along one or both of the inner portion 136 and the outer portion 138 of the ablation electrode 124. For example, the sensors 126 can extend through a portion of the ablation electrode 124. Such positioning of the sensors through a portion of the ablation electrode 124 can facilitate forming a robust mechanical connection between the sensors 126 and the ablation electrode 124. Additionally, or alternatively, positioning the sensors 126 through a portion of the ablation electrode 124 can facilitate measuring conditions along the outer portion 138 and the inner portion 136 of the ablation electrode 124.

The sensors 126 can be substantially uniformly spaced from one another (e.g., in a circumferential direction and/or in an axial direction) along the deformable portion 142 of the ablation electrode 124 when the deformable portion 142 of the ablation electrode 124 is in an uncompressed state. Such substantially uniform distribution of the sensors 126 can, for example, facilitate determining an accurate deformation and/or temperature profile of the deformable portion 142 during use.

Each sensor 126 can act as an electrode (e.g., a surface electrode) to detect electrical activity of the heart in an area local to the sensor 126 and, further or instead, each sensor 126 can include a flexible printed circuit 150, a thermistor 152 secured between portions of the flexible printed circuit 150, and a termination pad 155 opposite the thermistor 152. As an example, the sensor 126 can be mounted on the deformable portion 142 of the ablation electrode 124 with the thermistor 152 disposed along the outer portion 138 of the deformable portion 142 and the termination pad 155 disposed along the inner portion 136 of the deformable portion 142. In certain instances, the thermistor 152 can be disposed along the outer portion 138 to provide an accurate indication of tissue temperature. A thermally conductive adhesive or other conductive material can be disposed over the thermistor 152 to secure the thermistor 152 to the flexible printed circuit 150.

In some implementations, each sensor 126 can include a radiopaque portion and/or a radiopaque marker. The addition of radiopacity to the sensor 126 can, for example, facilitate visualization (e.g., using fluoroscopy) of the sensor 126 during use. Examples of radiopaque material that can be added to the sensor 126 include: platinum, platinum iridium, gold, radiopaque ink, and combinations thereof. The radiopaque material can be added in any pattern that may facilitate visualization of the radiopaque material such as, for example, a dot and/or a ring.

In certain implementations, each sensor 126 can form part of an electrode pair useful for detecting contact between each sensor 126 and tissue. For example, electric energy (e.g., current) can be driven through each sensor 126 and another electrode (e.g., any one or more of the various different electrodes described herein) and a change in a measured signal (e.g., voltage or impedance) can be indicative of the presence of tissue. Because the position of the ablation electrode 124 is known, the detection of contact through respective measured signals at the sensors 126 can be useful for determining a shape of the anatomic structure in which the ablation electrode 124 is disposed during the course of a medical procedure.

In use, each sensor 126 can, further or instead, act as an electrode to detect electrical activity in an area of the heart local to the respective sensor 126, with the detected electrical activity forming a basis for an electrogram associated with the respective sensor 126 and, further or instead, can provide lesion feedback. The sensors 126 can be arranged such that electrical activity detected by each sensor 126 can form the basis of unipolar electrograms and/or bipolar electrograms. Additionally, or alternatively, the sensors 126 can cooperate with a center electrode (e.g., an electrode associated with an irrigation element, such as a center electrode 235 in FIGS. 21 and 22 or the irrigation element itself, such as the irrigation element 128 in FIG. 3) to provide near-unipolar electrograms, as described in greater detail below. It should be appreciated that the sensors 126 and a center electrode can cooperate to provide near-unipolar electrograms in addition, or as an alternative, to any one or more of the various different methods of determining contact, shape, force, and impedance described herein, each of which may include further or alternative cooperation between the sensors 126 and a center electrode.

Figure 12B:
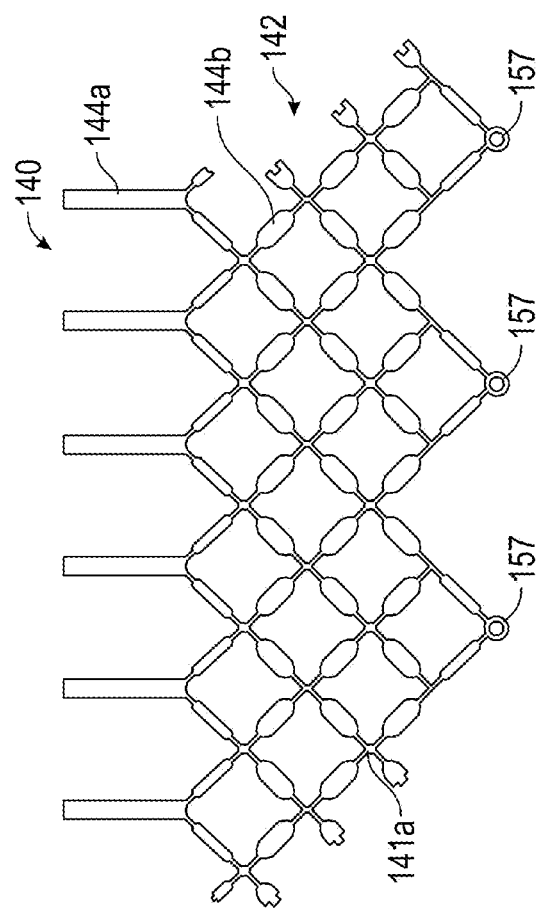

FIGS. 12A-12C are a schematic representation of an exemplary method of making the ablation electrode 124 from a sheet 156 of material.

As shown in FIG. 12A, the sheet 156 of material is flat. As used herein, a flat material includes a material exhibiting flatness within normal manufacturing tolerances associated with the material. The material of the sheet 156 is conductive and, optionally, also radiopaque. For example, the sheet 156 can be nitinol.

The thickness of the sheet 156 can correspond to the thickness of the ablation electrode 124. For example, the thickness of the sheet 156 can be greater than about 0.1 mm and less than about 0.20 mm. In certain implementations, however, the thickness of the sheet 156 can be larger than at least a portion of the thickness of the ablation electrode 124 such that the removal of material from the flat sheet includes removal of material in a thickness direction of the sheet 156. For example, material can be selectively removed in the thickness direction of the sheet 156 to produce the ablation electrode 124 with a variable thickness (e.g., the ablation electrode 124 can be thinner along the joints 141a (FIGS. 6-8) to facilitate flexing).

As shown in FIG. 12B, material can be removed from the sheet 156 to define the open area of the deformable portion 142 and to define the coupling portion 140. In particular, the removal of material along the deformable portion 142 can define the struts 144b and the joints 141a.

The material of the sheet 156 can be removed, for example, by using any of various different subtractive manufacturing processes. As an example, the material of the sheet 156 can be removed using chemical etching (also known as photo etching or photochemical etching) according to any one or more methods that are well known in the art and generally include removing material by selectively exposing the material to an acid to remove the material. Additionally, or alternatively, the material of the sheet 156 can be removed by laser cutting the material. The removal of material can be done to create openings in the sheet 156 and/or to thin selected portions of the sheet 156.

Because the sheet 156 is flat, removing material from the sheet 156 to form the deformable portion 142 can have certain advantages. For example, as compared to removing material from a curved workpiece, removing material from the sheet 156 can facilitate controlling geometric tolerances. Additionally, or alternatively, as compared to removing material from a curved workpiece, removing material from the sheet 156 can facilitate placement of sensors (e.g., while the sheet 156 is flat). In certain implementations, as compared to removing material from a curved workpiece, removing material from the sheet 156 can reduce, or even eliminate, the need to shape set the sheet 156, as the distal and proximal sections can be put together to form the shape of the ablation electrode 124 (e.g., a substantially spherical shape).

In certain implementations, the material removed from the sheet 156 can define eyelets 157 disposed at one end of at least a portion of the struts 144b. The eyelets 157 can be, for example, defined at the intersection of two or more of the struts 144b.

In general, the material forming the ablation electrode 124 can be processed at any of various different stages of fabrication of the ablation electrode 124. For example, with the material removed from the sheet to define the struts 144a, 144b and the joints 141a as shown in FIG. 12B, one or more surfaces of the material can be electropolished. Such electropolishing can, for example, be useful for smoothing surfaces and/or otherwise producing fine adjustments in the amount of material along the ablation electrode 124.

As shown in FIG. 12C, with the material removed from the sheet 156 to define the struts 144a, 144b and the joints 141a, the sections 158 are bent into proximity with one another and joined to one another to form a unitary three-dimensional structure having the overall shape of the ablation electrode 124. For example, the struts 144b can be bent toward one another and the fastener 141b can couple the portion of the struts 144b to one another at the eyelets 157, thus defining a closed distal end of the deformable portion 142 of the ablation electrode 124. With the deformable portion 142 defined, the fastener 141b can be at a distalmost portion of the deformable portion 142.

In certain implementations, the fastener 141b can be a rivet. In such implementations, the eyelets 157 can be, for example, aligned with one another such that the fastener 141b passes through the aligned eyelets 157 to hold them together through force exerted on the eyelets 157 by the fastener 141b. Additionally, or alternatively, a secondary operation such as welding can secure the fastener 141b to the struts 144b at the eyelets 157.

Referring now to FIGS. 13A-E, to perform a cardiac ablation treatment, the distal end portion 132 of the catheter shaft 122 and, thus, the ablation electrode 124 can be first introduced into the patient, typically via a femoral vein or artery. FIGS. 13A-E schematically illustrate a series of steps carried out to introduce the ablation electrode 124 into the patient.

In a first step, shown in FIG. 13A, an introducer sheath 162 is positioned within a blood vessel of the patient (e.g., the femoral artery of the patient) and the ablation electrode 124 is positioned for insertion into the introducer sheath 162.

In a second step, shown in FIG. 13B, the user grasps the handle 120 of the catheter 104 and distally advances an insertion sheath 164 along the catheter shaft 122 until the insertion sheath 164 surrounds the ablation electrode 124. As the insertion sheath 164 is advanced over the ablation electrode 124, the ablation electrode 124 collapses to a diameter capable of being inserted into the introducer sheath 162.

In a third step, shown in FIG. 13C, the user inserts the insertion sheath 164 (containing the ablation electrode 124) into the introducer sheath 162 and distally advances the catheter 104.

In a fourth step, shown in FIG. 13D, after positioning the ablation electrode 124 within the introducer sheath 162, the ablation electrode 124 is advanced out of the insertion sheath 164 that is then left surrounding the proximal end portion 130 of the catheter shaft 122 throughout the remainder of the treatment.

In a fifth step, shown in FIG. 13E, the catheter 104 is advanced through the introducer sheath 162 and the patient's vasculature until the ablation electrode 124 reaches the treatment site in the heart of the patient. As the ablation electrode 124 is extended distally beyond the introducer sheath 162, the ablation electrode 124 can expand to the uncompressed state.

Because the ablation electrode 124 is collapsible, the introducer sheath 162 can have a small diameter that can be inserted through a correspondingly small insertion site. In general, small insertion sites are desirable for reducing the likelihood of infection and/or reducing the amount of time required for healing. In certain implementations, the introducer sheath 162 can have an 8 French diameter, and the deformable portion 142 (FIG. 3) of the ablation electrode 124 can be collapsible to a size deliverable through the introducer sheath 162 of this size. In some implementations, the irrigation element 128 is additionally collapsible to a size smaller than the size of the ablation electrode 124 such that the irrigation element 128 and the ablation electrode 124 are, together, deliverable through the introducer sheath 162 of this size.

Figure 14A:
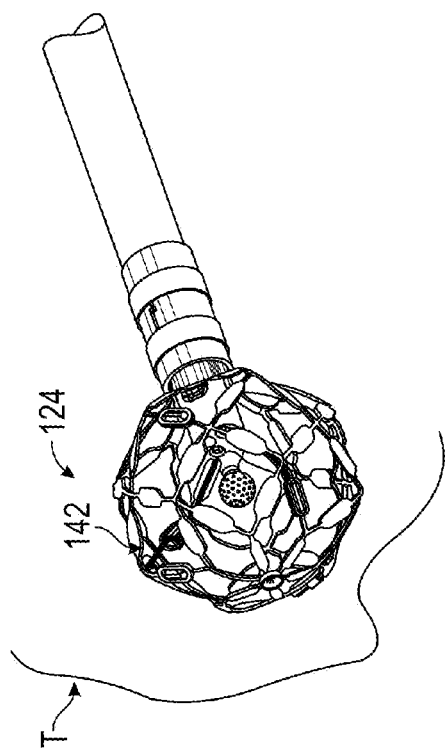
Figure 14C:
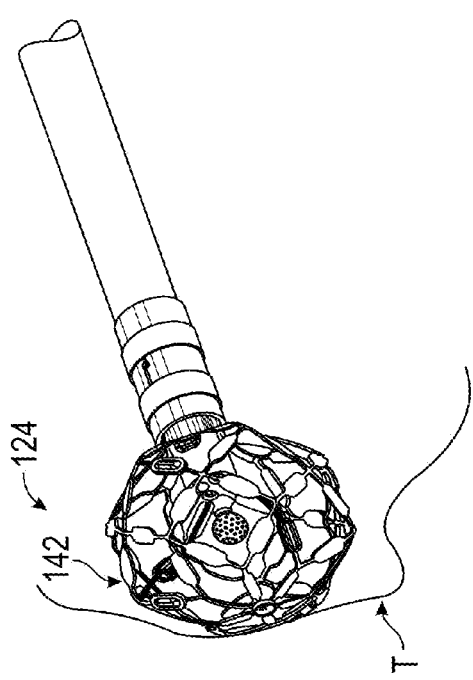

FIGS. 14A-C schematically represent an exemplary method of positioning the deformable portion 142 of the ablation electrode 124 into contact with tissue "T" at the treatment site. It should be appreciated that, because the delivery of ablation energy to the tissue "T" at the treatment site is enhanced by contact between the ablation electrode 124 and the tissue "T," such contact is established prior to delivery of ablation energy.

In a first step, shown in FIG. 14A, the deformable portion 142 of the ablation electrode 124 is away from the tissue "T" and, thus, in an uncompressed state. In certain instances, this uncompressed state is observable through fluoroscopy. That is, the shape of the deformable portion 142 can be observed in the uncompressed state.

In a second step, shown in FIG. 14B, the deformable portion 142 of the ablation electrode 124 makes initial contact with the tissue "T." Depending on the nature of the contact between the tissue "T" and the deformable portion 142 of the ablation electrode 124, deformation of the deformable portion 142 may or may not be observable through fluoroscopy alone. For example, the contact force on the deformable portion 142 may be insufficient to compress the deformable portion 142 to an extent observable using fluoroscopy. Additionally, or alternatively, the contact may not be observable, or may be difficult to observe, in the direction of observation provided by fluoroscopy.

In a third step, shown in FIG. 14C, the deformable portion 142 of the ablation electrode 124 is moved further into contact with the tissue "T" such that sufficient contact is established between the deformable portion 142 and the tissue "T" to deform the deformable portion 142. While such deformation may be observable using fluoroscopy, the degree and/or direction of the deformation is not readily determined using fluoroscopy alone. Further, as is also the case with initial contact, the contact and/or degree of contact may not be observable, or may be difficult to observe, in the direction of observation provided by fluoroscopy. Accordingly, as described in greater detail below, determining apposition of the deformable portion 142 to the tissue "T" can, additionally or alternatively, include sensing the position of the deformable portion 142 based on signals received from the sensors 126.

Referring again to FIGS. 1 and 3, the sensors 126 can be used to determine the shape of the deformable portion 142 of the ablation electrode 124 and, thus, determine whether and to what extent certain regions of the deformable portion 142 are in contact with the tissue "T." It should be appreciated, however, that the sensing methods described herein can be carried out using the sensors 126, alone or in combination with another electrode, such as an electrode carried on an irrigation element, as described in greater detail below.

For example, the processing unit 109a can control the generator 116 and/or another electrical power source to drive an electrical signal between any number and combination of electrode pairs formed by any combination of electrodes associated with the ablation electrode 124, and the processing unit 109a can receive a signal (e.g., a signal indicative of voltage) from another electrode pair or the same electrode pair. For example, the processing unit 109a can control the generator 116 to drive one or more of the sensors 126, the ablation electrode 124, the irrigation element 128, and a center electrode (e.g., a center electrode 235 shown in FIGS. 21 and 22). Additionally, or alternatively, multiple pairs can be driven in a multiplexed manner using time division, frequency division, code division, or combinations thereof. The processing unit 109a can also, or instead, receive one or more measured electrical signals from one or more of the sensors 126, the ablation electrode 124, the irrigation element 128, and a center electrode (e.g., the center electrode 235 shown in FIGS. 21 and 22) through which the electrical signal is not being driven. The driven electrical signal can be any of various, different forms, including, for example, a prescribed current or a prescribed voltage. In certain implementations, the driven electrical signal is an 8 kHz alternating current applied between one of the sensors 126 and the irrigation element 128.

In an exemplary method, the impedance detected by an electrode pair can be detected (e.g., as a signal received by the processing unit 109a) when an electrical signal is driven through the electrode pair. The impedance detected for various electrode pairs can be compared to one another and relative distances between the members of each electrode pair determined. For example, if the sensors 126 are identical, each sensor 126 can be driven as part of a respective electrode pair including the irrigation element 128. For each such electrode pair, the measured impedance between the electrode pair can be indicative of relative distance between the particular sensor 126 and the irrigation element 128 forming the respective electrode pair. In implementations in which the irrigation element 128 is stationary while electrical signals are driven through the electrode pairs, the relative distance between each sensor 126 and the irrigation element 128 can be further indicative of relative distance between each sensor 126 and each of the other sensors 126. In general, driven electrode pairs with lower measured impedance are closer to one another than those driven electrode pairs with higher measured impedance. In certain instances, electrodes associated with the ablation electrode 124 (e.g., one or more of the sensors 126) that are not being driven can be measured to determine additional information regarding the position of the driven current pair.

The measurements received by the processing unit 109a and associated with the driven current pairs alone, or in combination with the measurements at the sensors 126 that are not being driven, can be fit to a model and/or compared to a look-up table to determine displacement of the deformable portion 142 of the ablation electrode 124. For example, the determined displacement of the deformable portion 142 of the ablation electrode 124 can include displacement in at least one of an axial direction or a lateral (radial) direction. It should be appreciated that, because of the spatial separation of the current pairs in three dimensions, the determined displacement of the deformable portion 142 of the ablation electrode 124 can be in more than one direction (e.g., an axial direction, a lateral direction, and combinations thereof). Additionally, or alternatively, the determined displacement of the deformable portion 142 of the ablation electrode 124 can correspond to a three-dimensional shape of the deformable portion 142 of the ablation electrode 124.

Based on the determined displacement of the deformable portion 142 of the ablation electrode 124, the processing unit 109a can send an indication of the shape of the deformable portion 142 of the ablation electrode 124 to the graphical user interface 110. Such an indication of the shape of the deformable portion 142 can include, for example, a graphical representation of the shape of the deformable portion 142 corresponding to the determined deformation.

In implementations in which the force-displacement response of the deformable portion 142 is reproducible (e.g., as shown in FIG. 9), the processing unit 109a can determine force applied to the deformable portion 142 based on the determined displacement of the deformable portion 142. For example, using a lookup table, a curve fit, or other predetermined relationship, the processing unit 109a can determine the direction and magnitude of force applied to the deformable portion 142 based on the magnitude and direction of the displacement of the deformable portion 142, as determined according to any one or more of the methods of determining displacement described herein. It should be appreciated, therefore, that the reproducible relationship between force and displacement along the deformable portion 142, coupled with the ability to determine displacement using the sensors 126 disposed along the deformable portion 142, can facilitate determining whether an appropriate amount of force is being applied during an ablation treatment and, additionally or alternatively, can facilitate determining appropriate energy and cooling dosing for lesion formation.

Figure 15A:
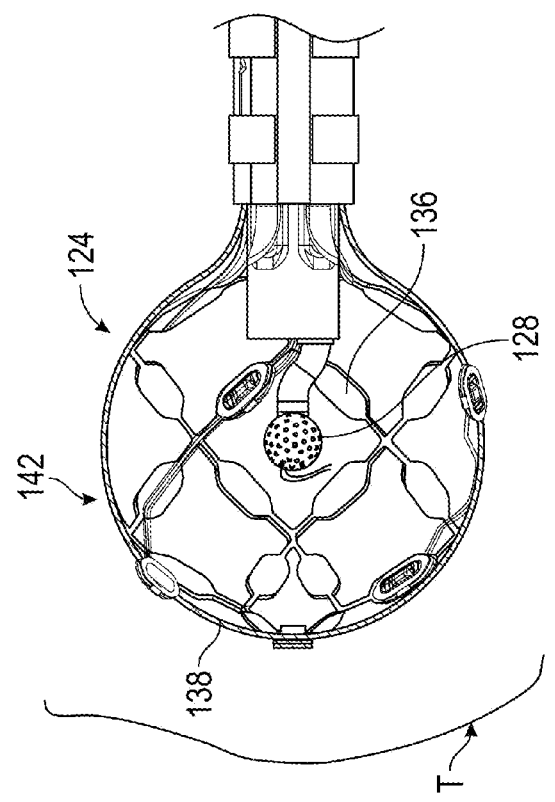
FIGS. 15A-B are schematic representations of a method of irrigating the ablation electrode of the ablation system of FIG. 1.
Figure 15B:
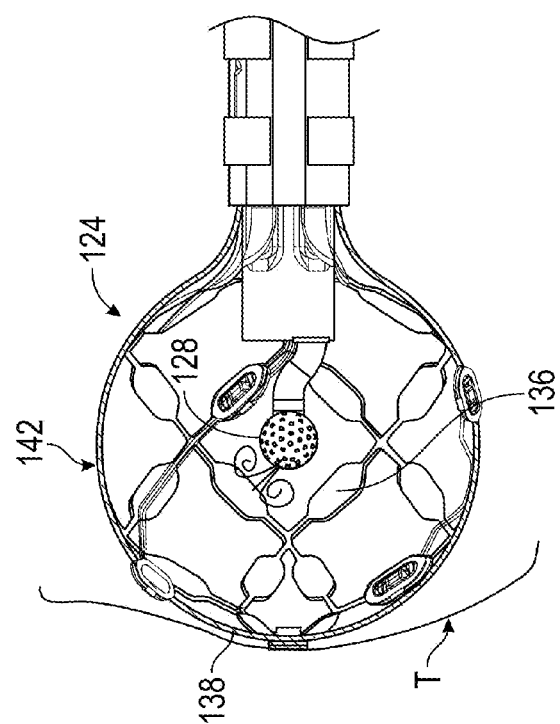

FIGS. 15A-B schematically represent an exemplary method of cooling the ablation electrode 124 at the treatment site with irrigation fluid from the irrigation element 128. For the sake of clarity of illustration, a single jet of irrigation fluid is shown. It should be appreciated, however, that a plurality of jets issue from the irrigation element 128 during use. In certain implementations, the irrigation fluid is substantially uniformly directed to the inner portion 136 of the ablation electrode 124. Additionally, or alternatively, a portion of the irrigation fluid can be directed in a direction distal to the irrigation element 128 and a portion of the irrigation fluid can be directed in a direction proximal to the irrigation element 128.

In a first step, shown in FIG. 15A, the ablation electrode 124 is positioned at the treatment site with the outer portion 138 disposed toward tissue. A baseline flow of irrigation fluid is delivered to the irrigation element 128 prior to delivery of ablation energy to the ablation electrode 124. The baseline flow of irrigation fluid can be, for example, about 0.5 psi above the patient's blood pressure to reduce the likelihood that blood will enter the irrigation element 128 and clot. Further, as compared to always delivering irrigation fluid at a higher pressure, the delivery of this lower pressure of irrigation fluid when ablation energy is not being delivered to the ablation electrode 124 can reduce the amount of irrigation fluid delivered to the patient during treatment.

In a second step, shown in FIG. 15B, ablation energy is directed to at least some of the outer portion 138 of the ablation electrode 124 in contact with the tissue "T". As the ablation energy is delivered to the ablation electrode 124, the pressure of the irrigation fluid can be increased, resulting in a higher pressure flow directed from the irrigation element 128 toward the inner portion 136 of the ablation electrode 124. The higher flow of irrigation fluid at the inner portion 136 can result in turbulent flow which, compared to laminar flow, can improve heat transfer away from the ablation electrode 124. For example, each jet of irrigation fluid issuing from the irrigation element 128 can have a Reynolds number above about 2000 (e.g., greater than about 2300) at the inner portion 136 of the ablation electrode 124 when the deformable portion 142 is in the uncompressed state.

While certain embodiments have been described, other embodiments are additionally or alternatively possible.

For example, while forming the deformable portion of an ablation electrode has been described as including removal of material from a flat sheet, other methods of forming a deformable portion of an ablation electrode are additionally or alternatively possible. For example, a deformable portion of an ablation electrode can be formed by removing material (e.g., by laser cutting) from a tube of material (e.g., a tube of nitinol). With the material removed, the tube can be bent into a substantially enclosed shape such as the substantially spherical shapes described herein.

As another example, while the deformable portion of an ablation electrode has been described as being formed by removing material from a unitary structure of material (e.g., from a plate and/or from a tube), other methods of forming a deformable portion of an ablation electrode are additionally or alternatively possible. For example, a deformable portion of an ablation electrode can include a mesh and/or a braid. The mesh material can be, for example, nitinol. It should be appreciated that this mesh and/or braided portion of the ablation electrode can move between a compressed and uncompressed state.

As yet another example, while an ablation electrode has been described as having a deformable portion, along which sensors are disposed for determining displacement of the deformable portion, other configurations for determining displacement are additionally or alternatively possible. For example, a plurality of coils can be disposed along a deformable portion of an ablation electrode. In use, some coils in the plurality can be used to emit a magnetic field while other coils in the plurality can be used to measure the resultant magnetic field. The signals measured can be used to determine displacement of the deformable portion. This determined displacement of the deformable portion can be used, for example, to determine the shape of the deformable portion and, additionally or instead, to determine the force applied to the deformable portion according to any one or more of the methods described herein. Further, or instead, a plurality of ultrasound transducers or other types of image sensors can be disposed along a deformable portion of an ablation electrode, on an irrigation element enveloped by the deformable portion, or a combination thereof. The signals measured by the ultrasound transducers or other types of image sensors can be used to determine displacement of the deformable portion.

As still another example, while the deformable portion of an ablation electrode has been described as being self-expandable from the compressed state to the uncompressed state, the deformable portion of the ablation electrode can be additionally or alternatively expanded and/or contracted through the application of external force. For example, a catheter such as any one or more of the catheters described herein can include a sliding member extending from the handle, though a catheter shaft, and to an ablation electrode. The sliding member can be coupled (e.g., mechanically coupled) to the ablation electrode such that axial movement of the sliding member relative to the catheter shaft can exert compression and/or expansion force on the deformable portion of the ablation electrode. For example, distal movement of the sliding member can push the ablation electrode in a distal direction relative to the catheter shaft such that the deformable portion of the ablation electrode collapses to a compressed state (e.g., for retraction, delivery, or both). In addition, or as an alternative, proximal movement of the sliding member can pull the ablation electrode in a proximal direction relative to the catheter shaft such that the deformable portion of the ablation electrode expands to an uncompressed state (e.g., for the delivery of treatment). In certain implementations, the sliding member can be mechanically coupled to a portion of the handle such that movement of the sliding member can be controlled at the handle. It should be appreciated that the sliding member can be an elongate member (e.g., a wire) that is sufficiently flexible to bend with movement of the shaft while being sufficiently rigid to resist buckling or other types of deformation in response to the force required to move the deformable portion of the ablation electrode.

As yet another example, while the irrigation element has been described as including a substantially rigid stem and bulb configuration, other configurations of the irrigation element are additionally or alternatively possible. For example, referring now to FIG. 16, an irrigation element 128a can include an axial portion 166 and a helical portion 168. The irrigation element 128a can be used in any one or more of the catheters described herein. For example, the irrigation element 128a can be used in addition to or instead of the irrigation element 128, as described with respect to FIGS. 3-5.

The axial portion 166 and the helical portion 168 are in fluid communication with one another and, in certain implementations, with an irrigation lumen defined by the catheter shaft. At least the helical portion 168 and, optionally, the axial portion 166 define a plurality of irrigation holes 134a along at least a portion of the length of the irrigation element 128a. In use, the delivery of irrigation fluid through the irrigation holes 134a can result in an axially, circumferentially, and/or radially distributed pattern. Unless otherwise indicated or made clear from the context, the irrigation element 128a can be used in addition to or instead of the irrigation element 128 (FIG. 3). Thus, for example, it should be understood that the irrigation element 128a can provide substantially uniform cooling along the inner portion 136 of the ablation electrode 124 (FIG. 3).

The irrigation holes 134a can be similar to the irrigation holes 134 defined by the irrigation element 128 (FIG. 3). For example, the irrigation holes 134a can be the same size and shape as the irrigation holes 134 defined by the irrigation element 128. Additionally, or alternatively, the irrigation holes 134a can have the same open area as the irrigation holes 134 defined by the irrigation element 128.

The axial portion 166 of the irrigation element 128 can be coupled to a catheter shaft (e.g., to a distal end portion of the catheter shaft such as the distal end portion 132 of the catheter shaft 122 described with respect to FIGS. 2-4). Additionally, or alternatively, the axial portion 166 can extend distally from the catheter shaft. For example, the axial portion 166 can extend distally from the catheter shaft, along an axis defined by the irrigation lumen.

In general, the helical portion 168 extends in a radial direction away from the axial portion 166. In certain implementations, a maximum radial dimension of the helical portion 168 is less than an outer diameter of the catheter shaft. In such implementations, the helical portion 168 can remain in the same orientation during delivery and use of the catheter (e.g., during any of the delivery and/or use methods described herein). In some implementations, however, the helical portion 168 can be resiliently flexible (e.g., a nitinol tube shape set in a helical configuration) such that the maximum radial extent of the helical portion 168 is less than an outer diameter of the catheter shaft during delivery to the treatment site and expands such that the maximum radial extent of the helical portion 168 is greater than the outer diameter of the catheter shaft in a deployed position. It should be appreciated that, in the deployed position, the helical portion can be positioned closer to the inner surface of an ablation electrode, which can facilitate delivery of irrigation fluid to the inner surface of the ablation electrode.

In addition to extending in a radial direction away from the catheter shaft, the helical portion 168 extends in a circumferential direction relative to the axial portion 166. For example, the helical portion 168 can extend circumferentially about the axial portion 166 through at least one revolution. Such circumferential extension of the helical portion through at least one revolution can facilitate substantially uniform dispersion of irrigation fluid about an inner surface of a substantially spherical ablation electrode enveloping the helical portion 168.

Optionally, the helical portion 168 can further extend in an axial direction relative to the axial portion 166. Thus, as used herein, the helical portion 168 should be understood, in the most general sense, to include any of various different helical patterns that are substantially planar and/or various different helical patterns that extend axially relative to the axial portion 166.

Figure 16:
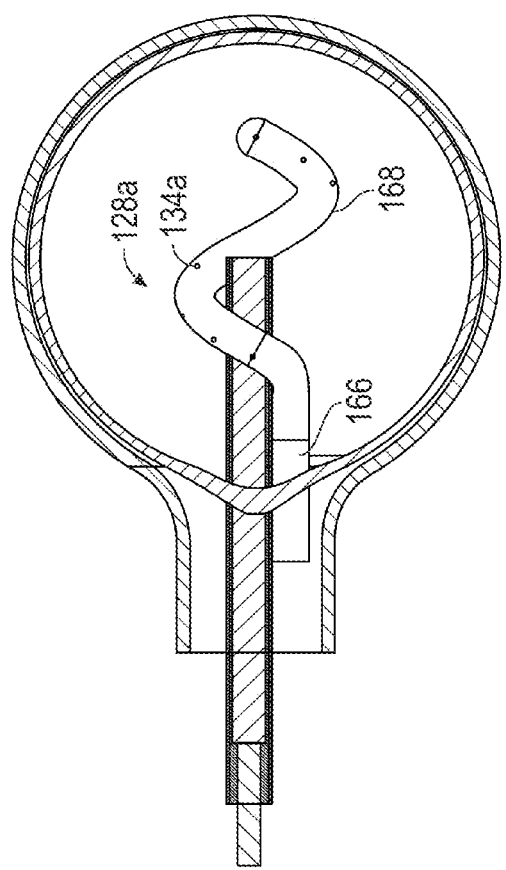
FIG. 16 is a schematic representation of a side view of a helical irrigation element of a catheter of an ablation system.

As another example, while the irrigation element has been described as having a discrete number of uniform irrigation holes, other implementations are additionally or alternatively possible. For example, referring now to FIG. 17, an irrigation element 128b can be a porous membrane defining a plurality of openings 170. In general, the plurality of openings 170 are a property of the material forming the irrigation element 128c and are, therefore, distributed (e.g., non-uniformly distributed and/or uniformly distributed) along the entire surface of the irrigation element 128b. Because the openings 170 are a property of the material forming the irrigation element 128b, the plurality of openings 170 can be substantially smaller than irrigation holes formed in an irrigation element through laser drilling or other similar secondary processes. Unless otherwise indicated or made clear from the context, the irrigation element 128b can be used in addition to or instead of the irrigation element 128 (FIG. 3) and/or the irrigation element 128a (FIG. 16). Thus, for example, it should be understood that the irrigation element 128b can provide substantially uniform cooling along the inner portion 136 of the ablation electrode 124 (FIG. 3).

In certain implementations, the irrigation element 128b can include an arrangement of one or more polymers. Such an arrangement can be porous and/or microporous and, as an example, can be formed of polytetrafluoroethylene (PTFE). In such implementations, the openings 170 can be defined by spaces between polymeric fibers or through the polymeric fibers themselves and are generally distributed along the entire surface of the irrigation element 128b. It should be appreciated that the large number of the openings 170 and the distribution of the openings 170 along the entire surface of the irrigation element 128b can produce a substantially uniform spray of irrigation fluid. Further, the large number of the openings 170 and the distribution of the openings 170 along the entire surface of the irrigation element 128b can facilitate interaction of multiple different fluid jets and, thus, the development of turbulent flow of irrigation fluid.

The size and distribution of the openings 170 defined between or through polymeric fibers can allow the irrigation element 128b to act as a selective filter. For example, because blood molecules are substantially larger than water molecules, the size (e.g., the average size) of the openings 170 can be smaller than blood molecules but larger than water molecules. It should be appreciated that such sizing of the openings 170 can permit egress of irrigation fluid from the irrigation element 128b while preventing ingress and, thus, clotting of blood molecules into the irrigation element 128b.

Figure 17:
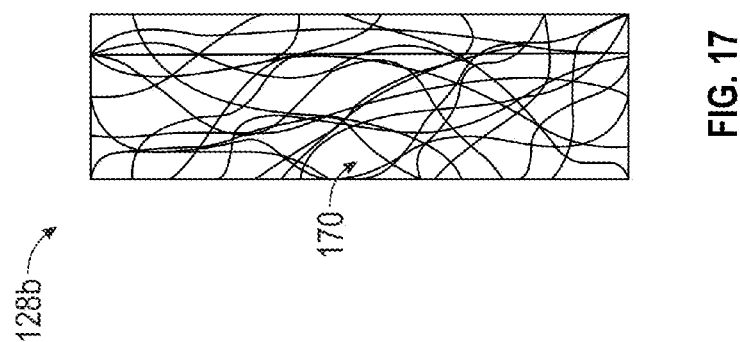
FIG. 17 is a side view of an irrigation element of a catheter of an ablation system, the irrigation element including a porous membrane.

The arrangement of one or more polymers of the irrigation element 128b can include electrospun polytetrafluoroethylene and/or expanded polytetrafluoroethylene (ePTFE). In certain implementations, the arrangement of one or more polymers is nonwoven (as shown in FIG. 17) resulting in the spacing between the fibers being substantially non-uniform such that the openings 170 defined by the spacing between the fibers are of non-uniform size and/or non-uniform distribution. In some implementations, the irrigation element 128b can include a woven or fabric arrangement of polymers through which irrigation fluid can be directed. For example, the fabric can be formed of one or more polymers or other biocompatible materials woven together to form a substantially uniform porous barrier through which, in use, irrigation fluid may pass. Examples of polymers that can be arranged together into a fabric suitable for forming the irrigation element 128c include, but are not limited to, one or more of the following: polyester, polypropylene, nylon, PTFE, and ePTFE.

In some implementations, the irrigation element 128b can include an open cell foam such that the openings 170 are defined by cells of the open cell foam along the surface of the irrigation element 128b. In such implementations, irrigation fluid can move through tortuous paths defined by the open cell foam until the irrigation fluid reaches the openings 170 along the surface of the irrigation element 128b, where the irrigation fluid exits the irrigation element 128b. It should be appreciated that, in such implementations, the openings 170 are distributed along the entire surface of the irrigation element 128b, resulting in spray of irrigation fluid issuing from the irrigation element 128b in a substantially uniform and substantially turbulent pattern.

Figure 18:
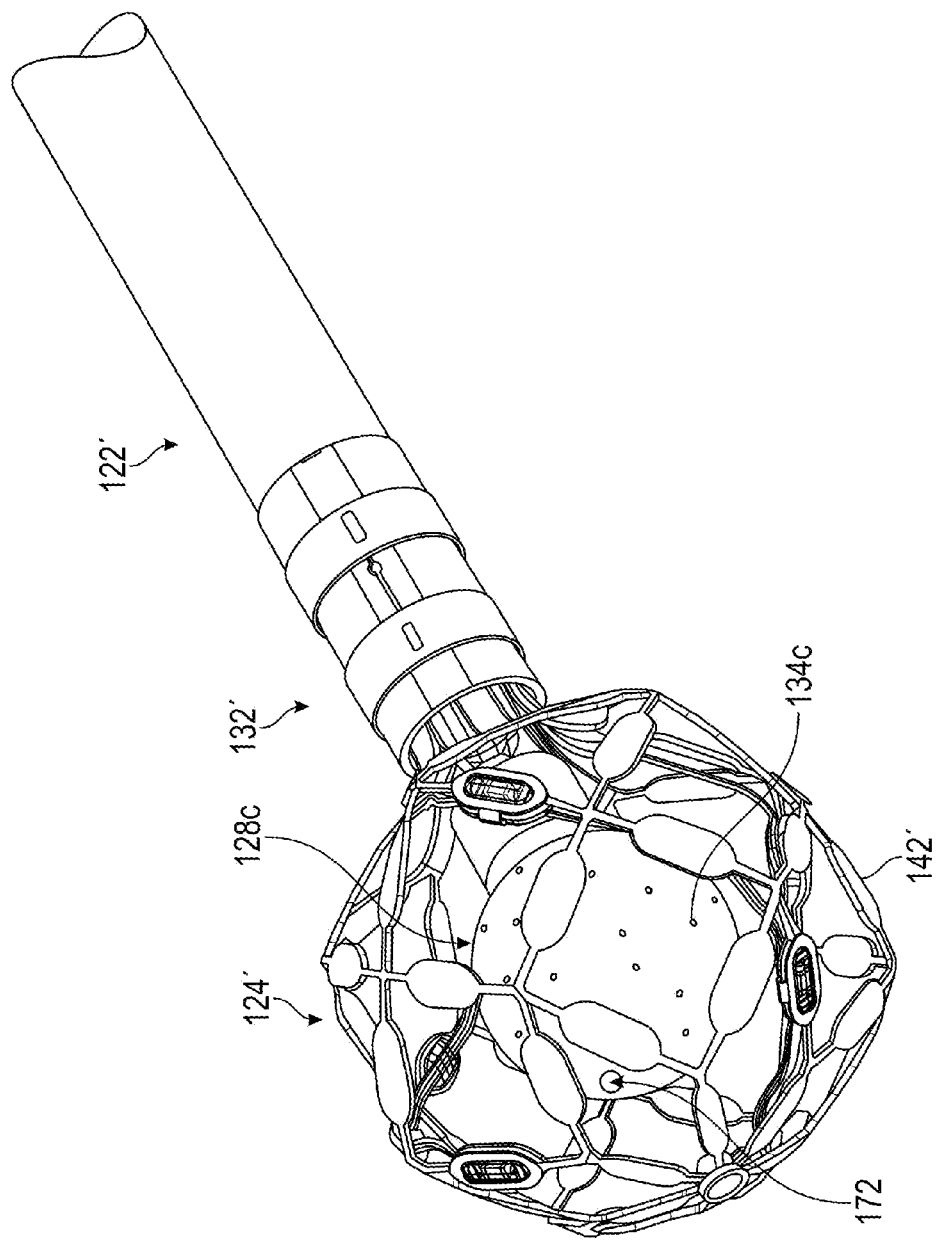
FIG. 18 is a perspective view of a distal end portion of a catheter of an ablation system.

As yet another example, while irrigation elements have been described as including a resilient, expandable helical portion, other types of resilient, expandable irrigation elements are additionally or alternatively possible. For example, referring now to FIG. 18, an irrigation element 128c can be a resilient, inflatable structure, such as balloon, disposed along a distal end portion 132' of a catheter shaft 122' and in fluid communication with a lumen 151'. In certain implementations, the irrigation element 128c and the ablation electrode 124' can each be coupled to the distal end portion 132' of the catheter shaft 122'. Unless otherwise indicated or made clear from the context, an element designated with a primed (') element number in FIG. 18 is similar to a corresponding element designated with an unprimed number in other figures of the present disclosure and, thus, should be understood to include the features of the corresponding element designated with an unprimed number. As one example, therefore, the ablation electrode 124' should be understood to correspond to the ablation electrode 124 (FIG. 3), unless otherwise specified.

In certain implementations, the irrigation element 128c is expandable. For example, the irrigation element 128c can be uninflated and/or underinflated in a delivery state of the distal end portion 132' of the catheter shaft 122' to a treatment site according to any of the methods described herein. In such a delivery state, the irrigation element 128c can be delivered to the treatment site with a low profile (e.g., a profile that is less than or equal to a maximum outer dimension of the catheter shaft 122'). At the treatment site, the irrigation element 128c can be inflated to expand from the delivery state to an expanded state. For example, the irrigation element 128c can expand in a radial direction beyond an outermost dimension of the catheter shaft 122'.

The irrigation element 128c can be a non-compliant balloon or a semi-compliant balloon. In such implementations, the irrigation element 128c can be substantially resistant to deformation when in an inflated state. Thus, in instances in which the irrigation element 128c is non-compliant or semi-compliant, the irrigation element 128c can resist deformation when contacted by an inner portion 136' of the deformable portion 142' of the ablation electrode 124'. As compared to a compliant balloon, this resistance to deformation by the irrigation element 128c can facilitate, for example, control over the flow of irrigation fluid through the irrigation element 128c.

In some implementations, the irrigation element 128c is a balloon formed of one or more polymers. Polymers can be, for example, sufficiently flexible to expand from the delivery state to the expanded state while withstanding forces created by the movement of irrigation fluid through the irrigation element 128c. In instances in which the irrigation element 128c is formed of one or more polymers, irrigation holes can be formed in polymers through laser drilling or other similar secondary processes. Examples of polymers that can be used to form the irrigation element 128c include one or more of: thermoplastic polyurethane, silicone, poly(ethylene terephthalate), and polyether block amide.

The irrigation element 128c can define a plurality of irrigation holes 134c. The irrigation holes 134c can be similar to the irrigation holes 134 defined by the irrigation element 128 (FIG. 3). For example, the irrigation holes 134c can be the same size and shape as the irrigation holes 134 defined by the irrigation element 128. Additionally, or alternatively, the irrigation holes 134c can have the same open area as the irrigation holes 134 defined by the irrigation element 128.

In use, irrigation fluid can flow from the lumen 151', into the irrigation element 128c, and can exit the irrigation element 128c through the plurality of irrigation holes 134c. In general, the plurality of irrigation holes 134c can have a combined area that is less than the cross-sectional area of the lumen 151' such that fluid pressure can build in the inflatable element 128c as the irrigation fluid moves through the irrigation element 128c. It should be appreciated, then, that the pressure in the inflatable element 128c, resulting from the flow of irrigation fluid through the irrigation element 128c, can inflate the irrigation element 128c (e.g., from the delivery state to the expanded state).

In certain implementations, the volume defined by an inner portion 136' of the ablation electrode 124' in an expanded or uncompressed state is larger than the volume defined by the irrigation element 128c in an expanded state. Thus, for example, the inner portion 136' of the ablation electrode 124' (e.g., along the deformable portion 142') can be spatially separated from at least a portion of the surface area of the irrigation element 128c when the irrigation element 128c is in the expanded state. This spatial separation can be advantageous, for example, for developing turbulence of irrigation fluid issuing from the irrigation holes 134c prior to reaching the inner portion 136' of the ablation electrode 124'. It should be appreciated that, as compared to less turbulent flow and/or laminar flow, such turbulence of the flow of irrigation fluid at the inner portion 136' of the ablation electrode 124' can facilitate efficient cooling of the ablation electrode 124'.

The irrigation element 128c can be enveloped by the ablation electrode 124' in an uncompressed state to facilitate, for example, cooling substantially the entire inner portion 136' of the ablation electrode 124'. Additionally, or alternatively, enveloping the irrigation element 128c with the ablation electrode 124' can reduce the likelihood of exposing the irrigation element 128c to undesirable forces such as, for example, forces that can be encountered as the ablation electrode 124' and the irrigation element 128c are moved to the treatment site.

In the expanded state, the irrigation element 128c can include a substantially ellipsoidal portion. As used herein, a substantially ellipsoidal portion can include a substantially spherical shape and deformations of a substantially spherical shape.

In certain implementations, the irrigation holes 134c are defined on this ellipsoidal portion of the irrigation element 128c. Thus, in such implementations, the ellipsoidal portion of the irrigation element 128c can facilitate directing irrigation fluid in multiple, different axial and radial directions. For example, the irrigation holes 134c can be spaced circumferentially (e.g., about the entire circumference) about the ellipsoidal portion of the irrigation element 128c such that irrigation fluid can be directed toward the inner portion 136' of the ablation electrode 142' along various different radial directions. As an additional or alternative example, the irrigation holes 134c can be spaced axially (e.g., along an entire axial dimension of the ellipsoidal portion of the irrigation element 128c) such that the irrigation fluid can be directed toward the inner portion 136' of the ablation electrode 142' along proximal and/or distal axial directions.

A plurality of sensors 126' can be supported on the deformable portion 142' of the ablation electrode 124'. In use, the plurality of sensors 126' can be used to detect deformation of the deformable portion 142'. For example, the irrigation element 128c can include a sensor 172 and electrical signals can be driven between the one or more electrodes on the irrigation element 128c and each of the plurality of sensors 126' according to any of the methods described herein.

Figure 19:
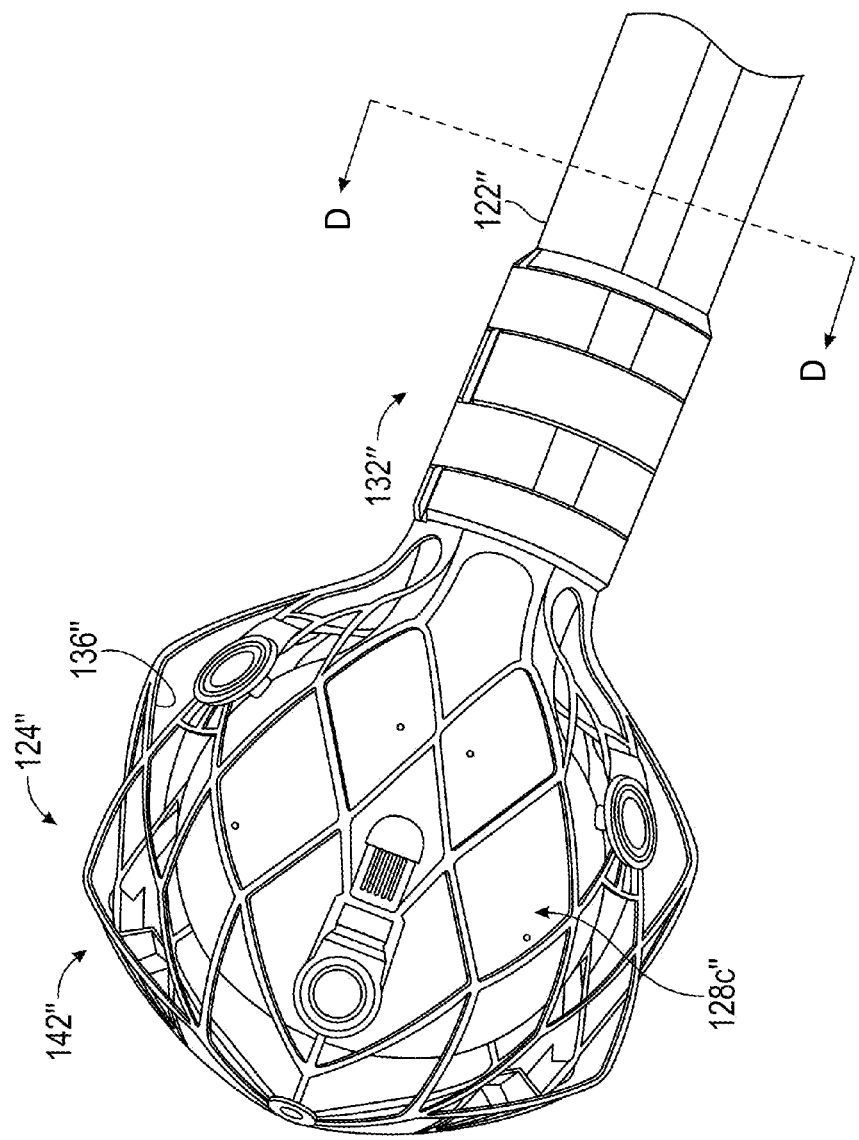
FIG. 19 is a perspective view of a distal end portion of a catheter of an ablation system.
Figure 20:
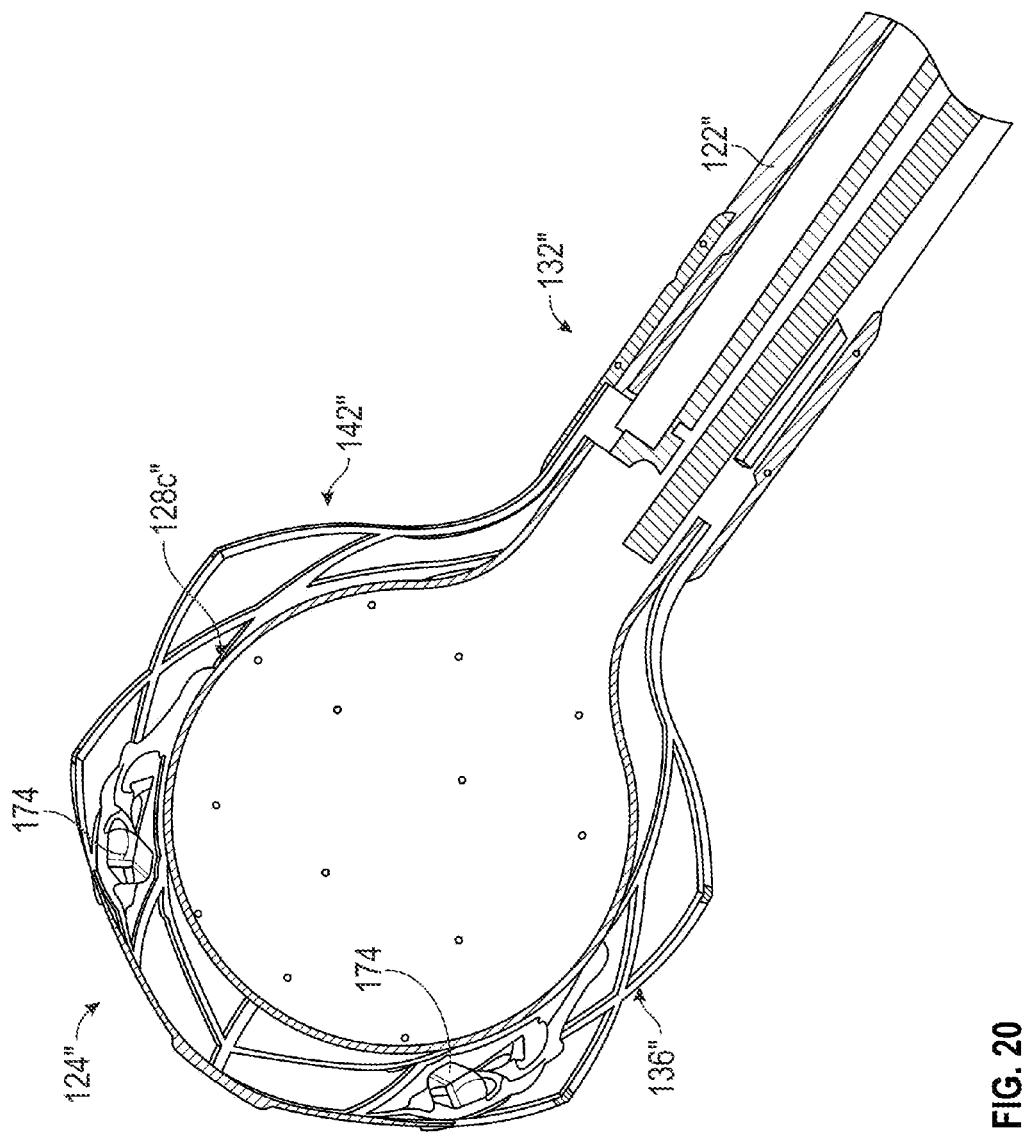
FIG. 20 is a cross-sectional perspective view along cross-section D-D of FIG. 19.

While the plurality of sensors 126' can be used in cooperation with the sensor 172 on the irrigation element 128c, other configurations for sensing deformation of the deformable portion 142' are also or instead possible. For example, referring now to FIGS. 19 and 20, a plurality of sensors 174 can be supported along an ablation electrode 124" at least partially enveloping an irrigation element 128c". Unless otherwise indicated or made clear from the context, an element designated with a double primed (") element number in FIGS. 19 and 20 is similar to a corresponding element designated with an unprimed number and/or with a primed number in other figures of the present disclosure and, thus, should be understood to include the features of the corresponding element designated with an unprimed number and/or with a primed number. As one example, the irrigation element 128c" should be understood to include the features of the irrigation element 128c (FIG. 18), unless otherwise specified or made clear from the context. As another example, the ablation electrode 124" should be understood to include the features of the ablation electrode 124 (FIGS. 3 and 4) and/or of the ablation electrode 124' (FIG. 18), unless otherwise specified or made clear from the context.

Each sensor 174 can include a flexible printed circuit and/or a thermistor similar to any of the flexible printed circuits and/or thermistors described herein, including the flexible printed circuit 150 and/or thermistor 152 described above with respect to FIGS. 10 and 11.

In the uncompressed state of the ablation electrode 124", the inner portion 136" of the ablation electrode 124" is spatially separated from a least a portion of a surface of the irrigation element 128c" such that, for example, at least one of the plurality of sensors 174 is not in contact with the irrigation element 128c". In certain implementations, the ablation electrode 124" in the uncompressed state is not in contact with any of the plurality of sensors 174. That is, in such implementations in which the ablation electrode 124", in the uncompressed state, is spatially separated from one or more of the sensors 126", the default arrangement of the sensors 126" is away from the irrigation element 128c.

The ablation electrode 124" can include a deformable portion 142" that is resiliently flexible from a compressed state (e.g., in which the inner portion 136" of the ablation electrode 124" is in contact with the irrigation element 128c") to an uncompressed state (e.g., in which the inner portion 136" of the ablation electrode 124" is spatially separated from at least a portion of the surface of the irrigation element 128c"). Thus, in such implementations, deformation of the deformable portion 142" can place one or more of the plurality of sensors 174 into contact with the irrigation element 128c" and sensing this contact can be used to determine the shape of the deformable portion 142" in response to a deformation force, such as a force exerted through contact with tissue.

The sensors 174 can be axially and/or circumferentially spaced from one another along the deformable portion 142" of the ablation electrode 124". For example, a first set of the sensors 174 can be disposed distal to a second set of the sensors 174 along the ablation electrode 124" (e.g., along the deformable portion 142"). It should be appreciated that the spatial resolution of the detected deformation of the deformable portion 142" can be a function of the number and spatial distribution of the sensors 174, with a larger number of uniformly spaced sensors 174 generally providing increased spatial resolution as compared to a smaller number of clustered sensors 174.

In use, an electrical signal can be driven between at least one of the sensors 174 and another one of the sensors 174. Measured electrical signals generated between at least one of the sensors 174 and another of the sensors 174 can be received at a processing unit such as any of the processing units described herein (e.g., processing unit 109a described with respect to FIG. 1).

Based at least in part on the measured electrical signals generated between at least one of the sensors 174 and another of the sensors 174, deformation of the deformable portion 142" of the ablation electrode 124" can be detected. For example, as the deformable portion 142" of the ablation electrode 124" deforms, one or more of the sensors 174 can be brought into contact with the irrigation element 128c". It should be appreciated that a certain amount of force is required to deform the deformable portion 142" by an amount sufficient to bring the one or more sensors 174 into contact with the irrigation element 128c". As used herein, this force can be considered a threshold at least in the sense that forces below this threshold are insufficient to bring the one or more sensors 174 into contact with the irrigation element 128c" and, therefore, are not detected as contact between the one or more sensors 174 and the irrigation element 128c".

Contact between the one or more sensors 174 and the irrigation element 128c" can be detected, for example, as a change in the measured electrical signal received, by the processing unit, from the respective one or more sensors 174. As a non-limiting example, contact between one or more of the sensors 174 and the irrigation element 128c can be detected as a rise in impedance of a respective one or more electrical signals associated with the one or more sensors 174 in contact with the irrigation element 128c.

The detection of deformation of the deformable portion 142" of the ablation electrode 124" can, for example, include a determination of whether one or more of the sensors 174 is in contact with the irrigation element 128c. In addition, or instead, the detection of deformation of the deformable portion 142" based on the measured electrical signals can include a detection of a degree and/or direction of deformation of the deformable portion 142". That is, a degree and/or direction of deformation of the deformable portion 142" can be determined based on the number and/or position of the one or more sensors 174 detected as being in contact with the irrigation element 128c.

An indication of a determined state of the deformable portion 142" can be sent to a graphical user interface, such as any one or more of the graphical user interfaces described herein (e.g., the graphical user interface 110 described with respect to FIG. 1). In certain implementations, the degree and/or orientation of deformation of the deformable portion 142" can be sent to the graphical user interface. For example, based on which sensors 174 are detected as being in contact with the irrigation element 128c, a corresponding representation of the compressed state of the deformable portion 142" can be sent to the graphical user interface. The corresponding representation of the compressed state of the deformable portion 142" can be based on, for example, a look-up table of shapes corresponding to different combinations of sensors 174 detected as being in contact with the irrigation element 128c.

An exemplary method of making a catheter including the irrigation element 128c" can include coupling (e.g., using an adhesive) the irrigation element 128c" to a distal end portion 132" of a catheter shaft 122". The deformable portion 142" can be formed according to any one or more of the methods described herein, and the deformable portion 142" can be positioned relative to the irrigation element 128c" such that the inner portion 136" of the ablation electrode 124" envelops the irrigation element 128c". The deformable portion 142" can be coupled to the catheter shaft 122" relative to the irrigation element 128c" such that, in a compressed state, the inner portion 136" of the ablation electrode 124" is in contact with the irrigation element 128c" and, in an uncompressed state, the inner portion 136" of the ablation electrode 124" along the deformable portion 142" is spatially separated from the irrigation element 128c".

Figure 21:
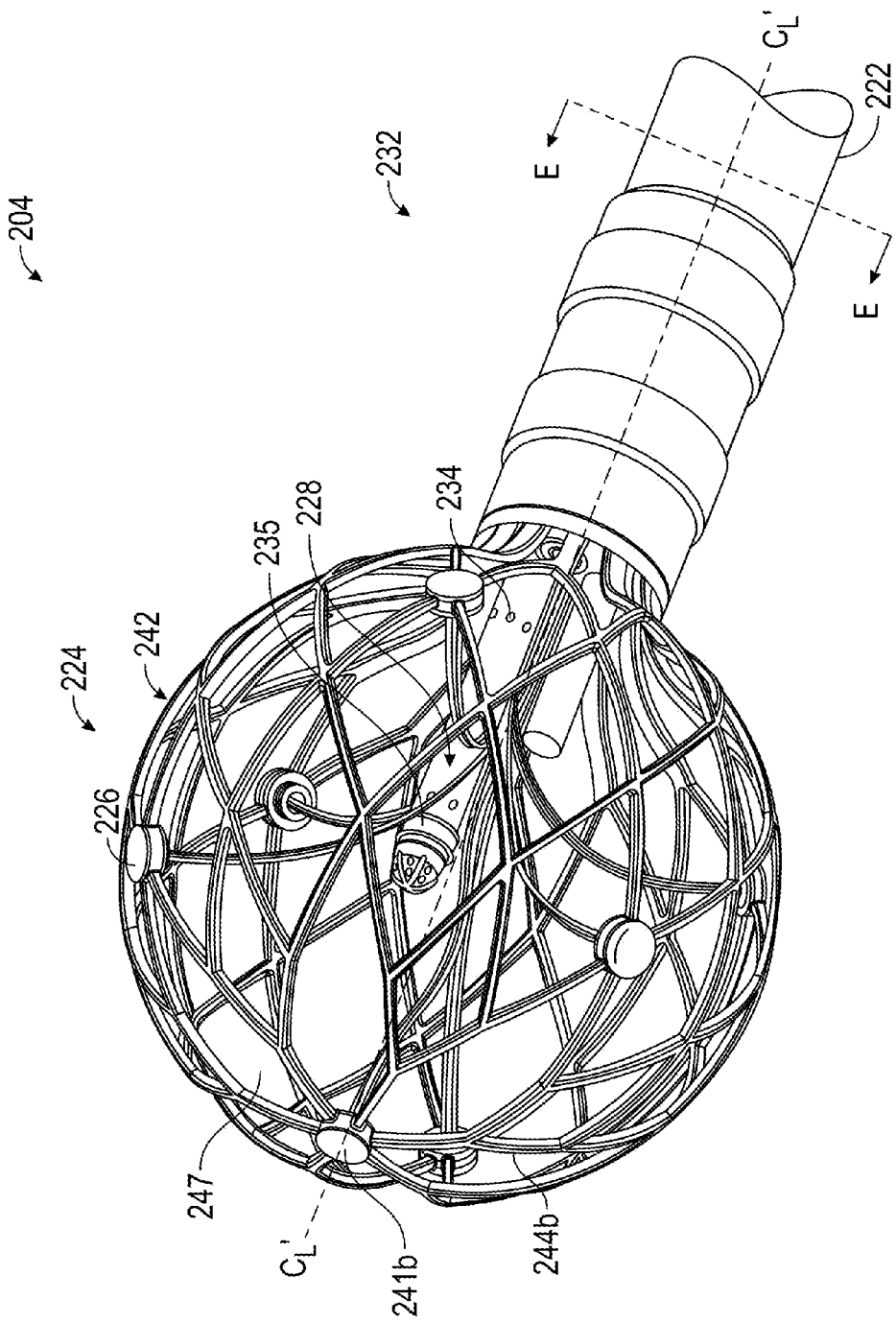
FIG. 21 is a perspective view of a distal end portion of a catheter of an ablation system.
Figure 22:
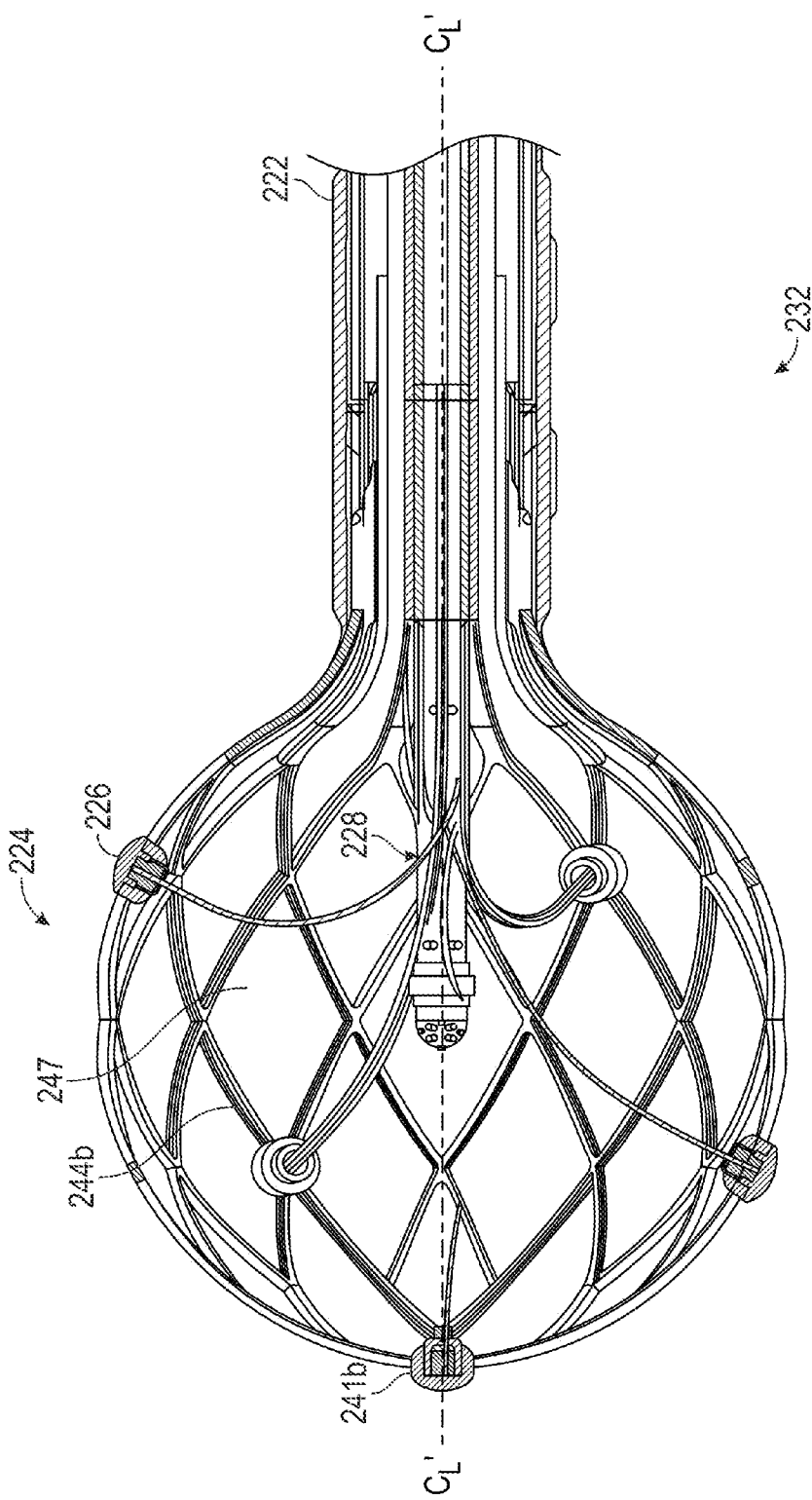
FIG. 22 is a cross-sectional side view of the catheter of FIG. 21 along cross-section E-E. of FIG. 21.

As another example, while certain arrangements of struts to form cells along a deformable portion of an ablation electrode have been described, other configurations are additionally or alternatively possible. For example, referring now to FIGS. 21 and 22, a catheter 204 can include an ablation electrode 224 having struts 244b defining a plurality of cells 247, with the struts 244b progressively ganged together in a direction from a proximal region to a distal region of a deformable portion 242 of the ablation electrode 224. For the sake of efficient and clear description, elements designated by 200-series element numbers in FIGS. 21 and 22 are analogous to or interchangeable with elements with 100-series element numbers (including primed and double-primed element numbers) described herein, unless otherwise explicitly indicated or made clear from the context, and, therefore, are not described separately from counterpart elements having 100-series element numbers, except to note differences or to describe features that are more easily understood with reference to FIGS. 21 and 22. Thus, for example, catheter 204 in FIGS. 21 and 22 should generally be understood to be analogous to the catheter 104 (FIGS. 1-4), unless otherwise explicitly indicated or made clear from the context.

As used herein, a progressively ganged together configuration of the struts 244b can include an arrangement of the struts 244b in which the number of cells in the plurality of cells 247 decreases in a given direction. Thus, for example, the struts 244b can be progressively ganged together in the direction toward the distal end of the deformable portion 242 such that the number of cells 247 defined by the struts decreases in the direction toward the distal end of the deformable portion 242. Thus, as compared to a configuration in which struts are uniformly disposed about a shape, the closed end of the deformable portion 242 of the ablation electrode 224 can be formed by joining together relatively few of the struts 244b. This can be advantageous with respect to, for example, achieving acceptable manufacturing tolerances or, further or instead, facilitating substantially uniform distribution of current density along the deformable portion 242.

In some implementations, the cells in the plurality of cells 247 can be bounded by different numbers of struts 244b, which can facilitate achieving a target distribution of current density along the deformable portion 242. For example, a first set of cells of the plurality of cells 247 can be bounded by struts 244b defining eyelets (e.g., eyelets 157 in FIG. 12B), and a second set of cells of the plurality of cells 247 can be bounded by fewer struts than the first set of cells. For example, the first set of cells of the plurality of cells 247 can be bounded by at least four struts 244b.

In certain implementations, at least some of the cells 247 of the plurality of cells 247 are symmetric. Such symmetry can, for example, facilitate achieving substantially uniform current density in a deformable portion 242 of the ablation electrode 224. Additionally, or alternatively, such symmetry can be useful for achieving suitable compressibility of the deformable portion for delivery to a treatment site (e.g., through a sheath) while also achieving suitable expansion of the deformable portion for use at the treatment site.

At least some of the cells 247 can have mirror symmetry. As used herein, a mirror symmetric shape includes a shape that is substantially symmetric about a plane intersecting the shape, with the substantial symmetry allowing for the presence or absence of a sensor 226 on one or both sides of the plane intersecting the shape. For example, at least some of the cells 247 can have mirror symmetry about a respective mirror symmetry plane passing through the respective cell 247 and containing a center axis CL'-CL' defined by a catheter shaft 222 and extending from a proximal end portion to a distal end portion of the catheter shaft 222. In the side view shown in FIG. 22, a mirror symmetry plane for some of the cells of the plurality of 247 is directed perpendicularly into the page and passes through the center axis CL'-CL'. Additionally, or alternatively, it should be appreciated that the overall deformable portion 242 of the ablation electrode 224 can be symmetric about a plane including the center axis CL'-CL', such as the plane directed perpendicularly into the page and passing through the center axis CL'-CL'.

The mirror symmetry of at least some of the cells of the plurality of cells 247 and/or the overall deformable portion 242 can be useful, for example, for uniform distribution of current density. Additionally, or alternatively, symmetry can facilitate expansion and contraction of the deformable portion 242 of the ablation electrode 224 in a predictable and repeatable manner (e.g., with little to no plastic deformation). For example, each of the cells of the plurality of cells 247 can be symmetric about its respective symmetry plane in the compressed state and in the uncompressed state of the deformable portion 242 of the ablation electrode 224. With such symmetry in the compressed state and in the uncompressed state of the deformable portion 242, the deformable portion 242 can expand with little to no circumferential translation of the deformable portion 242 during expansion, which can facilitate accurate knowledge of the position of the deformable portion 242 during delivery and deployment of the deformable portion 242.

The catheter 204 can be formed according to any one or more of the various different methods described herein. For example, the ablation electrode 224 can be formed from a flat sheet or from a tube, as described herein, such that the ablation electrode 224 has two open ends. A fastener 241b can be inserted through an end of at least some of the struts 244b according to any of the various different methods described herein to couple ends of the struts 244b to close one of the two open ends of the ablation electrode 224. An open end of ablation electrode 224 (e.g., an end opposite the fastener 241b) can be coupled to a distal end portion 232 of the catheter shaft 222 to form the catheter 204.

The following simulation and experiment describe the uniformity of current density associated with the ablation electrode 224 in the uncompressed state. It is to be understood that the simulation and experiment described below are set forth by way of example only, and nothing in the simulation or experiment shall be construed as a limitation on the overall scope of this disclosure.

Figure 23:
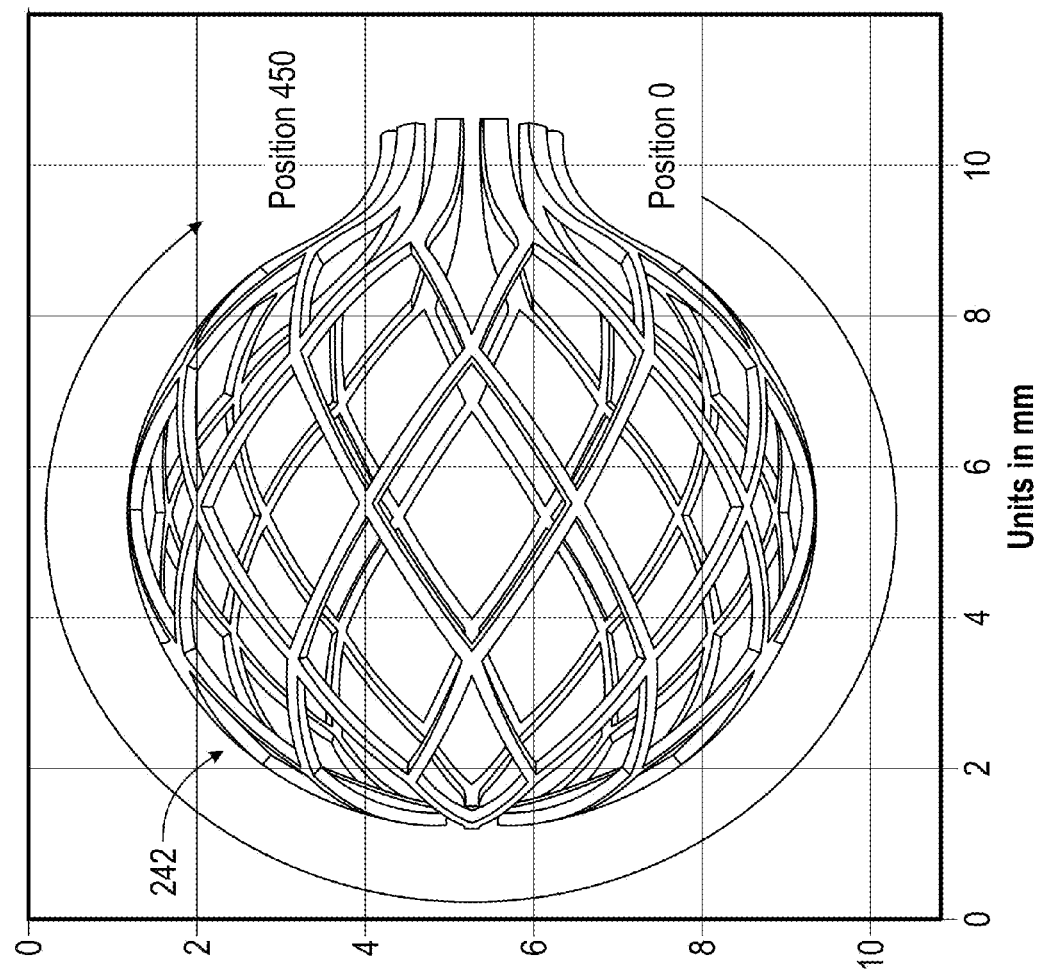
FIG. 23 is a schematic representation of a trajectory around an outer surface of an ablation electrode of the catheter of FIG. 21, the trajectory used to present simulation results of current density associated with the ablation electrode.

Referring now to FIG. 23, current density through the deformable portion 242 of the ablation electrode 224 (FIG. 21) in the uncompressed state was simulated using a finite difference method. In the simulation, the ablation electrode 224 was assumed to have uniform voltage (e.g., 1 V), with the medium set at uniform resistivity. The return electrode was assumed to be the edge of the domain and was set to another uniform voltage (e.g., 0 V). It is believed that the variation in simulated current density along a trajectory (shown as the arc extending from position 0 to position 450) at a fixed distance away from an outer surface of the deformable portion 242 is a proxy for the actual variation in current density along the respective trajectory of the deformable portion 242.

Figure 24:
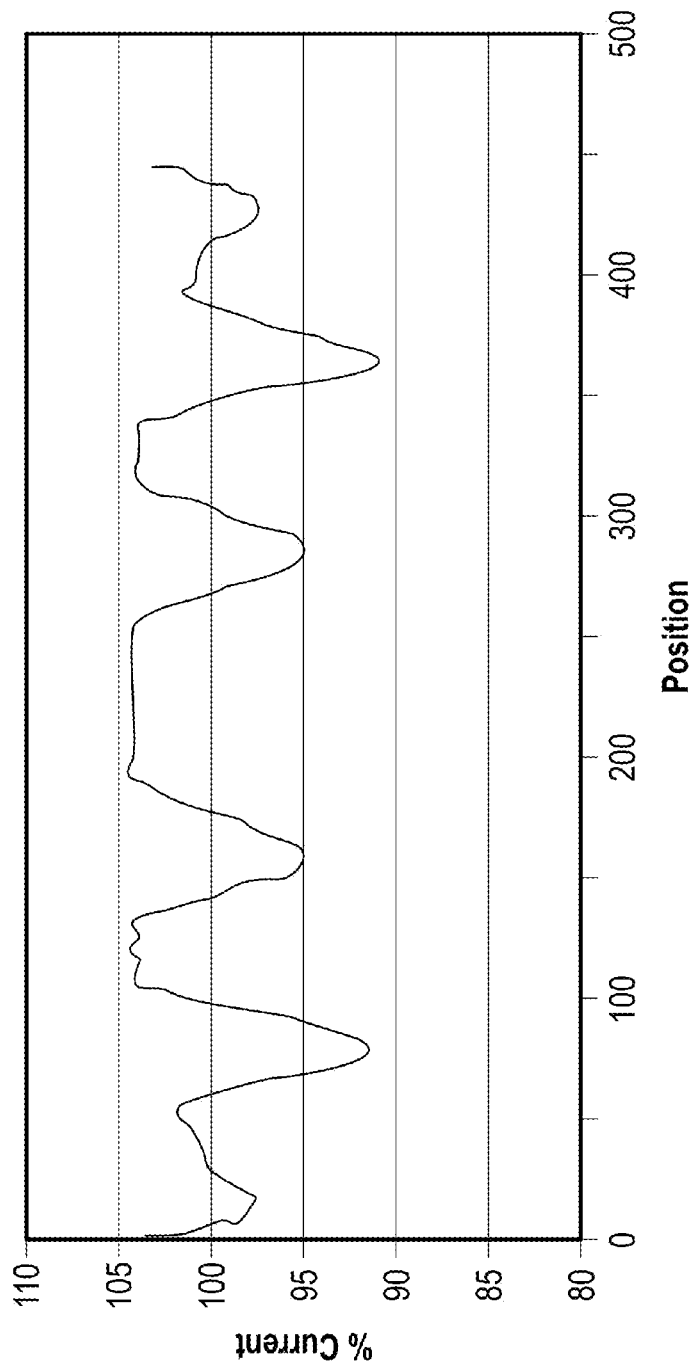
FIG. 24 is a graph of percentage change in simulated current density along the trajectory shown in FIG. 23, at a fixed distance of 1 mm from an outer surface of the ablation electrode.

Referring now to FIGS. 23 and 24, the simulated current density through the deformable portion 242 varies by less than about ±10 percent along the trajectory at 1 mm away from an outer surface of the deformable portion 242 in the uncompressed state. Thus, the current density at a fixed distance near the deformable portion 242 in the uncompressed state is believed to be relatively uniform. Thus, more generally, current density near the surface of the deformable portion 242 is substantially insensitive to the orientation of the deformable portion 242 relative to tissue. Further, given that the deformable portion 242 in the expanded state is larger than a maximum lateral dimension of the catheter shaft 222 (FIG. 21), the deformable portion 242 can reliably deliver wide lesions in any of various different orientations relative to tissue. This can be useful, for example, for reducing treatment time and/or increasing the likelihood that applied ablation energy is sufficient to treat a targeted arrhythmia.

While the results shown in FIG. 24 are based on a simulation using a finite difference method, the general observations drawn from these simulations are supported by the experimental results described below.

Figure 25:
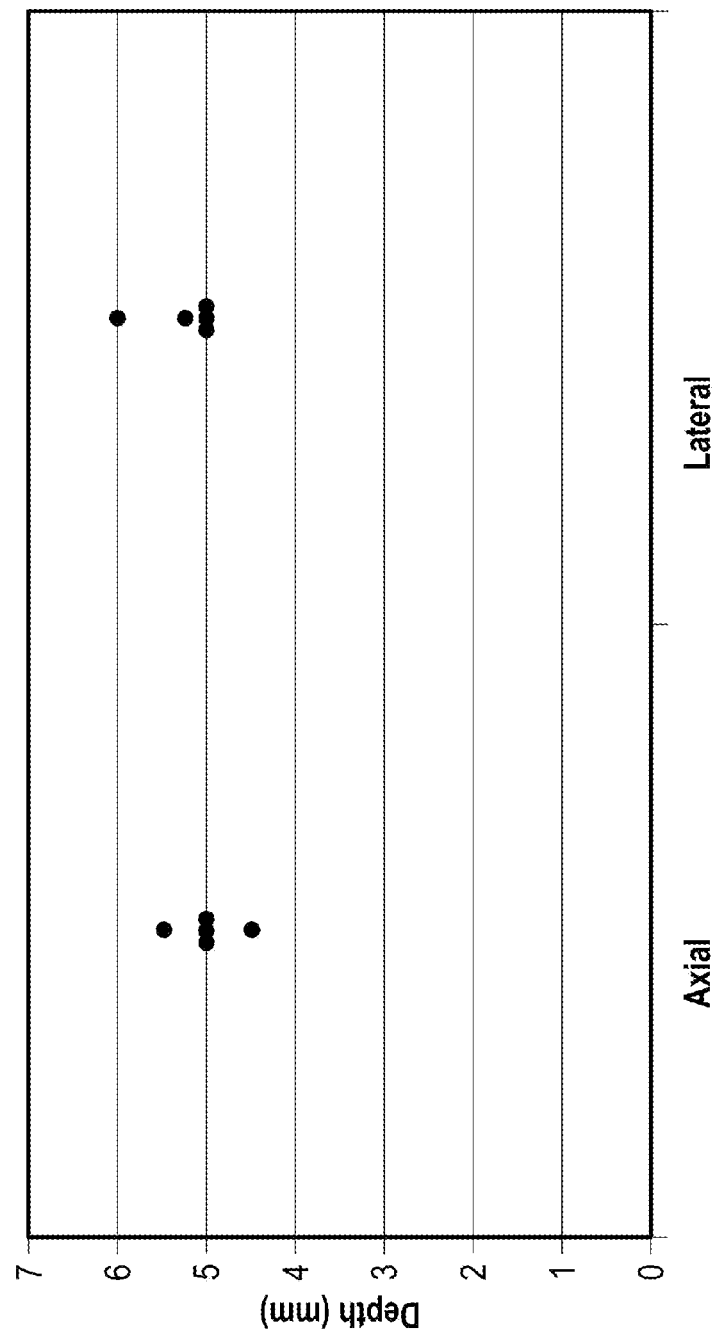
FIG. 25 is a graph of depth and width of lesions applied to chicken breast meat using the ablation electrode of FIG. 21 in axial and lateral orientations relative to the chicken breast meat.

FIG. 25 is a graph of depth of lesions applied to chicken breast meat using the ablation electrode 224 (FIG. 21) in axial and lateral orientations relative to the chicken breast meat. Each lesion was performed on chicken breast meat and 0.45% saline solution at body temperature and, for each lesion, the deformable portion 242 of the ablation electrode 224 (FIG. 21) was in contact with the chicken breast meat with 10 g of force and 8 mL/min of irrigation was used. For each ablation, 2 amperes were delivered to the tissue through the deformable portion 242 (FIG. 21) for ten seconds. Lesion depth was determined using a ruler to measure the depth of tissue discolored from pink to white.

Five of the lesions were created with the deformable portion 242 (FIG. 21) in an axial orientation in which the catheter shaft 222 (FIG. 21) was perpendicular to the chicken breast, and five of the lesions were created with the deformable portion 242 in a lateral orientation perpendicular to the axial orientation. As shown in FIG. 25, although the lesions were created using different orientations, the lesion depths were similar, with lesion depth varying by less than about ±20 percent, indicating that the amount of energy ablating tissue in both orientations is similar. This experimental finding is consistent with the results of the simulation. That is, lesions corresponding to multiple different angles between the deformable portion 242 (FIG. 21) and tissue have similar depth at each of the multiple different angles. Such uniform distribution of current density can facilitate controlling lesion size, which can be particularly useful for ablating thin tissue.

Referring again to FIGS. 21 and 22, an irrigation element 228 is enveloped by the deformable portion 242 of the ablation electrode 224 such that the deformable portion 242 forms an enclosure about the irrigation element 228. The irrigation element 228 can be any of the various different irrigation elements described herein and can be in fluid communication with a catheter shaft 222. For example, the irrigation element 228 can be disposed substantially along the center axis CL'-CL', can extend distally from a distal end portion 232 of the catheter shaft 222, and, also or instead, can define a plurality of irrigation holes 234 disposed along the irrigation element 228 to direct irrigation fluid toward the deformable portion 242 of the ablation electrode 224. Additionally, or alternatively, a center electrode 235 can be disposed along the irrigation element 228 and directly or indirectly coupled to the distal end portion 232 of the catheter shaft 222.

In the absence of force applied to the deformable portion 242 of the ablation electrode 224, the center electrode 235 is spaced apart from the sensors 226. As the deformable portion 242 is brought into contact with tissue through application of force applied to the deformable portion 242, it should be appreciated that, independent of orientation of the deformable portion 242 relative to tissue, the deformable portion 242, and thus the sensors 226, makes initial contact with the tissue before the center electrode 235 makes initial contact with the tissue. In certain implementations, the center electrode 235 remains spaced from tissue under normal operation. That is, the deformable portion 242 of the ablation electrode 224 can be sufficiently rigid to maintain spacing of the center electrode 235 from tissue under a normal range of contact forces, which are less than about 100 g (e.g., less than about 50 g).

Electrical activity detected (e.g., passively detected) by the center electrode 235 and the sensors 226 (acting as surface electrodes) can form the basis of respective electrograms associated with each unique pairing of the center electrode 235 and the sensors 226. For example, in implementations in which there are six sensors 226, the center electrode 235 can form six electrode pairs with the sensors 226 which, in turn, form the basis for six respective electrograms.

An electrogram formed by electrical signals received from each respective electrode pair (i.e., the center electrode 235 and a respective one of the sensors 226) can be generated through any of various different methods. In general, an electrogram associated with a respective electrode pair can be based on a difference between the signals from the electrodes in the pair and, thus more specifically, can be based on a difference between an electrical signal received from the center electrode 235 and an electrical signal received from a respective one of the sensors 226. Such an electrogram can be filtered or otherwise further processed to reduce noise and/or to emphasize cardiac electrical activity, for example.

Because the center electrode 235 remains spaced at an intermediate distance from the sensors 226 and tissue in the range of forces experienced through contact between tissue and the deformable portion 242 of the ablation electrode 224, the electrogram formed from each electrode pair can advantageously be a near-unipolar electrogram. As used herein, a near-unipolar electrogram includes an electrogram formed based on the difference between two electrodes that are greater than about 2 mm apart and less than about 6 mm apart and oriented such that one of the electrodes remains spaced away from tissue. In certain implementations, in the absence of force applied to the deformable portion 242 of the ablation electrode 224, the center electrode 235 is spaced apart from the sensors 226 by distance greater than about 2 mm and less than about 6 mm.

The near-unipolar electrograms associated with the center electrode 235 spaced from the sensors 226 can provide certain advantages over unipolar configurations (i.e., configurations having electrode spacing greater than 6 mm) and over bipolar configurations (i.e., configurations having electrode spacing equal to or less than 2.5 mm and/or allowing both electrodes to be spaced close to tissue). For example, as compared to unipolar electrograms, the near-unipolar electrograms formed based on signals received from the center electrode 235 and the sensors 226 are less noisy and, additionally or alternatively, less susceptible to far-field interference from electrical activity away from the tissue of interest. Also, as compared to unipolar electrograms, a near-unipolar electrogram does not require a reference electrode on a separate catheter or other device. As a further or alternative example, as compared to bipolar electrograms, a near-unipolar electrogram formed based on signals received from the center electrode 235 and the sensors 226 is generated from an electrode pair with only one electrode in the electrode pair in contact with tissue such that the resulting electrogram waveform arises from one tissue site, making it less complex to interpret. Also, or instead, as compared to bipolar electrograms generated from a pair of electrodes in contact with tissue, the signal of a near-unipolar electrogram formed based on signals received from the center electrode 235 and the sensor 226 in contact with tissue can have a more consistent morphology and/or larger amplitude at least because the center electrode 235 is always oriented away from tissue as compared to the sensor 226 in the electrode pair touching tissue.

The sensors 226 can be any of the various different sensors described herein and, in addition or in the alternative, can be arranged on the deformable portion 242 of the ablation electrode 224 according to any of the various different arrangements described here. For example, in the absence of external force applied to the deformable portion 242 of the ablation electrode 224 enveloping the center electrode 235, the sensors 226 can be noncoplanar relative to one another. It should be appreciated that, as compared to a planar arrangement, the electrograms generated from the sensors 226 arranged in such a noncoplanar configuration can be useful for providing improved directional information regarding electrical activity in tissue.

The sensors 226 can be electrically isolated from the deformable portion 242 of the ablation electrode 224 with the sensors 226, acting as surface electrodes, passively detecting electrical activity in tissue in proximity to each respective sensor 226 without interference from the deformable portion 242 of the ablation electrode 224. At least some of the sensors 226 can be at least partially disposed along an outer portion of the deformable portion 242 of the ablation electrode 224 with the deformable portion 242 of the ablation electrode between the center electrode 235 and at least a portion of each respective one of the sensors 226 along the outer portion. Additionally, or alternatively, at least some of the sensors 226 can be at least partially disposed along an inner portion of the deformable portion 242 of the ablation electrode 224. In such implementations, each sensor 226 can be in proximity to tissue without touching tissue as the deformable portion 242 of the ablation electrode 224 touches tissue. Thus, for example, at least some of the sensors 226 can extend through the ablation electrode 224.

Referring now to FIGS. 1, 21, and 22, the catheter 204 can replace the catheter 104 in FIG. 1. Accordingly, electrical signals from the sensors 226 and the center electrode 235 can be directed to the catheter interface unit 108 and, thus, unless otherwise indicated or made clear from the context, should be understood to form a basis for detecting contact with tissue, detecting deformation of the ablation electrode 224, or a combination thereof, according to any one or more of the methods described herein. For example, the signals can be sent to an electrical input stage associated with the catheter interface unit 108. In certain implementations, the difference between electrical signals is determined through electronic circuitry (e.g., a voltage amplifier with a differential input). Additionally, or alternatively, the difference between electrical signals can be determined by the processing unit 109a of the catheter interface unit 108.

In general, the storage medium 109b of the catheter interface unit 108 can have stored thereon computer-executable instructions for causing the processing unit 109a to acquire a plurality of electrograms (e.g., an electrogram for each electrode pair formed by the center electrode 235 and each respective sensor 226). The storage medium 109b be can, also or instead, have stored thereon instructions for causing the processing unit 109a to display a representation of at least one of the plurality of electrograms on the graphical user interface 110. In certain implementations, the storage medium 109b can have stored thereon instructions for causing the processing unit 109a to determine a voltage map associated with the plurality of electrograms, the voltage map corresponding, for example, to electrical activity of a heart of a patient. In some implementations, the storage medium 109b can have stored thereon instructions for causing the processing unit 109a to display the voltage map on the graphical user interface 110. The displayed electrograms, alone or in combination with a displayed voltage map, can be useful for selectively treating tissue of the heart (e.g., delivering ablation energy from the deformable portion 242 of the ablation electrode 224 to tissue in a cavity of the heart).

While the center electrode 235 has been described as being disposed on the irrigation element 228, it should be appreciated that the center electrode 235 can additionally or alternatively be located at any of various different positions within the deformable portion 242 of the ablation electrode 224. For example, the center electrode 235 can be positioned on the distal end portion 232 of the catheter shaft 222. Additionally, or alternatively, the irrigation element 228 itself can be used as a center electrode.

Figure 26:
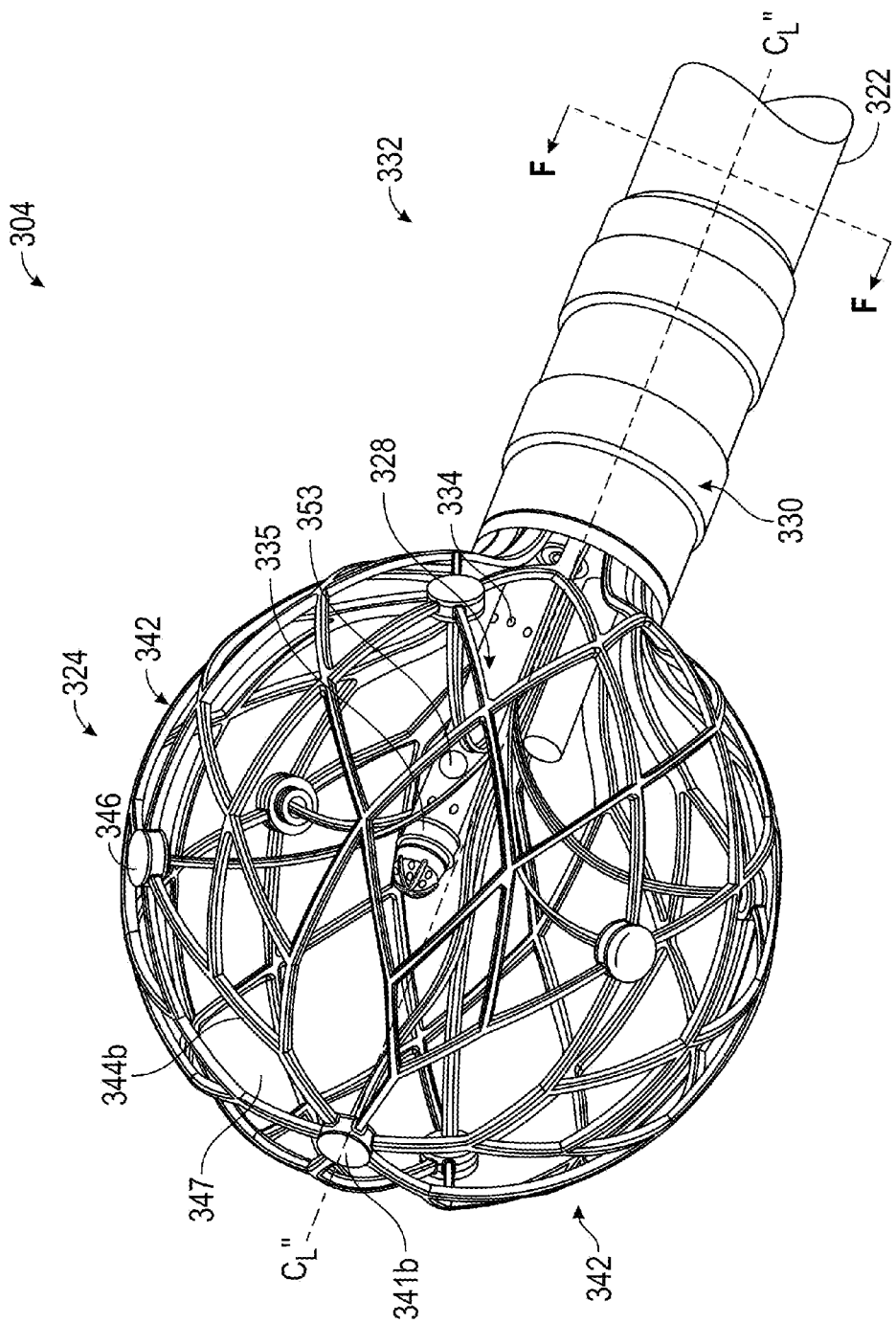
FIG. 26 is a perspective view of a distal portion of a catheter of an ablation system, the catheter including an image sensor.
Figure 27:
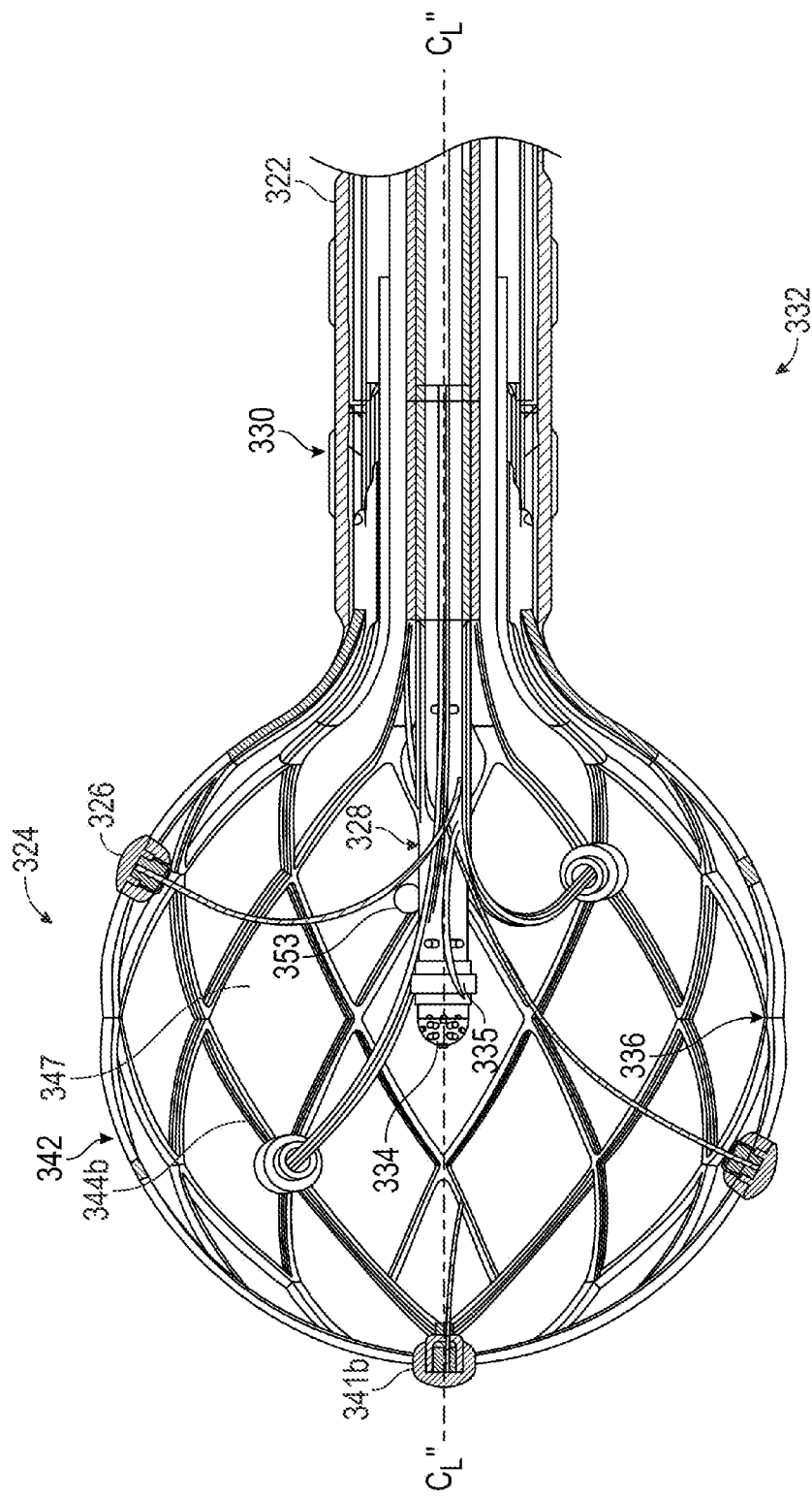
FIG. 27 is a cross-sectional side view of the catheter of FIG. 27 along the cross-section F-F of FIG. 26.

As still another example, while catheters have been described as including certain sensors, other configurations are additionally or alternatively possible. For example, referring now to FIGS. 26 and 27 and as described in greater detail below, a catheter 304 can include a shaft 322, an ablation electrode 324, and at least one image sensor 353. For the sake of efficient and clear description, elements designated by 300-series element numbers in FIGS. 26 and 27 are analogous to or interchangeable with elements with 100-series or 200-series element numbers (including primed and double-primed numbers) described herein, unless otherwise explicitly indicated or made clear from the context, and, therefore, are not described separately from counterpart elements having 100-series element numbers or 200-series element numbers, except to note differences or to described features that are more easily understood with reference to FIGS. 26 and 27.

In general, at least one image sensor 353 can be spaced from an inner portion 336 of the ablation electrode 324 and within a volume at least partially defined by the ablation electrode 324 such that the at least one image sensor 353 is directed toward the inner portion 336 of the ablation electrode 324. As described in greater detail below, such spacing of the at least one image sensor 353 relative to the inner portion 336 of the ablation electrode 324 can facilitate robust acquisition of images during a medical procedure. As also described in greater detail below, such robust acquisition of images can be used to guide certain aspects of a medical procedure, including, for example, one or more of the following: detection of a first anatomical boundary (e.g., endocardium of a heart chamber); detection of tissue thickness; detecting shape; and providing feedback on lesion progress during RF ablation.

Structural elements of the ablation electrode 324 can protect the at least one image sensor 353 from forces encountered by the ablation electrode 324 during delivery, deployment, use, or any combination thereof. For example, the at least one image sensor 353 can be enveloped by the ablation electrode 324, with the ablation electrode 324 protecting the at least one image sensor 353 from a plurality of axial and radial forces (e.g., as the ablation electrode 324 comes into contact with tissue in an anatomic structure). Additionally, or alternatively, the structural elements of the ablation electrode 324 can facilitate maintaining suitable spacing between the at least one image sensor 353 and tissue such that the at least one image sensor 353 can capture useful images of the tissue. As an example, a deformable portion 342 of the ablation electrode 324 can be movable in a direction away from the at least one image sensor 353 as the deformable portion 342 expands from a compressed state to an uncompressed state (e.g., from a delivery configuration to a deployed configuration). Thus, continuing with this example, the deformable portion 342 can be biased in a direction away from the at least one image sensor 353 to facilitate maintaining spacing between the at least one image sensor 353 and tissue in contact with the deformable portion 342 of the ablation electrode 324.

While the structural elements of the ablation electrode 324 can facilitate protecting the at least one image sensor 353 and positioning the at least one image sensor 353 relative to tissue, a plurality of cells 347 defined by the structural elements of the ablation electrode 324 can form an open area that facilitates imaging tissue beyond the ablation electrode 324 (e.g., an open area that is greater than the total surface area of the inner portion 336 of the ablation electrode 324). For example, with the open area formed by the plurality of cells 347, the ablation electrode 324 can be at least partially transparent to imaging energy from the least one image sensor 353 such that the ablation electrode 324 reflects less than half of imaging energy directed from the at least one image sensor 353 toward the ablation electrode 324. That is, images formed by the at least one image sensor 353 can show features of tissue beyond the ablation electrode 324 with little obstruction by the ablation electrode 324.

The at least one image sensor 353 can be positioned according to any of various different imaging requirements associated with use of the ablation electrode 324. Thus, for example, the at least one image sensor 353 can be directed in a direction distal to the ablation electrode 324 to facilitate imaging contact between the ablation electrode 324 and tissue along a plane substantially perpendicular to the shaft 322. In many instances, orientation of the at least one image sensor 353 in this direction can generally facilitate imaging a region of maximum application of force between the ablation electrode 324 and tissue in contact with the ablation electrode 324.

In certain instances, the at least one image sensor 353 can include at least three image sensors. For example, the at least three image sensors can be arranged relative to one another to provide improved spatial resolution, as compared to configurations including less than three image sensors. Continuing with this example, images of the at least one image sensor 353 can be combined to provide a physician with a contextual image of the position of the ablation electrode 324 in the anatomic structure.

In some implementations, the catheter 304 can further include an irrigation element 328 coupled to a distal end portion 332 of the catheter shaft 322. The irrigation element 328 can be, for example, any one or more of the irrigation elements described herein. Accordingly, irrigation fluid can be delivered from the irrigation element 328 toward the inner portion 336 of the ablation electrode 324 to cool the ablation electrode 324 according to any one or more of the various different methods described herein.

The at least one image sensor 353 can be disposed along the irrigation element 328. It should be appreciated that positioning the at least one image sensor 353 on the irrigation element 328 can be useful for spacing the at least one image sensor 353 away from the catheter shaft 322, which can be useful for providing a field of view that is substantially unobstructed by the catheter shaft 322. Additionally, or alternatively, positioning the at least one image sensor 353 on the irrigation element 328 can facilitate achieving a field of view from a position substantially in a middle portion of the ablation electrode 324.

The irrigation element 328 can define irrigation holes 334, with at least a portion of the irrigation holes 334 directed toward a respective field of view of the at least one image sensor 353. For example, at least a portion of the irrigation holes 334 can direct irrigation fluid between the irrigation element 328 and the inner portion of the ablation electrode 336. In use, the direction of irrigation fluid toward the respective field of view of the at least one image sensor 353 can advantageously displace blood from the field of view of the at least one image sensor 353 to facilitate the use of certain imaging modalities, such as the use of a camera as described in greater detail below. That is, the irrigation fluid (e.g., saline) can be substantially transparent to the at least one image sensor 353 such that the use of the irrigation fluid to displace blood from the field of view of the at least one image sensor 353 can facilitate imaging tissue that would otherwise be obscured by blood moving between the at least one image sensor 353 and tissue to be imaged.

In general, the at least one image sensor 353 can include imaging modalities suitable for detecting one or more parameters useful for guiding a medical procedure.

In certain implementations, the at least one image sensor 353 can include a camera such as, for example, a camera including a fish-eye lens. Additionally, or alternatively, the at least one image sensor 353 can include a light source (e.g., a light emitting diode).

Through the use of irrigation fluid to displace blood from a field of view of the camera (e.g., through delivery of irrigation fluid between a field of view of the camera and the inner portion 336 of the ablation electrode 324), one or more images of tissue beyond the ablation electrode 324 can be acquired. Such images can be useful, for example, for detecting contact between the ablation electrode 324 and a first anatomic boundary and thus, in certain applications, can be useful for creating a model of a blood-tissue boundary of the anatomic structure in which the ablation electrode 324 is disposed. Additionally, or alternatively, images acquired with a camera can be useful for providing feedback regarding progression of a lesion being formed through the application of RF energy to tissue in the anatomic structure. For example, images acquired with a camera can be useful for detecting a change in wavelength or other parameter indicative of blanching of tissue as RF ablation energy is applied to the tissue. Further, or instead, images acquired with a camera can be useful for identifying any of various different anatomic landmarks (e.g., a valve) in the anatomic structure.

In implementations in which the at least one image sensor 353 includes a camera, the camera can have a horizontal field of view and a vertical field of view. At least one field of view of the camera can include at least a distal half of the ablation electrode 324. For example, the camera can have at least one field of view including an equator of the deformable portion 342 in implementations in which the deformable portion 342 of the ablation electrode 324 is substantially spherical. Such an orientation of the field of view can be useful, for example, for providing contextual information to the physician regarding the position of the ablation electrode 324 within an anatomic structure. That is, orienting the field of view of a camera to include at least a distal half of the ablation electrode 324 can be useful for imaging tissue in contact with the ablation electrode 324 along primary directions of movement of the ablation electrode 324. Further, or instead, to facilitate imaging tissue beyond the ablation electrode 324, a focal length of the at least one image sensor 353 can be outside of the ablation electrode 324.

In some implementations, the at least one image sensor 353 can include at least one ultrasound transducer. In such implementations, the ablation electrode 324 disposed about the at least one ultrasound transducer can be useful for maintaining sufficient spacing between the ultrasound transducer and tissue being imaged to facilitate acquiring useful images of the tissue of the anatomic structure. In general, there can be large variations in the response of an ultrasound transducer to reflections within the near field (or Fresnel region). Thus, as used herein, "sufficient spacing" for an A-mode ultrasound transducer can be considered to include maintaining the tissue in the far field (or Fraunhofer region) of the ultrasound transducer, beyond the Fresnel region.

In general, the at least one ultrasound transducer can be in any number, shape, and arrangement, as required to achieve a suitable image. Thus, for example, the at least one ultrasound transducer can include a single ultrasound transducer. Continuing with this example, the single ultrasound transducer can be used in "A-mode" imaging, with the image being a one-dimensional depth profile over time that can, optionally, be displayed on a graphical user interface. Additionally, or alternatively, two or more ultrasound transducers (e.g., six ultrasound transducers) can be arranged relative to one another to acquire images along multiple different dimensions of the anatomic structure. In certain implementations, images acquired along multiple different dimensions can be combined with one another (e.g., into a stereoscopic image) and shown on a graphical user interface (e.g., the graphical user interface 110 in FIG. 1). More generally, it should be appreciated that the term "image," as used in the context of ultrasound transducers described herein, should be understood to include information detected by the at least one ultrasound transducer along one or more dimensions and, thus, is inclusive of the one-dimensional depth profile over time (acquired by a single ultrasound transducer) as well as a combination of signals from multiple ultrasound transducers.

For example, the at least one ultrasound transducer can be radially symmetric. Additionally, or alternatively, each ultrasound transducer can include an ultrasound transducer array of piezoelectric crystals that send ultrasound signals in a direction from the at least one image sensor 353 toward the inner portion 336 of the ablation electrode 324 to image tissue beyond the ablation electrode 324. Echoes of the ultrasound signals can be received at the array of piezoelectric crystals to form an ultrasound image, as is known in the art. In general, the at least one image sensor 353 including the ultrasound transducer can provide information regarding tissue depth in an area being imaged.

In certain instances, the at least one image sensor 353 can include at least one ultrasound transducer having a beam width at least twice as wide as a respective transverse dimension of at least some of struts 344b collectively defining a plurality of open cells 347. Through such sizing, the struts 344b can be at least partially transparent to the ultrasound transducer beam and, therefore, the at least one image sensor 353 can image tissue beyond the ablation electrode 324 with little interference from portions of the ablation electrode 324 between the at least one ultrasound transducer and the tissue to be imaged. As an example, the struts 344b can be sized to reflect less than half of the ultrasound energy of the ultrasound transducer beam directed from the at least one image sensor 353 toward the ablation electrode 324.

The catheter 304 can further include a location sensor 330 fixed relative to a distal end portion 332 of the catheter shaft 322. The location sensor 330 can include, for example, a magnetic sensor such as any one or more of various magnetic position sensors well known in the art and that can be positioned at any point along the distal end portion 332 of the catheter shaft 322. The location sensor 330 can, for example, include one or more coils that detect signals emanating from magnetic field generators. Continuing with this example, one or more coils for determining position with five or six degrees of freedom can be used. A magnetic field detected by the location sensor 130 can be used to determine the position of the distal end portion 332 of the catheter shaft 322 according to one or more methods commonly known in the art such as, for example, methods based on using the magnetic sensor to sense magnetic fields in the bed and using a look-up table to determine location of the location sensor 330.

Because the location sensor 330 is coupled to the distal end portion 332 of the catheter shaft 322 in a known, fixed relationship to the at least one image sensor 353, the location sensor 330 can provide location information associated with images acquired by the at least one image sensor 353. Such location information can be useful, for example, for displaying the images on a graphical user interface (e.g., the graphical user interface 110 in FIG. 1) along with a representation of the ablation electrode 324, the anatomic structure, or both. Thus, as a specific example, the physician can use a combination of images from the at least one image sensor 353 and a representation of the ablation electrode 324 relative to a representation of an anatomic structure to position the ablation electrode 324 along a desired location of the anatomic structure. Additionally, or alternatively, the location information associated with the images can be useful for tagging locations on a model of the anatomic structure based on one or more features observed in the images shown on the graphical user interface.

Referring now to FIGS. 1 and 26-30, the catheter interface unit 108 can be in communication with the at least one image sensor 353, and the generator 116 can be in electrical communication with the ablation electrode 324. The storage medium 109b can have stored thereon computer executable instructions for causing one or more processors of the processing unit 109a to execute any one or more of various, different exemplary methods including, for example, the exemplary methods shown in FIGS. 28-30.

Figure 28:
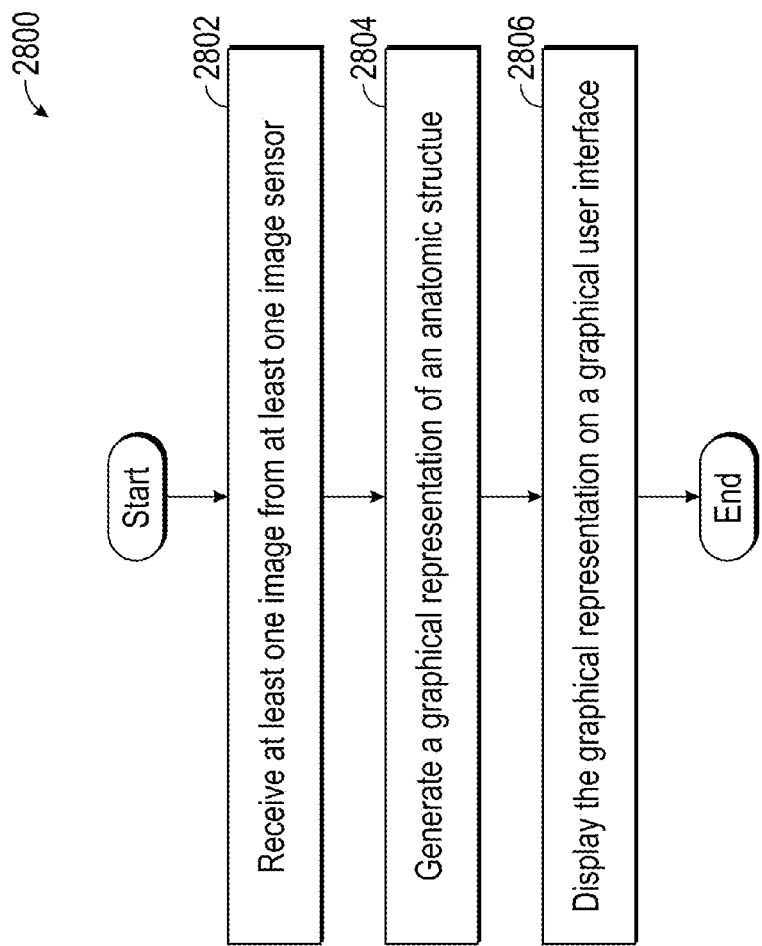
FIG. 28 is a flowchart of an exemplary method of displaying a graphical representation of an anatomic structure.

Referring now to FIG. 28, an exemplary method 2800 can include receiving 2802 at least one image from at least one image sensor, generating 2804 a graphical representation of an anatomic structure based on the at least one image, and sending 2806 the graphical representation of the anatomic structure to a graphical user interface. In general, any one or more of the steps of the exemplary method 2800 can be implemented using any one or more of the devices, systems, and methods described herein, unless otherwise indicated or made clear from the context.

In general, the at least one image from the at least one image sensor can be received 2802 at a catheter interface unit (e.g., the catheter interface unit 108 in FIG. 1) through wired communication, wireless communication, or a combination thereof. In certain implementations, the at least one image from the at least one image sensor can be received 2802 periodically (e.g., at a substantially fixed frequency). For example, the at least one image from the image sensor can be received 2802 at a frequency (e.g., at least about 10 images per second) sufficient to form a substantially continuous display of the images on a graphical user interface. In some implementations, however, the at least one image from the at least one image sensor can be received 2802 intermittently, such as at predetermined intervals, in response to a command from a physician, during periods in which irrigation fluid is delivered to displace blood from a field of view, during periods of detected contact with tissue, and combinations thereof.

Generating 2804 the graphical representation of the anatomic structure based on the at least one image can include, for example, combining information from a plurality of images of the anatomic structure as the ablation electrode is moved through the anatomic structure. For example, in implementations in which the at least one image sensor includes an ultrasound transducer, combining information from a plurality of images can be useful for reducing noise and, further or instead, for more clearly resolving structures. More generally, reflected imaging energy can vary significantly with angle and, thus, it can be useful to image the same location from multiple views and combine such information to generate 2804 the graphical representation of the anatomic structure.

At least some of the images of the plurality of images can correspond to different locations of the ablation electrode in the anatomic structure. Additionally, or alternatively, the graphical representation can be based at least in part on the known location of the ablation electrode corresponding to the respective image. The known location of the ablation electrode can be based on any one or more of the methods described herein. Thus, for example, the location of the ablation electrode in the anatomic structure can be based at least in part on an electric field present in at least a portion of the anatomic structure. Additionally, or alternatively, the location of the ablation electrode in the anatomic structure can be based at least in part on a signal from a magnetic sensor fixed relative to a distal end portion of a catheter shaft carrying the ablation electrode.

In certain implementations, generating 2804 the graphical representation of the anatomic structure can include detecting an anatomical boundary based at least in part on the at least one image. As an example, because the position of the at least one image sensor is known (e.g., through a substantially fixed relationship to the location sensor) as the ablation electrode is moved through the anatomic structure, the detection of the anatomical boundary in multiple images can be combined to form the graphical representation. As a more specific example, the anatomic boundary can include a blood-tissue boundary and, in certain instances, one or more of the position and shape of the blood-tissue boundary can be based on the at least one image. In some implementations, the position and shape of the blood-tissue boundary determined based on the at least one image can be further based on signals indicative of contact between the ablation electrode and tissue.

Detecting the anatomical boundary can be achieved through analysis of the at least one image. Such analysis can include, for example, application of machine vision to the at least one image. Additionally, or alternatively, detecting the anatomical boundary can be based on an input from a physician or technician (e.g., a tag indicative of an anatomic landmark such as a valve).

Generating 2804 the graphical representation of the anatomic structure can, further or instead, include detecting a shape of the anatomic boundary based at least in part on the at least one image. For example, the at least one image can be used to determine the shape of the deformable portion of the ablation electrode as the deformable portion contacts tissue. That is, the shape of the deformable portion of the electrode can change based on the amount and direction of force of contact between the anatomic structure and the deformable portion of the electrode (e.g., according to any one or more of the implementations described herein, unless otherwise specified or made clear from the context). Thus, the shape of the deformable portion detected in the image can be used to determine one or more of force of contact and direction of contact. Such information regarding direction and force of contact can be useful for, among other things, positioning the deformable portion of the ablation electrode for the delivery of energy to the tissue. Additionally, or alternatively, information regarding direction and force of contact can be useful for providing local shape information regarding the area of contact between the anatomic structure and the deformable portion of the ablation electrode, with such local shape information useful, for example, for forming an accurate representation of the anatomic structure on the graphical user interface.

In implementations in which the at least one image is an ultrasound image or another type of image suitable for detecting thickness of tissue, generating 2804 the graphical representation of the anatomic structure can include determining thickness of the tissue of the anatomic structure based at least in part on the at least one image. As used herein, thickness of tissue of the anatomic structure generally includes a distance from one surface of tissue to another surface of tissue and, more specifically, can include a distance from one surface of tissue to another surface of tissue along an axis perpendicular to at least one of the surfaces of tissue.

In implementations in which the anatomic structure is a cavity of the heart, for example, thickness of the tissue should be understood to include a distance between endocardial tissue and epicardial tissue. In particular, cardiac muscle has characteristics that can be useful for measuring thickness of tissue using ultrasound. That is, as compared to blood and other fluids (e.g., irrigation fluid) present in the heart during a cardiac procedure, cardiac muscle is generally both more reflective and more attenuative to ultrasound. Thus, the endocardial boundary of the cardiac muscle can be readily detected as an increase in reflected energy in response to ultrasound energy. The epicardial boundary can be detected as a change in reflection (e.g., a narrow reduction, step change, or both). Further, or instead, the epicardial boundary can be detected as a difference in velocity (e.g., a Doppler detection method). Accordingly, it should be understood that the thickness of the tissue of the cavity of the heart can be determined as a difference in distance between these boundaries. In certain instances, the thickness of the heart cavity can be determined along various different directions along the heart cavity as ultrasound images are acquired at various different locations, and the thickness of the heart cavity can be determined at various different locations along the tissue. While the determination of thickness has been described as being useful for a heart cavity, it should be appreciated that such thickness determination can, more generally, be useful in any anatomic structure in which surfaces separated by tissue are detectable through the use of ultrasound.

Determination of thickness can be useful for, among other uses, providing feedback regarding the amount of ablation power suitable for forming a lesion at a given location of the anatomic structure. The feedback provided regarding thickness of the anatomic structure can include, as an example, a display of visual indicia of the thickness on the graphical user interface. The visual indicia of the thickness can take any one or more of various forms, including a thickness map of the anatomic structure, with the map showing variation of thickness at various different positions along the anatomic structure. The variation of thickness in the map can be based on, for example, a color scale such that differences in thickness can be readily appreciated by a physician, or other personnel, using the map as part of a medical procedure. In certain implementations, the thickness map of the anatomic structure can be sliced along any one or more of various different planes to show a cross-section of tissue thickness at a given point along the anatomic structure. For example, a physician, or other personnel, can select a plane useful for visualization of tissue thickness along a particular portion of the anatomic structure, and the thickness map of the anatomic structure can be sliced along the selected plane.

In certain implementations, generating 2804 the graphical representation can include detecting progress of the lesion based on the at least one image. For example, in implementations in which the at least one image sensor includes a camera, detecting progress of the lesion can include detecting a change in color of tissue in the anatomic structure. The change in color can be, for example, indicative of progress of a lesion formed through the application of RF ablation energy from the ablation electrode to the tissue. That is, the change in color can be a change from red to white as the tissue is ablated. Additionally, or alternatively, in implementations in which the at least one image sensor includes an ultrasound transducer, detecting progress of the lesion can include detecting microbubbles formed as tissue is ablated and determining progress of the lesion based on the detected microbubbles.

An indication of the lesion progress can be sent to the graphical user interface. For example, the indication of lesion progress can be shown on the graphical user interface to provide the physician with a visual representation of progress of a lesion. Such visualization can be useful, for example, for facilitating accurate application of lesions (e.g., an overlapping pattern) as part of a medical procedure.

Displaying 2806 the graphical representation of the anatomic structure on the graphical user interface can include any manner and form of display known in the art. Thus, for example, displaying 2806 the graphical representation of the anatomic structure on the graphical user interface can include projecting a two-dimensional representation of a three-dimensional model of the anatomic structure to a two-dimensional graphical user interface, such as a two-dimensional computer monitor well known in the art. Additionally, or alternatively, displaying 2806 the graphical representation of the anatomic structure on the graphical user interface can include displaying a three-dimensional model of the anatomic structure to a three-dimensional display, such as a virtual reality or an augmented reality display environment.

Figure 29:
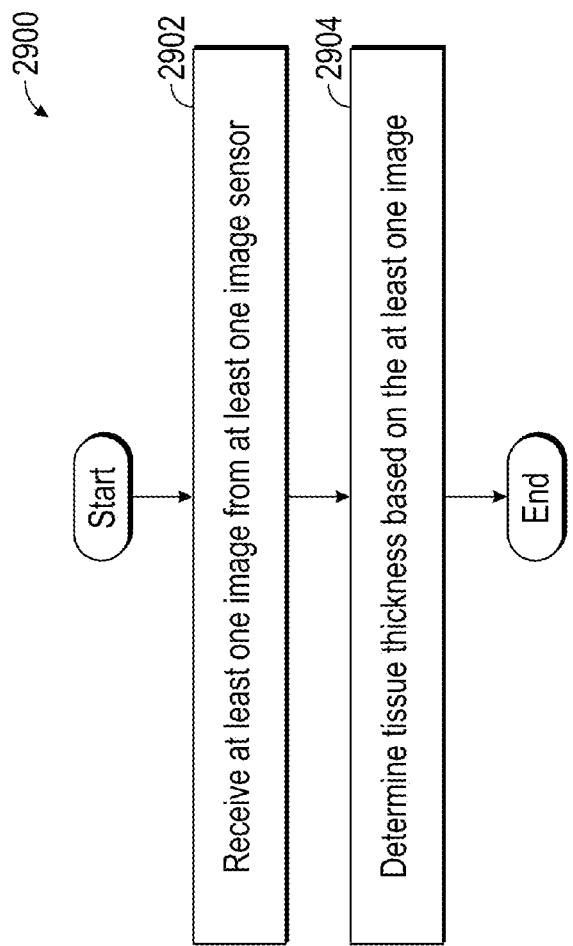
FIG. 29 is a flowchart of an exemplary method of determining tissue thickness.

Referring now to FIG. 29, an exemplary method 2900 can include receiving 2902 at least one image from at least one image sensor, and determining 2904 tissue thickness based on the at least one image. In general, any one or more of the steps of the exemplary method 2900 can be implemented using any one or more of the devices, systems, and methods described herein, unless otherwise indicated or made clear from the context.

Receiving 2902 the at least one image from the at least one image sensor can include any one or more of the various different methods of receiving an image described herein. Thus, for example, receiving 2902 the at least one image from the at least one image sensor should be understood to be similar to the step of receiving 2802 the at least one image described with respect to the exemplary method 2800 (FIG. 28), unless otherwise indicated or made clear from the context.

Determining 2904 thickness of tissue of the anatomic structure can include any one or more of the various different methods of determining thickness described above with respect to the exemplary method 2800 (FIG. 28), unless otherwise indicated or made clear from the context. Likewise, any of the various different methods of determining 2904 described with respect to the exemplary method 2900 should be understood to be interchangeable with implementations of the exemplary method 2800 including tissue thickness determination, unless otherwise indicated or made clear from the context.

In certain implementations, the determining 2904 thickness of tissue of the anatomic structure can be based on a three-dimensional localization of the at least one image sensor. The three-dimensional localization can be based, for example, on one or more location signals received from a location sensor carried by the catheter and, more specifically, can be based on signals received from any one or more of the location sensors described herein.

In general, respiration, heartbeat, and movement of blood past and through the ablation electrode can cause small, unintentional movements of the at least one image sensor during use. Accordingly, in some implementations, signal processing of the at least one image and/or gating based on heartbeat or respiration can be useful for making determinations based on the at least one image. For example, determining 2904 thickness of tissue of the anatomic structure can be based on information from one or more previous positions of the at least one image sensor to smooth the influence of fluctuation of position of the at least one image sensor. More specifically, the smoothing can be based on previously received images, previously received locations, or a combination thereof. It should be understood that smoothing the determined 2904 tissue thickness can reduce the influence of any one image or position on the overall tissue thickness map and, thus, can be useful for improving overall accuracy of a tissue thickness map of the anatomic structure.

Referring now to FIG. 30, an exemplary method 3000 of using at least one image sensor can include expanding 3002 an ablation electrode from a compressed state to an uncompressed state, positioning 3004 an outer portion of the ablation electrode at a treatment site, acquiring 3006 at least one image of the treatment site from at least one image sensor, and delivering 3008 RF energy to the ablation electrode at the treatment site based at least in part on the at least one image of the treatment site. In general, the exemplary method 3000 can be carried out using any one or more of the devices, systems, and methods described herein, unless otherwise indicated or made clear from the context.

Expanding 3002 the ablation electrode from the compressed state to the uncompressed state can include any one or more of the various different devices, systems, and methods of expanding an ablation electrode described herein. In general, the ablation electrode can include a plurality of struts (e.g., the struts 344b shown in FIGS. 26 and 27) defining a plurality of cells (e.g., the cells 347 shown in FIGS. 26 and 27). The struts can flex away from one another to expand 3002 the ablation electrode from the compressed state to the uncompressed state. The at least one image sensor can be proximal to an inner portion of the ablation electrode such that the ablation electrode in the uncompressed state envelops the at least one image sensor. In certain implementations, expanding 3002 the ablation electrode includes moving the ablation electrode in a direction away from the at least one image sensor. Blood can move between the at least one image sensor and the inner portion of the ablation electrode with the ablation electrode in the uncompressed state.

Positioning 3004 the ablation electrode at the treatment site can include, for example, moving the ablation electrode into contact with tissue. Such movement of the ablation electrode can be guided, for example, by one or more images acquired 3006 from the at least one image sensor. For example, the one or more images acquired 3006 by from the at least one image sensor can detect an anatomic boundary according to any one or more of the methods described herein, and positioning 3004 the ablation electrode can be based on a representation of the detected anatomic boundary on a graphical user interface. As a specific example, the graphical representation of the anatomic boundary can include a representation of endocardial tissue of a patient's heart.

Acquiring 3006 the at least one image of the treatment site from at least one image sensor can include acquiring a plurality of images of the treatment site from respective different locations of the ablation electrode within the anatomic structure according to any one or more of the various different devices, systems, and methods described herein. Thus, for example, acquiring 3006 the at least one image of the treatment site from the at least one image sensor can include receiving one or more of an image from a camera, an ultrasound transducer, or a combination thereof, as the ablation electrode is moved in the anatomic structure.

Further, or instead, acquiring 3006 the at least one image of the treatment site can include determining a location associated with each respective image and forming a graphical representation of an anatomic boundary based on the plurality of images and the associated locations, also according to any one or more of the various different devices, systems, and methods described herein. Thus, for example, determining the location associated with each respective image can be based on an electric field present in at least a portion of the anatomic structure. The electric field can be at least partially generated by one or more electrodes external to the anatomic structure (e.g., a return electrode, such as the return electrode 118 in FIG. 1). Further, or instead, the electric field can be at least partially generated by one or more electrodes carried by the catheter within the anatomic structure, such as any of the various sensors described herein (e.g., the sensors 126 in FIGS. 3 and 4).

Delivering 3008 RF energy to the ablation electrode at the treatment site based at least in part on the at least one image of the treatment site can include, for example, varying RF energy delivery based on tissue thickness at the treatment site. The tissue thickness can be determined, for example, according to any one or more of the various different methods described herein and, thus, can be based on one or more ultrasound images acquired by the one or more image sensors.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals.

It will further be appreciated that a realization of the processes or devices described above may include computer-executable code created using a structured programming language such as C, an object oriented programming language such as C++, or any other high-level or low level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices.

In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A catheter, comprising:
a shaft having a proximal end portion and a distal end portion opposite the proximal end portion;
an ablation electrode at the distal end portion of the shaft including a deformable portion, wherein the deformable portion of the ablation electrode is movable between a compressed state and an uncompressed state, and wherein the ablation electrode, when in the uncompressed state, is configured to allow blood to flow therethrough; and
at least one ultrasound transducer, wherein an ultrasound transducer of the at least one ultrasound transducer is mounted at a fixed location relative to the shaft within a volume at least partially defined by the deformable portion of the ablation electrode or is mounted to the deformable portion of the ablation electrode, and
wherein the ultrasound transducer is generally directed in a distal direction such that the ultrasound transducer is configured to image (a) at least a portion of the ablation electrode, (b) tissue of an anatomic structure in which the catheter is positioned, or (c) a combination thereof.

2. The catheter of claim 1 wherein the ultrasound transducer is radially symmetric.

3. The catheter of claim 1 wherein the at least one ultrasound transducer includes an A-mode ultrasound transducer.

4. The catheter of claim 1 wherein:
the ablation electrode includes an outer portion and an inner portion opposite the outer portion;
the ultrasound transducer is disposed within the volume at least partially defined by the ablation electrode; and when the ablation electrode is in the uncompressed state and, in the absence of external force, the ultrasound transducer is spaced apart from an inner portion of the ablation electrode.

5. The catheter of claim 4 wherein, when the ablation electrode is in the uncompressed state and in the absence of the external force, the ultrasound transducer is spaced apart from the inner portion of the ablation electrode by a distance greater than a focal length of the ultrasound transducer.

6. The catheter of claim 4 wherein the ablation electrode is movable in a direction away from the ultrasound transducer as the ablation electrode expands from the compressed state to the uncompressed state.

7. The catheter of claim 4, further comprising a fluid delivery element, and wherein:
the fluid delivery element is coupled to the distal end portion of the shaft and extends into the volume at least partially defined by the deformable portion of the ablation electrode; and
the ultrasound transducer is mounted on the fluid delivery element.

8. The catheter of claim 1 wherein:
the ablation electrode includes a plurality of struts; and
the ultrasound transducer has a beam width at least twice as wide as a respective transverse dimension of at least some of the struts.

9. The catheter of claim 1 wherein the at least one ultrasound transducer includes an ultrasound transducer array.

10. The catheter of claim 1 wherein the ultrasound transducer is configured to acquire image data regarding contact between the ablation electrode and the tissue along a plane substantially perpendicular to the shaft.

11. The catheter of claim 1 wherein, in the uncompressed state and in the absence of an external force, the ablation electrode is (a) symmetric in a radial direction relative to the shaft, (b) symmetric in an axial direction relative to the shaft, or (c) a combination thereof.

12. The catheter of claim 11 wherein, in the uncompressed state and in the absence of the external force, the ablation electrode is ellipsoidal.

13. A method, comprising:
receiving one or more images captured by at least one ultrasound transducer of a catheter positioned within an anatomic structure of a patient, wherein:
the catheter includes (i) a shaft having a distal end portion positioned within the anatomic structure, (ii) a deformable ablation electrode at the distal end portion of the shaft, and (ii) the at least one ultrasound transducer,
the at least one ultrasound transducer includes an ultrasound transducer mounted on the ablation electrode or—mounted at a fixed location relative to the shaft within a volume at least partially defined by the ablation electrode,
the ablation electrode is transformable between a compressed state and an uncompressed state corresponding to a shape of the ablation electrode in the absence of an external force, and
the one or more images are received when the ablation electrode is in a deployed state corresponding to the uncompressed state or to a partially compressed state of the ablation electrode between the compressed state and the uncompressed state; and
based, at least in part, on the one or more images, determining displacement of the ablation electrode from the uncompressed state.

14. The method of claim 13 wherein determining displacement of the ablation electrode includes determining displacement of the ablation electrode from the uncompressed state in an axial direction relative to the shaft, displacement of the ablation electrode from the uncompressed state in a radial direction relative to the shaft, or a combination thereof.

15. The method of claim 13 wherein determining displacement of the ablation electrode includes determining a shape of the ablation electrode corresponding to the displacement.

16. The method of claim 15 further comprising transmitting an indication of the shape of the ablation electrode to a graphical user interface.

17. The method of claim 13, further comprising determining, based at least in part on the one or more images, apposition of the ablation electrode to tissue of the anatomic structure.

18. The method of claim 13, further comprising detecting, based at least in part on the determined displacement of the ablation electrode from the uncompressed state, contact between the ablation electrode and tissue of the anatomic structure.

19. The method of claim 18 wherein detecting the contact includes identifying regions of the ablation electrode contacting the tissue.

20. The method of claim 13 further comprising determining, based at least in part on the determined displacement of the ablation electrode from the uncompressed state, a direction and magnitude of a contact force between the ablation electrode and tissue of the anatomic structure.

21. The method of claim 13, further comprising determining, based at least in part on the determined displacement of the ablation electrode from the uncompressed state, a shape of the anatomic structure local to the ablation electrode.

22. The method of claim 21, further comprising generating a graphical representation of the anatomic structure based, at least in part, on the determined shape of the anatomic structure local to the ablation electrode.

23. The method of claim 13, further comprising:
delivering electrical energy to tissue of the anatomic structure; and
detecting, based at least in part on the one or more images, lesion progress while delivering the electrical energy to the tissue.

24. The method of claim 23 wherein detecting the lesion progress includes detecting microbubbles formed while the tissue is ablated via the electrical energy.

* * * * *